(12) United States Patent
Miyazaki

(10) Patent No.: US 8,591,913 B2
(45) Date of Patent: Nov. 26, 2013

(54) METHODS OF DECREASING ADIPOSE TISSUE

(75) Inventor: Toru Miyazaki, Tokyo (JP)

(73) Assignees: Toru Miyazaki, Tokyo (JP); Dainippon Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 13/356,456

(22) Filed: Jan. 23, 2012

(65) Prior Publication Data
US 2012/0202747 A1 Aug. 9, 2012

Related U.S. Application Data

(63) Continuation of application No. 12/785,808, filed on May 24, 2010, now abandoned.

(60) Provisional application No. 61/213,349, filed on Jun. 1, 2009.

(51) Int. Cl.
*A61K 39/00* (2006.01)
*A61K 38/00* (2006.01)
*A61K 38/18* (2006.01)
*C07K 14/475* (2006.01)

(52) U.S. Cl.
USPC ............ 424/198.1; 424/185.1; 530/350; 514/1.1

(58) Field of Classification Search
None
See application file for complete search history.

(56) References Cited

U.S. PATENT DOCUMENTS

| | | | |
|---|---|---|---|
| 6,046,314 | A | 4/2000 | Gebe et al. |
| 2006/0204525 | A1 | 9/2006 | Rest et al. |

FOREIGN PATENT DOCUMENTS

WO  WO 98/39443 A1  9/1998

OTHER PUBLICATIONS

Miyazaki, "New role for AIM expressed by macrophages in obesity," 39th Western Regional Meeting, Japanese Society of Nephrology, 2009, vol. 51, No. 6, p. 769 (with English-language translation).
Vera et al., "The CD5 ectodomain interacts with conserved fungal cell wall components and protects from zymosan-induced septic shock-like syndrome," PNAS, 2009, vol. 106, No. 5, pp. 1506-1511.
Renner et al., "DMBT1 Confers Mucosal Protection in Vivo and a Deletion Variant is Associated With Crohn's Disease," *Gastroenterology*, 2007, vol. 133, No. 5, pp. 1499-1509.
Arai et al., "A role for the apoptosis inhibitory factor AIM/Spα/Api6 in atherosclerosis development," *Cell Metabolism*, 2005, vol. 1, pp. 201-213.
Yusa et al., "AIM, a murine apoptosis inhibitory factor, induces strong and sustained growth inhibition of B lymphocytes in combination with TGF-β1," *Eur. J. Immunol.*, 1999, vol. 29, pp. 1086-1093.
Miyazaki, "Inhibition of Apoptosis by AIM (apoptosis inhibitor expressed by macrophages)," The SAISHIN IGAKU, 2000, vol. 55, No. 5, pp. 1064-1071.
Written Opinion of the International Searching Authority in corresponding International Application No. PCT/JP2010/058998; dated Aug. 10, 2010 (with partial English-language translation).
International Search Report in corresponding International Application No. PCT/JP2010/058998; dated Aug. 10, 2010 (with partial English-language translation).
Loftus et al., "Reduced Food Intake and Body Weight in Mice Treated with Fatty Acid Synthase Inhibitors," *Science*, 2000, vol. 288, pp. 2379-2381.
Miyazaki et al., "Increased Susceptibility of Thymocytes to Apoptosis in Mice Lacking AIM, a Novel Murine Macrophage-derived Soluble Factor Belonging to the Scavenger Receptor Cysteine-rich Domain Superfamily," *J. Exp. Med.*, 1999, vol. 189, No. 2, pp. 413-422.
Haruta et al., "Association of AIM, a Novel Apoptosis Inhibitory Factor, with Hepatitis via Supporting Macrophage Survival and Enhancing Phagocytotic. Function of Macrophages," *The Journal of Biological Chemistry*, 2001, vol. 276, No. 25, pp. 22910-22914.
Gebe et al., "Molecular Cloning, Mapping to Human Chromosome 1 q21-q23, and Cell Binding Characteristics of Spα, a New Member of the Scavenger Receptor Cysteine-rich (SRCR) Family of Proteins," *The Journal of Biological Chemistry*, 1997, vol. 272, No. 10, pp. 6151-6158.
Kumar et al., "Differential effects of a centrally acting fatty acid synthase inhibitor in lean and obese mice," PNAS, 2002, vol. 99, No. 4, pp. 1921-1925.
Shimokawa et al., "Effect of a fatty acid synthase inhibitor on food intake and expression of hypothalamic neuropeptides," PNAS, 2002, vol. 99, No. 1, pp. 66-71.
Chakravarthy et al., "Inactivation of hypothalamic FAS protects mice from diet-induced obesity and inflammation," *Journal of Lipid Research*, 2009, vol. 50 pp. 630-640.
Mickle J.E. et al., Genotype-phenotype relationships in cystic fibrosis. Med. Clin. North America, 2000, vol. 84(3), pp. 597-607.
Haruta et al., "Apoptosis Inhibitor Expressed by Macrophages Tempers Autoimmune Colitis and the Risk of Colitis-Based Carcinogenesis in TCRα$^{-/-}$ Mice," J. Clin. Immunol., vol. 27, pp. 549-556, 2007.
Mar. 5, 2013 Supplementary European Search Report issued in European Application No. 10783315.4.

*Primary Examiner* — Robert Landsman
*Assistant Examiner* — Bruce D Hissong
(74) *Attorney, Agent, or Firm* — Oliff & Berridge, PLC

(57) ABSTRACT

A pharmaceutical composition including, as an active ingredient, one of the following proteins (I) and (II): (I) an apoptosis inhibitor of macrophage; and (II) a protein which consists of an amino acid sequence having deletion, substitution, or addition of one or more amino acids in an amino acid sequence of the apoptosis inhibitor of macrophage and having homology to the amino acid sequence of the apoptosis inhibitor of macrophage, and has a function of inhibiting the differentiation of preadipocytes to mature adipocytes and/or a function of inducing lipolysis in the mature adipocytes.

8 Claims, 28 Drawing Sheets

FIG.1

(SEQ ID NO: 9 (base sequence) and SEQ ID NO: 1 (amino acid sequence))

```
Human AIM
1/1                          31/11                        61/21                        91/31
atg gct ctg ctg cta ttc tcc ctg atc ctt gcc aga cct gga ttc cta gcg tct cca tcg gtg ctg ggg ctg gtg gag ggg cgg gtg gag gtg gaa
Met ala leu phe ser leu ile ala ile cys thr arg pro gly phe leu ala ser pro gly val arg leu val gly gly leu his arg cys gly val glu 121/41                       151/51                       181/61                       211/71
cag aaa ggc cag tgg ggc acc gtg gat gac att aag gac gtg gct gtg ttg tgc cgg gag ctg ggc tgt gga gtg gcc agc gga acc cct agt ggt att ttg tat gag
gln lys gly gln trp gly thr val asp asp ile lys asp val ala val leu cys arg glu leu gly cys gly val ala ser gly thr pro ser gly ile leu tyr glu 241/81                       271/91                       301/101                      331/111
cca cca gca gaa aaa gag caa aag gtc ctc atc caa tca gtc agt tgc aca gga aca gaa gat aca ttg cct cag tgt gag caa gaa gaa gtt tat gat tgt tca cat gat gaa gat gct
pro pro ala glu lys glu gln lys val leu ile gln ser val ser cys thr gly thr glu asp thr leu ala gln cys glu gln glu glu val tyr asp cys ser his asp glu asp ala 361/121                      391/131                      421/141                      451/151
ggg gca tcg tgt gag aac cca gag agc tct ttc tcc cca gtc agg ctg gct gac ggc gtg agg cat tgc aag gga cgc gtg gaa gtg aag cac cag aac cag tgg tat
gly ala ser cys glu asn pro glu ser ser phe ser pro val arg leu ala asp gly val arg his cys lys gly arg val glu val lys his gln asn gln trp tyr 481/161                      511/171                      541/181                      571/191
acc gtg tgc cag aca ggc tgg agc ctc cgg gcc gca aag gct ggg cag ctg tgc cgg ggg agg gct gta ctg act caa aaa cgc tgc aac aag cat gcc tat ggc cga aaa ccc
thr val cys gln thr gly trp ser leu arg ala ala lys ala gly gln leu cys arg gly arg ala val leu thr gln lys arg cys asn lys his ala tyr gly arg lys pro 601/201                      631/211                      661/221                      691/231
atc tgg ctg agc cag atg gta gga gga tca tgc tca gga gca gca acc ctc tgc cct cag gat tgc cct tgg ggg aag aac acc tgc aac cat gat gaa gac acg tgg gtc gaa tgt gaa gat
ile trp leu ser gln met ser gly gly ser cys ser gly ala ala thr leu cys pro gln asp cys pro trp gly lys asn thr cys asn his asp glu asp thr trp val glu cys glu asp 721/241                      751/251                      781/261                      811/271
ccc ttt gac ttg aga cta gta gga gga gac aac ctc tcc ccc ttc cca gga cga ctg gag gtg ctg cac aag ggc gta tgg ggc tct gtc tgt gat gac aac tgg gga gaa aag gag gac cag gtg
pro phe asp leu arg leu val gly gly asp asn leu ser pro phe pro gly arg leu glu val leu his lys gly val trp gly ser val cys asp asp asn trp gly lys glu asp gln val 841/281                      871/291                      901/301                      931/311
gta tgc aag caa ctg ggc tgt ggg aag tcc ctc tcc ccc aga gac cgg aaa tgc tat ggc cct ggg gtt ggc cgc atc tgg ctg gat aat gtt cgt ctg cta gga cag
val cys lys gln leu gly cys gly lys ser leu ser pro arg asp arg lys cys tyr gly pro gly val gly arg ile trp leu asp asn val arg leu glu glu gln 961/321                      991/331                      1021/341
tcc ctg gag cag tgc cag cac cac cag gaa gat tgt ggg ttt cac gac tgc acc ggc ttt ggg gct gtc gtc atc tgc gga tag
ser leu glu gln cys gln his his gln glu asp cys gly phe his asp cys thr gly phe gly ala val val ile cys ser gly AMB
```

The Scavenger Receptor Cysteine Rich (SRCR) superfamily

FIG. 3

SRCR1

```
1    MALLFSLILA---ICTRPGFLASPSGVRLVGGLHRCEGRVEVEQKGQWGTVCDDGWDIKD    60   human (SEQ ID NO: 2)
     MA LF L LA    I    F  SP  V LVGG  HREGRVEVE  GQWGTVCDDGWD  D         consensus
     MAPLFNLMLAILSIFVGSCFSESPTKVQLVGGAHRCEGRVEVEHNGQWGTVCDDGWDRRD    60   mouse (SEQ ID NO: 6)

61   VAVLCRELGCGAASGTPSGILYEPPAEKEQKVLIQSVSCTGTEDTLAQCEQE-EVYDCSH   120  human
     VAV CREL CGA   TP G Y PPA    EQ VLIQ V C  GTEDTLAQCE       V DCSH    consensus
     VAVVCRELNCGAVIQTPRGASYQPPAS-EQRVLIQGVDCNGTEDTLAQCELNYDVFDCSH         mouse

SRCR2

121  DEDAGASCENPESSFSPVPEGVRLADGPGHCKGRVEVKHQNQWYTVCQTGWSLRAAKVVC   180  human (SEQ ID NO: 3)
     EDAGA CENP S      PE VRL DGPGHC  GRVEV HQ QW TVC   GW L   KVVC        consensus
     EEDAGAQCENPDSDLLFIPEDVRLVDGPGHCQGRVEVLHQSQWSTVCKAGWNLQVSKVVC         mouse (SEQ ID NO: 7)

181  RQLGCGRAVLTQKRCNKHAYGRKPIWLSQMSCSGREATLQDCPSGPWGKNTCNHDEDTWV   240  human
     RQLGCGRA LT   CNK   G PIW   MSCSG EA L   C      N C H EDTW           consensus
     RQLGCGRALLTYGSCNKSTQGKGPIWMGKMSCSGQEANLRSCLLSRLENN-CTHGEDTWM         mouse

SRCR3

241  ECEDPFDLRLVGGDNLCSGRLEVLHKGVWGSVCDDNWGEKEDQVVCKQLGCGKSLSPSFR   300  human (SEQ ID NO: 4)
     EC DPF  L LVGGD   CSGRLEVLHKGSWGSVCDDNWGEKEDQVVCKQLGCGKSL PS         consensus
     ECEDPFELKLVGGDTPCSGRLEVLHKGSWGSVCDDNWGEKEDQVVCKQLGCGKSLHPSPK         mouse (SEQ ID NO: 8)

301  DRKCYGPGVGRIWLDNVRCSGEEQSLEQCQHRFWGFHDCTHQEDVAVICSG            351  human
     RK YGPG GRIWLD V CSG EQSLE  C  HR WG HDCTH  EDV VIC                  consensus
     TRKIYGPGAGRIWLDDVNCSGKEQSLEFCRHRLWGYHDCTHKEDVEVICTDFDV               mouse
```

Fatty Gene Expression

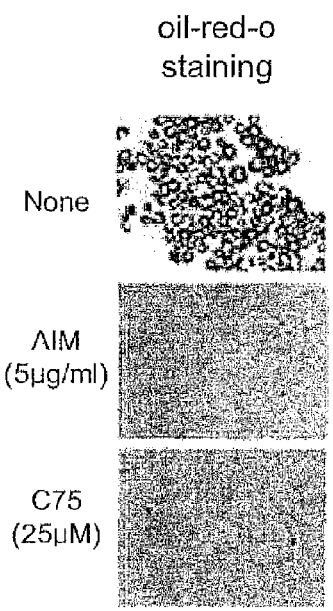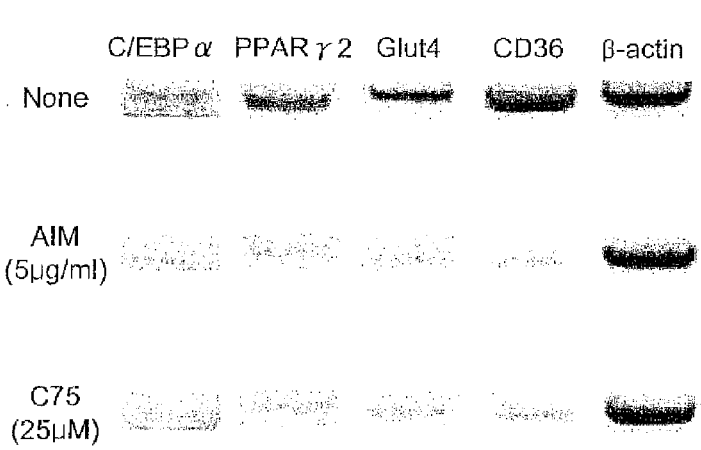
FIG.12A
FIG.12B
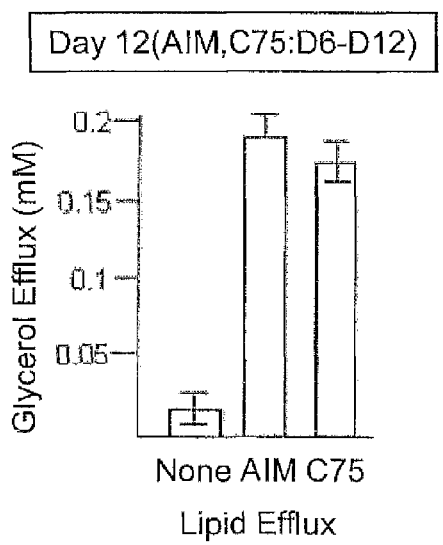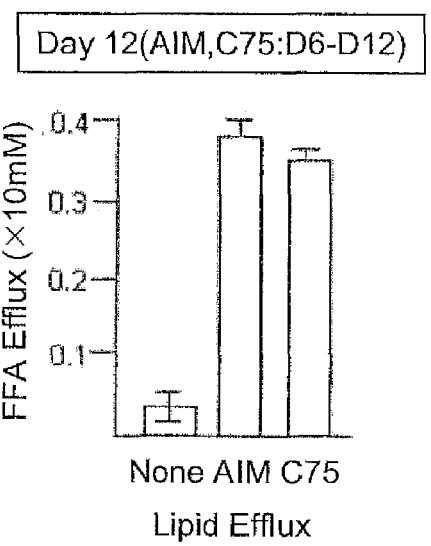
FIG.13A
FIG.13B 3-dimensional analysis AIM (Green) + CD36(Red)

3-dimensional analysis

AIM (Green) only 3-dimensional analysis 2-dimensional analysis no CD36 antibody with CD36 neutralizing antobody

AIM-/-

*Adiponectine-/- background*

AIM+/+

*Adiponectine-/- background*

FIG.22A
FIG.22B
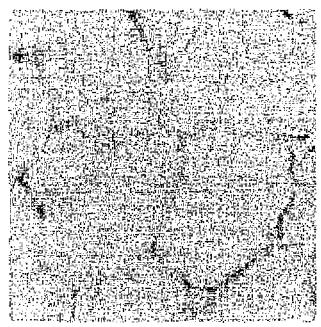
BSA injected
(control)
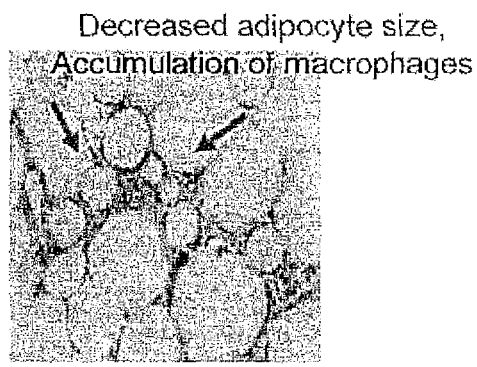
Decreased adipocyte size,
Accumulation of macrophages
rAIM injected FIG.27A +/+
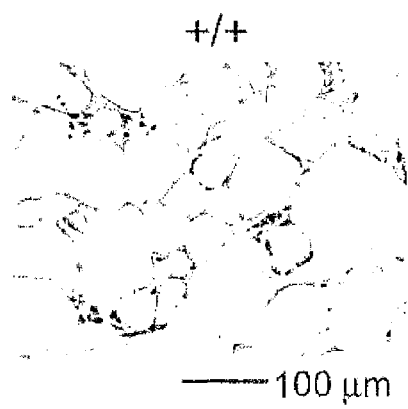
——100 μm
FIG.27B -/-
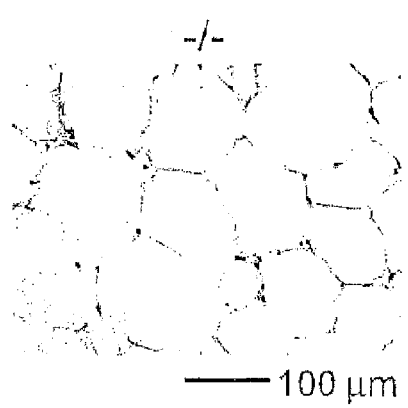
——100 μm
FIG.28A
Body
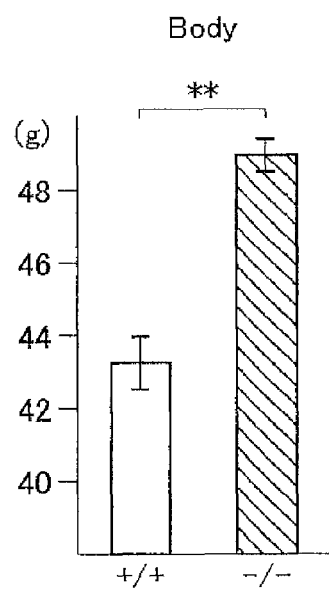
FIG.28B
Visceral fat
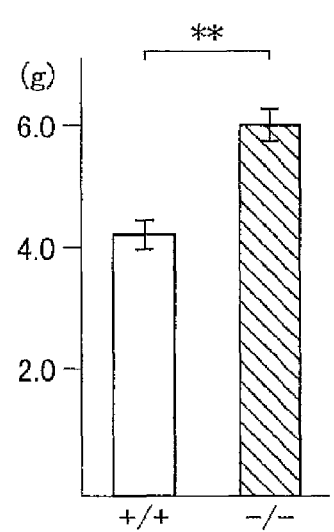
FIG.28C
Subcutaneous Fat
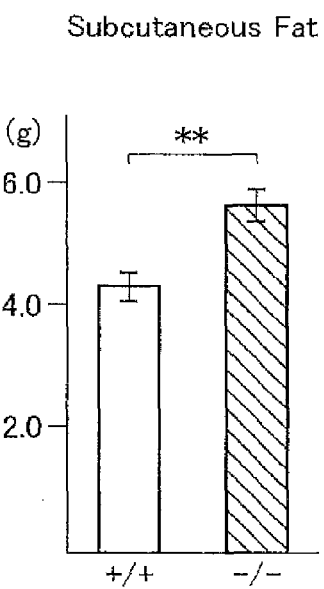

Body temperature

Oxygen Consumption

Food Intake

Locomotor activity

Body

Visceral fat

Subcutaneous Fat

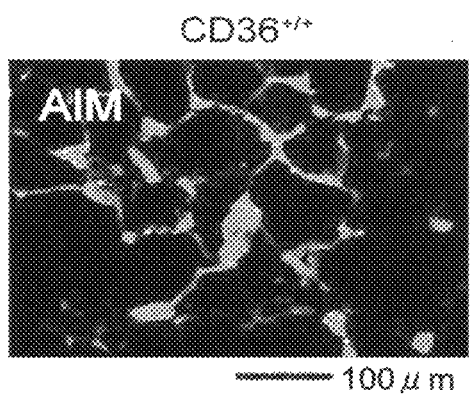 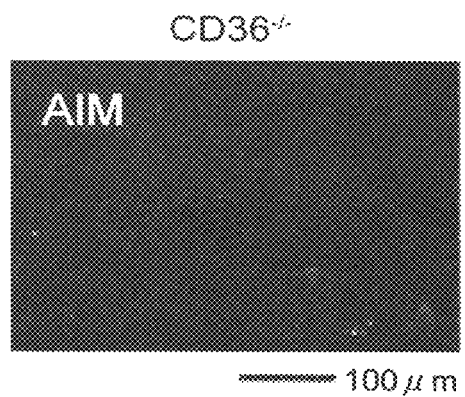
FIG.35A CD36+/+
FIG.35B CD36-/-

Pre-stimulation rhAIM (-)

rhAIM (10μg/ml)

METHODS OF DECREASING ADIPOSE TISSUE

CROSS-REFERENCE TO RELATED APPLICATION

This is a Divisional of application Ser. No. 12/728,808 filed May 24, 2010 and claims priority from U.S. Provisional Patent Application No. 61/213,349 filed on Jun. 1, 2009. The disclosure of the prior application is hereby incorporate by reference herein in its entirety.

BACKGROUND OF THE INVENTION

1. Field of the Invention

The present invention relates to a pharmaceutical composition, food or drink, and methods related thereto.

2. Description of the Related Art

Various anti-obesity drugs are currently being developed. For example, an inhibitor of fatty acid synthase (FAS) has been reported to cause remarkable loss of appetite by reducing the amount of a neuropeptide Y (NPY) produced in the hypothalamus, resulting in decrease in body weight and fat amount (see, e.g., Loftus, T. M. et al. Science 288: 2379-2381 (2000)).

SUMMARY OF THE INVENTION

However, there has been a problem in that an anti-obesity drug containing a low molecular compound which acts upon the cerebral nervous system as an active ingredient causes unfavorable side effects (such as anorexia).

Therefore, the development of a novel anti-obesity drug free of such side effects such as anorexia has been earnestly desired.

The present invention has been made in the light of the above-mentioned problem, and it is one object of the present invention is to provide a novel pharmaceutical composition, food or drink, and methods related thereto.

A pharmaceutical composition according to one embodiment of the present invention for solving the above-mentioned problem is a pharmaceutical composition including, as an active ingredient, one of the following proteins (I) and (II): (I) an apoptosis inhibitor of macrophage; and (II) a protein which consists of an amino acid sequence having deletion, substitution, or addition of one or more amino acids in an amino acid sequence of the apoptosis inhibitor of macrophage and having homology to the amino acid sequence of the apoptosis inhibitor of macrophage, and has a function of inhibiting the differentiation of preadipocytes to mature adipocytes and/or a function of inducing lipolysis in the mature adipocytes. According to the present invention, a novel pharmaceutical composition is provided.

A protein according to one embodiment of the present invention for solving the above-mentioned problem is a protein which is one of the protein (I) and the protein (II), in which the protein is used as an active ingredient of a pharmaceutical composition. According to the present invention, a protein for a novel pharmaceutical use is provided.

A method according to one embodiment of the present invention for solving the above-mentioned problem includes producing the pharmaceutical composition. According to the present invention, a method of producing a novel pharmaceutical composition is provided.

A method according to one embodiment of the present invention for solving the above-mentioned problem includes administering the pharmaceutical composition to a living body. According to the present invention, a method of administering a novel pharmaceutical composition to a living body is provided.

A food or drink according to one embodiment of the present invention for solving the above-mentioned problem is a food or drink including one of the following proteins (I) and (II): (I) an apoptosis inhibitor of macrophage; and (II) a protein which consists of an amino acid sequence having deletion, substitution, or addition of one or more amino acids in an amino acid sequence of the apoptosis inhibitor of macrophage and having homology to the amino acid sequence of the apoptosis inhibitor of macrophage, and has a function of inhibiting the differentiation of preadipocytes to mature adipocytes and/or a function of inducing lipolysis in the mature adipocytes. According to the present invention, a novel food or drink is provided.

A method according to one embodiment of the present invention for solving the above-mentioned problem includes producing the food or drink. According to the present invention, a method of producing a novel food or drink is provided.

BRIEF DESCRIPTION OF THE DRAWINGS

In the accompanying drawings:

FIG. 1 is an explanatory diagram correspondingly showing an amino acid sequence corresponding to SEQ ID NO: 1 and a base sequence corresponding to SEQ ID NO: 9 of cDNA of human AIM;

FIG. 3 is an explanatory diagram correspondingly showing the amino acid sequence of human AIM, which corresponds to SEQ ID NO: 1, an amino acid sequence of mouse AIM, which corresponds to SEQ ID NO: 5, and a consensus sequence which is common to them, the amino acid sequences of human SRCR1, SRCR2, and SRCR3 corresponding to SEQ ID NO: 2, SEQ ID NO: 3, and SEQ ID NO: 4, respectively, and the amino acid sequences of mouse SRCR1, SRCR2, and SRCR3 corresponding to SEQ ID NO: 6, SEQ ID NO: 7, and SEQ ID NO: 8, respectively.

FIG. 12A is an explanatory diagram showing one example of results of loading cells with AIM or the FAS inhibitor according to the schedule illustrated in FIG. 11A, and then staining fats in the cells with oil-red-o;

FIG. 12B is an explanatory diagram showing one example of results of analyzing the expression of genes in the cells loaded with AIM or the FAS inhibitor according to the schedule illustrated in FIG. 11A;

FIG. 13A is an explanatory diagram illustrating one example of results of measuring the amount of glycerol released in a culture supernatant when AIM or the FAS inhibitor was loaded according to the schedule illustrated in FIG. 11A;

FIG. 13B is an explanatory diagram illustrating one example of results of measuring the amount of free fatty acid released in the culture supernatant when AIM or the FAS inhibitor was loaded according to the schedule illustrated in FIG. 11A;

FIG. 22A is an explanatory diagram showing one example of results of observing adipose tissues in mice, to which BSA was administered, under a microscope;

FIG. 22B is an explanatory diagram showing one example of results of observing adipose tissues in mice, to which AIM was administered, under the microscope;

FIG. 27A is an explanatory diagram showing one example of results of staining visceral adipose tissue sections collected from the AIM$^{+/+}$ mice with HE and observing the sections under a phase contrast microscope;

FIG. 27B is an explanatory diagram showing one example of results of staining visceral adipose tissue sections collected from the AIM$^{-/-}$ mice with HE and observing the sections under the phase contrast microscope;

FIG. 28A is an explanatory diagram illustrating one example of results of measuring the body weight of the AIM$^{+/+}$ mice and the AIM$^{-/-}$ mice;

FIG. 28B is an explanatory diagram illustrating one example of results of measuring the weight of the visceral adipose tissue in the AIM$^{+/+}$ mice and the AIM$^{-/-}$ mice;

FIG. 28C is an explanatory diagram illustrating one example of results of measuring the weight of the subcutaneous adipose tissue in the AIM$^{+/+}$ mice and the AIM$^{-/-}$ mice;

FIG. 35A is an explanatory diagram showing one example of results of intravenously injecting rAIM into wild-type CD36$^{+/+}$ mice and analyzing the endoyctosis of rAIM into adipose tissue;

FIG. 35S is an explanatory diagram showing one example of results of intravenously injecting rAIM into CD36$^{-/-}$ mice and analyzing the endocytosis of rAIM into the adipose tissue;

DETAILED DESCRIPTION OF THE INVENTION

Hereinafter, one embodiment of the present invention is described. It should be noted that the present invention is not limited in any way by the embodiment of the present invention.

First, an apoptosis inhibitor of macrophage (hereinafter referred to as "AIM") which is a protein associated with the present invention is described.

AIM is a secretory type protein in which three SRCR (scavenger receptor cysteine-rich) domains (referred to as SRCR1, SRCR2, and SRCR3 sequentially from an N terminal side) have been conserved in its amino acid sequence and that has a molecular structure in which the three SRCR domains are tandemly linked.

A research group of the inventors of the present invention reported mouse AIM for the first time as a secretory type protein being specifically produced by macrophages and having a function of inhibiting the apoptosis of macrophages, based on the results of cloning a mouse gene, and producing and analyzing knockout mice (Document 1: Miyazaki, T. at al. Increased susceptibility of thymocytes to apoptosis in mice lacking AIM, a novel murine macrophage-derived soluble factor belonging to the scavenger receptor cysteine-rich domain superfamily. *J Exp Med.* 189: 413-422, 1999; Document 2: Haruta, I., Kato, Y., Hashimoto, E., Minjares, C., Kennedy, S., Uto, H., Yamauchi, K., Kobayashi, M., Yusa, S., Muller, U., Hayashi, N. & Miyazaki, T. Association of AIM, a novel apoptosis inhibitory factor, with hepatitis via supporting macrophage survival and enhancing phagocytotic function of macrophages. *J. Biol. Chem.* 276: 22910-22914 (2001).

Meanwhile, a human gene sequence was reported as "SPα" (secretion protein a) by another research group (Document 3: Gebe, J. A. et al. Molecular cloning, mapping to human chromosome 1 q21-q23, and cell binding characteristics of Spalpha, a new member of the scavenger receptor cysteine-rich (SRCR) family of proteins. *J Biol. Chem.* 272: 6151-6158, 1997). Subsequently, a term "Api6" was given to the gene as part of a genome sequence project. Further, a term "CD5L" was also given because its structure having three SRCR domains was similar to that of an extracellular domain of CD5. In addition, it has been recently proposed that those terms be unified to "CD5L". However, if the term of a molecule should reflect its function, it is considered appropriate that any term for the protein be unified to "AIM".

Mouse AIM is a protein consisting of an amino acid sequence shown in SEQ ID NO: 5. Human AIM is a protein consisting of an amino acid sequence shown in SEQ ID NO: 1. It should be noted that the amino acid sequence of human AIM (amino acid sequence shown in SEQ ID NO: 1) and a base sequence of its cDNA (base sequence shown in SEQ ID NO: 9) are shown correspondingly in FIG. 1.

Next, characteristics of the AIM molecule are described. Mouse AIM is a molecule originally discovered as a new member of the scavenger-receptor cysteine-rich super-family (SRCR-SF) and having a molecular weight of 54 kDa.

Figure 2:
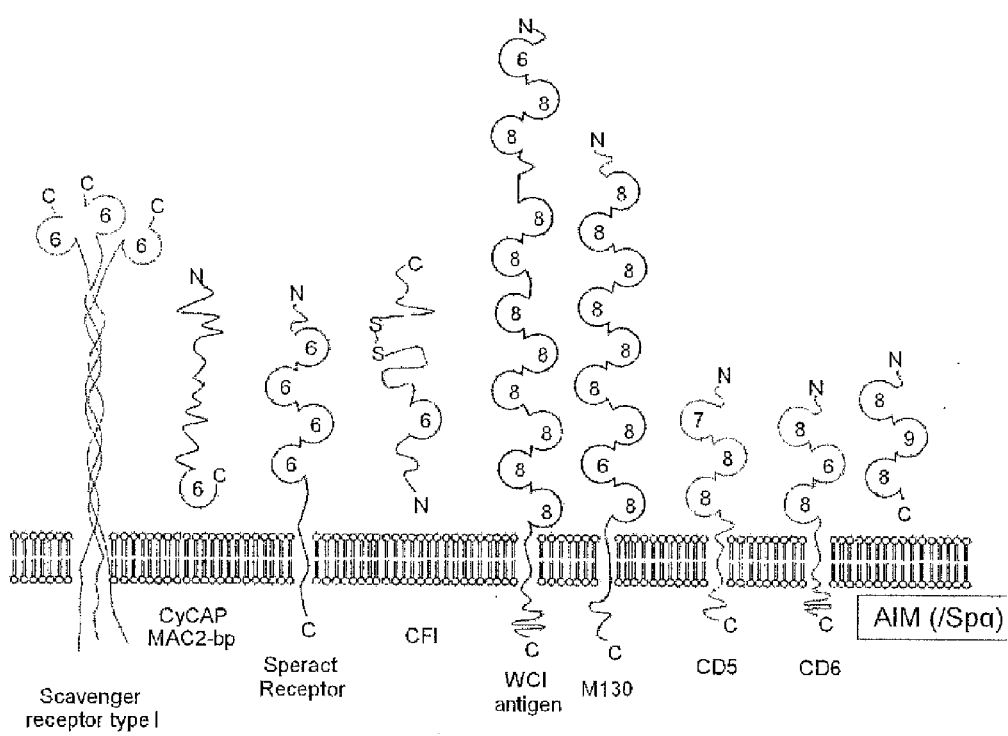
FIG. 2 is an explanatory diagram illustrating examples of molecules belonging to SRCR-SF.

Examples of the molecules belonging to the SRCR-SF are illustrated in FIG. 2. As illustrated in FIG. 2, the AIM molecule is formed by tandemly linking three SRCR domains conserved among the member molecules belonging to the SRCR-SF and containing cysteine abundantly.

The AIM has a signal peptide closer to an N terminal side than SRCR1 which is the SRCR domain located most closely to the N terminal among the SRCR domains, but has no region corresponding to a transmembrane domain or an intracellular domain, and is a typical secretory type protein determined from its sequence. It should be noted that, as illustrated in FIG. 2, the other SRCR-SF members such as CD5 and CD6 similarly having three SRCR domains are transmembrane type proteins.

By the way, the term "SRCR-SF" was given because a cysteine-rich domain was first described in a scavenger receptor. Not all of the molecules having the domain have a scavenging function. Actually, mouse AIM has no scavenging function.

Mouse AIM has 68% homology to human AIM in their amino acid sequences. Mouse AIM has three N-glycosylation sites, but human AIM has no N-glycosylation site.

In FIG. 3, the amino acid sequence of human AIM (amino acid sequence by a single-letter code shown in SEQ ID NO: 11), the amino acid sequence of mouse AIM (amino acid sequence by the single-letter code shown in SEQ ID NO: 5) and a consensus sequence which is common to them are shown correspondingly. In FIG. 3, a portion surrounded with a square frame from the top column to the third column out of the six columns corresponds to the amino acid sequence of the SRCR1 domain (amino acid sequence shown in SEQ ID NO: 2 in human AIM and amino acid sequence shown in SEQ ID NO: 6 in mouse AIM). A portion surrounded with a square frame from the third column to the fifth column corresponds to the amino acid sequence of the SRCR2 domain (amino acid sequence shown in SEQ ID NO: 3 in human AIM and amino acid sequence shown in SEQ ID NO: 7 in mouse AIM). A portion surrounded with a square frame from the fifth column to the sixth column corresponds to the amino acid sequence of the SRCR3 domain (amino acid sequence shown in SEQ ID NO: 4 in human AIM and amino acid sequence shown in SEQ ID NO: 8 in mouse AIM).

Further, the functions of AIM known so far are described. The functions of AIM were partially demonstrated initially by analyzing the knockout mice (Document 1 above). That is, it was found that intraperitoneal macrophages had low resistance to apoptosis induced by various stimulations in AIM-deficient (AIM$^{-/-}$) mice, although those mice basically exhibited no abnormality. Similarly, when AIM$^{-/-}$ macrophages were loaded with recombinant AIM molecules, their resistance to the apoptosis was enhanced. That is, it was demonstrated that AIM had a function of inhibiting the apoptosis of macrophages.

Inductive stimulations for the apoptosis inhibited by AIM are not limited, and AIM inhibits apoptosis induced by various stimulations such as Fas/CD95, radiation, steroid, infection (*Listeria* or the like), and oxidized LDL. It is still unknown by what mechanism AIM inhibits the apoptosis.

Also, as a result of an extensive study on such AIM, the inventors of the present invention have uniquely found an unexpected function that AIM inhibits the differentiation of preadipocytes to mature adipocytes and induces lipolysis in the mature adipocytes, and completed the present invention.

Further, surprisingly, it has been demonstrated that although AIM is a secretory type protein, AIM exerts its function by being internalized into the cytoplasm via CD36 expressed on the surface of the cell membrane.

This fact means that AIM specifically acts only upon the cells which express CD36. That is, for example, AIM does not act upon cells in the cerebral nervous system, which do not express CD36.

Further, since AIM is a protein, AIM does not pass through a blood-brain barrier. Therefore, AIM causes no side effect such as anorexia which has been caused by conventional anti-obesity drugs using a low molecular substance as an active ingredient.

Next, a pharmaceutical composition according to an embodiment of the present invention (hereinafter referred to as "pharmaceutical composition of the present invention") is described. The pharmaceutical composition of the present invention contains a specific protein including the above-mentioned AIM (hereinafter referred to as "protein of the present invention") as an active ingredient.

That is, the pharmaceutical composition of the present invention is a pharmaceutical composition including, as an active ingredient, one of the following proteins (I) and (II): (I) an apoptosis inhibitor of macrophage; and (II) a protein which consists of an amino acid sequence having deletion, substitution, or addition of one or more amino acids in the amino acid sequence of the apoptosis inhibitor of macrophage and having homology to the amino acid sequence of the apoptosis inhibitor of macrophage, and has at least one of a function of inhibiting the differentiation of preadipocytes to mature adipocytes and a function of inducing lipolysis in the mature adipocytes. Here, the above-mentioned protein (I) is native AIM and the above-mentioned protein (II) is a mutant protein of the native AIM.

The protein of the present invention is one of the above-mentioned protein (I) and the above-mentioned protein (II), and is a protein for the use as an active ingredient of a pharmaceutical composition. The protein of the present invention is also a protein for the use, for example, in diagnosis, treatment or prevention of any diseases described later.

The pharmaceutical composition of the present invention contains, for example, AIM of a human or AIM of an animal other than a human (hereinafter referred to simply as "animal") as the active ingredient.

The protein of the present invention is, for example, the protein consisting of the amino acid sequence shown in SEQ ID NO: 1. That is, in this case, the protein of the present invention is human AIM and is a secretory type protein having the function of inhibiting the apoptosis of macrophages (hereinafter referred to as "apoptosis inhibitory function").

In addition, the protein of the present invention is, for example, AIM of an animal. The animal is not particularly limited as long as the animal is an animal other than a human. The animal, for example, is a mammal such as a rodent (a mouse, a rat, a guinea pig, a rabbit etc.), a dog, a cat, a pig, a cow or bull, a horse, or a monkey. More specifically, the protein of the present invention is, for example, mouse AIM, dog AIM, or cat AIM.

The protein of the present invention is, for example, a protein consisting of the amino acid sequence shown in SEQ ID NO: 5. That is, in this case, the protein of the present invention is mouse AIM and is a secretory type protein having a function of inhibiting apoptosis.

Those AIMs may be produced, for example, by utilizing a gene recombination technology. That is, first, cDNA of human AIM shown in SEQ ID NO: 9 ("tag" at the 3' terminus of the amino acid sequence shown in SEQ ID NO: 9 is a stop codon) is incorporated into an appropriate expression vector such as pCAGGS. Then, the expression vector is introduced into an animal cell line such as a CHO cell line or a 293T cell line, and human AIM is produced by the animal cells.

Human AIM is a secretory type protein, and thus the produced recombinant human AIM is released in a culture supernatant. Therefore, for example, a tag peptide (9 to 12 amino acid residues) such as HA is previously added to the human AIM, and the human AIM is purified from the culture supernatant using a purification column to which an antibody against the tag peptide has been immobilized. In addition, when an anti-AIM antibody is obtained in advance, for example, it is also possible to purify human AIM with no tag from the culture supernatant using the anti-AIM antibody.

It should be noted that AIM of an animal other than a human is also produced in a similar manner. That is, in the case of mouse AIM, for example, recombinant mouse AIM is obtained in the same procedure as in the case of the above-mentioned human AIM by using cDNA of mouse AIM shown in SEQ ID NO: 10 ("tga" at the 3' terminus of the amino acid sequence shown in SEQ ID NO: 10 is a stop codon).

In the case of AIM of another animal species such as a dog or a cat, cDNA of AIM is acquired from a cDNA library of the other animal species based on three characteristics, i.e., conserving SRCR domains, having the structure of tandemly linked three SRCR domains, and being a secretory type protein, and recombinant AIM is obtained using the same procedure as in the case of human AIM.

The amino acid sequence of AIM is also acquired, for example, from a known database such as a database provided by the National Center for Biotechnology Information (NCBI). Specifically, for example, the amino acid sequences of dog AIM, chimpanzee AIM, and rat AIM are shown in SEQ ID NOS: 11, 12, and 13, respectively.

Further, in the case of an AIM analogous protein having a mutation described later in the amino acid sequence of any one of those native AIMs, a recombinant mutant AIM is obtained in the same procedure, for example, by synthesizing and using a corresponding cDNA.

The protein of the present invention may be a protein (AIM mutant protein) having a mutation in the amino acid sequence of any one of the above-mentioned native AIMs within a range in which at least one of its function of inhibiting the differentiation of preadipocytes to mature adipocytes (hereinafter referred to as "adipogenesis inhibitory function") and its function of inducing lipolysis in the mature adipocytes (hereinafter referred to as "lipolytic function") are not impaired.

That is, the pharmaceutical composition of the present invention contains, for example, the human or animal AIM mutant protein as the active ingredient.

The AIM mutant protein is a protein which consists of an amino acid sequence having deletion, substitution, or addition of one or more amino acids in the amino acid sequence of AIM and having a homology to the amino acid sequence of AIM and has an adipogenesis inhibitory function and/or a lipolytic function, as described above.

It should be noted that the AIM mutant protein described below may further have the following characteristics even when they are not explicitly described. That is, the AIM mutant protein may be a secretory type protein. The AIM mutant protein may have an apoptosis inhibitory function. The AIM mutant protein may be a protein having 300 to 400, preferably 320 to 380, and more preferably 340 to 360 amino acid residues in its amino acid sequence.

When the amino acid sequence of the AIM mutant protein has 80% or more homology to the amino acid sequence of the native AIM, or when the amino acid sequence of the domains in the AIM mutant protein has 80% or more homology to the amino acid sequence of the domains in the native AIM, the homology is preferably 85% or more, more preferably 90% or more, and particularly preferably 95% or more.

The AIM mutant protein may be a protein which acts upon cells via CD36 in the same way as AIM. In this case, the AIM mutant protein specifically acts upon cells having CD36 in the same way as AIM. The AIM mutant protein may be a protein which is bound to FAS of cells and reduces activity of the FAS in the same way as AIM.

The protein of the present invention is, for example, a protein which consists of an amino acid sequence having deletion, substitution, or addition of one or more amino acids in the amino acid sequence shown in SEQ ID NO: 1 and having 80% or more homology to the amino acid sequence shown in SEQ ID NC: 1, and has at least one of an adipogenesis inhibitory function and a lipolytic function.

The protein of the present invention may be a secretory type protein. In this case, the protein of the present invention has an amino acid sequence characteristic for secretory type proteins. Specifically, the protein of the present invention is, for example, a secretory type protein having a molecular structure in which the protein has a hydrophobic short sequence (leader sequence) at the N terminus (initial portion) of its amino acid sequence and does not have a transmembrane sequence (transmembrane region, also hydrophobic) nor an intracellular domain. Actually, native AIM is a secretory type protein having such a molecular structure. The protein of the present invention may have an apoptosis inhibitory function.

The protein of the present invention is, for example, a protein which consists of an amino acid sequence having deletion, substitution, or addition of one or several amino acids in the amino acid sequence shown in SEQ ID NO: 1 and has at least one of an adipogenesis inhibitory function and a lipolytic function.

In this case, the protein of the present invention is a protein consisting of an amino acid sequence having 80% or more homology to the amino acid sequence shown in SEQ ID NO: 1. The protein of the present invention may be a secretory type protein. The protein of the present invention may have an apoptosis inhibitory function.

In addition, the protein of the present invention is, for example, a protein which consists of an amino acid sequence having deletion, substitution, or addition of one or more amino acids in the amino acid sequence shown in SEQ ID NO: 1, is formed by tandemly linking a first domain consisting of one of the amino acid sequence shown in SEQ ID NO: 2 and an amino acid sequence having deletion, substitution, or addition of one or more amino acids in the amino acid sequence shown in SEQ ID NO: 2 and having 80% or more homology to the amino acid sequence shown in SEQ ID NO: 2, a second domain consisting of one of the amino acid sequence shown in SEQ ID NO: 3 and an amino acid sequence having deletion, substitution, or addition of one or more amino acids in the amino acid sequence shown in SEQ ID NO: 3 and having 80% or more homology to the amino acid sequence shown in SEQ ID NO: 3, and a third domain consisting of one of the amino acid sequence shown in SEQ ID NO: 4 and an amino acid sequence having deletion, substitution, or addition of one or more amino acids in the amino acid sequence shown in SEQ ID NO: 4 and having 80% or more homology to the amino acid sequence shown in SEQ ID NO: 4, and has at least one of an adipogenesis inhibitory function and a lipolytic function.

That is, the protein of the present invention has three domains, i.e., the SRCR1 domain of human AIM or a mutated form thereof, the SRCR2 domain of human AIM or a mutated form thereof, and the SRCR3 domain of human AIM or a mutated form thereof. In this case, the protein of the present invention may be a protein consisting of an amino acid sequence having 80% or more homology to the amino acid sequence shown in SEQ ID NO: 1. The protein of the present invention may be a secretory type protein. The protein of the present invention may have an apoptosis inhibitory function. The protein of the present invention may be a protein having 300 to 400, preferably 320 to 380, and more preferably 340 to 360 amino acid residues in its amino acid sequence.

In addition, at least one of the first domain, the second domain, and the third domain may be a domain consisting of an amino acid sequence having deletion, substitution, or addition of one or more amino acids in the amino acid sequence shown in SEQ ID NO: corresponding to the at least one domain and having 80% or more homology to the amino acid sequence shown in the corresponding Sequence Listing. The first domain, the second domain, and the third domain may be sequentially linked from the N terminal side.

Further, the protein of the present invention is, for example, a protein which is formed by tandemly linking a first domain consisting of one of the amino acid sequence shown in SEQ ID NO: 2 and an amino acid sequence having deletion, substitution, or addition of one or several amino acids in the amino acid sequence shown in SEQ ID NO: 2, a second domain consisting of one of the amino acid sequence shown in SEQ ID NO: 3 and an amino acid sequence having deletion, substitution, or addition of one or several amino acids in the amino acid sequence shown in SEQ ID NO: 3, and a third domain consisting of one of the amino acid sequence shown in SEQ ID NO: 4 and an amino acid sequence having deletion, substitution, or addition of one or several amino acids in the amino acid sequence shown in SEQ ID NO: 4, and has at least one of an adipogenesis inhibitory function and a lipolytic function.

The protein of the present invention is, for example, a protein which is formed by tandemly linking a first domain (SRCR1 domain of human AIM) consisting of the amino acid sequence shown in SEQ ID NO: 2, a second domain (SRCR2 domain of human AIM) consisting of the amino acid sequence shown in SEQ ID NO: 3, and a third domain (SRCR3 domain of human AIM) consisting of the amino acid sequence shown in SEQ ID NO: 4, and has at least one of an adipogenesis inhibitory function and a lipolytic function.

That is, the protein of the present invention has three domains, i.e., the SRCR1 domain, the SRCR2 domain, and the SRCR3 domain of human AIM as the SRCR domains. In this case, the protein of the present invention may be a protein consisting of an amino acid sequence having 80% or more homology to the amino acid sequence shown in SEQ ID NO: 1. The protein of the present invention may be a secretory type protein. The protein of the present invention may have an apoptosis inhibitory function. The protein of the present invention may be a protein having 300 to 400, preferably 320 to 380, and more preferably 340 to 360 amino acid residues in its amino acid sequence.

In addition, any one of the proteins of the present invention having the first domain, the second domain, and the third domain described above may be a protein which is formed by tandemly and directly linking the first domain, the second domain, and the third domain, and has at least one of an adipogenesis inhibitory function and a lipolytic function.

That is, in this case, the protein of the present invention is a protein consisting of an amino acid sequence formed by tandemly and directly linking the amino acid sequence of the first domain, the amino acid sequence of the second domain, and the amino acid sequence of the third domain. Therefore, in this case, the protein of the present invention has no connecting portion between the domains, which corresponds to, for example, the amino acid sequence of the connecting portion between the SRCR1 domain and the SRCR2 domain or the amino acid sequence of the connecting portion between the SRCR2 domain and the SRCR3 domain in human AIM. However, the protein of the present invention having the first domain, the second domain, and the third domain described above is not limited thereto, and may be a protein having a connecting portion between the domains.

In addition, the protein of the present invention is, for example, a protein which is formed by tandemly linking a first domain consisting of one of the amino acid sequence shown in SEQ ID NO: 2 and an amino acid sequence having deletion, substitution, or addition of one or more amino acids in the portion other than the consensus sequence (consensus sequence in the SRCR1 domain shown in FIG. 3) in the amino acid sequence shown in SEQ ID NO: 2, a second domain consisting of one of the amino acid sequence shown in SEQ ID NO: 3 and an amino acid sequence having deletion, substitution, or addition of one or more amino acids in the portion other than the consensus sequence (consensus sequence in the SRCR2 domain shown in FIG. 3) in a amino acid sequence shown in SEQ ID NO: 3, and a third domain consisting of one of the amino acid sequence shown in SEQ ID NO: 4 and an amino acid sequence having deletion, substitution, or addition of one or more amino acids in the portion other than the consensus sequence (consensus sequence in the SRCR3 domain shown in FIG. 3) in the amino acid sequence shown in SEQ ID NO: 4, and has at least one of an adipogenesis inhibitory function and a lipolytic function.

That is, the protein of the present invention has three domains, i.e., the SRCR1 domain of human AIM or a domain having a mutation in the portion other than the consensus sequence in the SRCR1 domain of human AIM, the SRCR2 domain of human AIM or a domain having a mutation in the portion other than the consensus sequence in the SRCR2 domain of human AIM, and the SRCR3 domain of human AIM or a domain having a mutation in the portion other than the consensus sequence in the SRCR3 domain of human AIM. In this case, the protein of the present invention is a protein consisting of an amino acid sequence having deletion, substitution, or addition of one or more amino acids in the amino acid sequence shown in SEQ ID NO: 1. That is, the protein of the present invention may be a protein consisting of an amino acid sequence having 80% or more homology to the amino acid sequence shown in SEQ ID NO: 1. The protein of the present invention may be a secretory type protein. The protein of the present invention may have an apoptosis inhibitory function. The protein of the present invention may be a protein having 300 to 400, preferably 320 to 380, and more preferably 340 to 360 amino acid residues in its amino acid sequence.

In addition, at least one of the first domain, the second domain, and the third domain may be a domain consisting of an amino acid sequence having deletion, substitution, or addition of one or more amino acids in the portion other than the consensus sequence in the amino acid sequence shown in a SEQ ID NO: corresponding to the at least one domain. At least one of the first domain, the second domain, and the third domain may be a domain consisting of an amino acid sequence having 80% or more homology to the amino acid sequence shown in a SEQ ID NO: corresponding to the at least one domain. That is, at least one of the first domain, the second domain, and the third domain may be a domain consisting of an amino acid sequence having deletion, substitution, or addition of one or several amino acids in the portion other than the consensus sequence in the amino acid sequence shown in a SEQ ID NO: corresponding to the at least one domain. The first domain, the second domain, and the third domain may be sequentially linked from the N terminal side.

Any one of the protein of the present inventions having the first domain, the second domain, and third domain, which have a mutation in the portion other than the consensus sequence, described above may be a protein which is formed by tandemly and directly linking the first domain, the second domain, and the third domain, and has at least one of an adipogenesis inhibitory function and a lipolytic function.

That is, in this case, the protein of the present invention is a protein consisting of an amino acid sequence formed by tandemly and directly linking the amino acid sequence of the first domain, the amino acid sequence of the second domain, and the amino acid sequence of the third domain. However, the protein of the present invention having the first domain, the second domain, and third domain, which have a mutation in the portion other than the consensus sequence, described above is not limited thereto, and may be a protein having a connecting portion between the domains.

Further, the protein of the present invention is, for example, one of the following proteins (x1), (x2), and (x3), which has at least one of an adipogenesis inhibitory function and a lipolytic function: (x1) one of a first domain protein consisting of the amino acid sequence shown in SEQ ID NO: 2 and a protein formed by tandemly linking a plurality of the first domain proteins; (x2) one of a second domain protein consisting of the amino acid sequence shown in SEQ ID NO: 3 and a protein formed by tandemly linking a plurality of the second domain proteins; and (x3) one of a third domain protein consisting of the amino acid sequence shown in SEQ ID NO: 4 and a protein formed by tandemly linking a plurality of the third domain proteins.

That is, in this case, the protein of the present invention is, for example, a protein consisting of the SRCR1 domain of human AIM (first domain protein), or a protein formed by tandemly linking a plurality of the SRCR1 domains (protein (x1) described above). The protein of the present invention is, for example, a protein consisting of the SRCR2 domain of human AIM (second domain protein), or a protein formed by tandemly linking a plurality of the SRCR2 domains (protein (x2) described above). The protein of the present invention is, for example, a protein consisting of one of the SRCR3 domain of human AIM (third domain protein), or a protein formed by tandemly linking a plurality of the SRCR3 domains (protein (x3) described above).

Likewise, the protein of the present invention may be, for example, one of the following proteins (y1), (y2), and (y3), which has at least one of an adipogenesis inhibitory function and a lipolytic function: (y1) one of a first domain protein consisting of an amino acid sequence having deletion, substitution, or addition of one or more amino acids in the amino acid sequence shown in SEQ ID NO: 2 and having 80% or more homology to the amino acid sequence shown in SEQ ID NO: 2, and a protein formed by tandemly linking a plurality of the first domain proteins; (y2) one of a second domain protein consisting of an amino acid sequence having deletion, substitution, or addition of one or more amino acids in the amino acid sequence shown in SEQ ID NO: 3 and having 80% or more homology to the amino acid sequence shown in SEQ ID NO: 3, and a protein formed by tandemly linking a plurality of the second domain proteins; and (y3) one of a third domain protein consisting of an amino acid sequence having deletion, substitution, or addition of one or more amino acids in the amino acid sequence shown in SEQ ID NO: 4 and having 80% or more homology to the amino acid sequence shown in SEQ ID NO: 4, and a protein formed by tandemly linking a plurality of the third domain proteins.

Likewise, the protein of the present invention may be, for example, one of the following proteins (z1), (z2), and (z3), which has at least one of an adipogenesis inhibitory function and a lipolytic function: (z1) one of a first domain protein consisting of an amino acid sequence having deletion, substitution, or addition of one or more amino acids in the portion other than the consensus sequence in the amino acid sequence shown in SEQ ID NO: 2, and a protein formed by tandemly linking a plurality of the first domain proteins; (z2) one of a second domain protein consisting of an amino acid sequence having deletion, substitution, or addition of one or more amino acids in the portion other than the consensus sequence in the amino acid sequence shown in SEQ ID NO: 3, and a protein formed by tandemly linking a plurality of the second domain proteins; and (z3) one of a third domain protein consisting of an amino acid sequence having deletion, substitution, or addition of one or more amino acids in the portion other than the consensus sequence in the amino acid sequence shown in SEQ ID NO: 4, and a protein formed by tandemly linking a plurality of the third domain proteins.

Any one of the protein of the present inventions having the first domain protein, the second domain protein, or the third domain protein described above may be a protein formed by tandemly and directly linking a plurality of the first domain proteins, a plurality of the second domain proteins, or a plurality of the third domain proteins. However, the protein of the present invention is not limited thereto, and may be a protein having a connecting portion between the domains.

The protein of the present invention is, for example, a protein which consists of an amino acid sequence having deletion, substitution, or addition of one or more amino acids in an amino acid sequence of AIM of an animal and having 80% or more homology to the amino acid sequence of AIM of an animal, and has at least one of an adipogenesis inhibitory function and a lipolytic function.

In this case, the animal is not particularly limited as long as the animal is an animal other than a human. The animal, for example, is a mammal such as a rodent (a mouse, a rat, a guinea pig, a rabbit etc.), a dog, a cat, a pig, a cow or bull, a horse, or a monkey. More specifically, the animal is, for example, a mouse, a dog, or a cat.

That is, the protein of the present invention is, for example, a protein which consists of an amino acid sequence having deletion, substitution, or addition of one or more amino acids in the amino acid sequence shown in SEQ ID NO: 5 (amino acid sequence of mouse AIM) and having 80% or more homology to the amino acid sequence shown in SEQ ID NO: 5, and has at least one of an adipogenesis inhibitory function and a lipolytic function.

In this case, the protein of the present invention may be a secretory type protein. The protein of the present invention may have an apoptosis inhibitory function.

Likewise, the protein of the present invention is, for example, a protein which consists of an amino acid sequence having deletion, substitution, or addition of one or more amino acids in an amino acid sequence shown in SEQ ID NO: 11 (amino acid sequence of dog AIM), an amino acid sequence shown in SEQ ID NO: 12 (amino acid sequence of chimpanzee AIM), or an amino acid sequence shown in SEQ ID NO: 13 (amino acid sequence of rat AIM) and having 80% or more homology to the amino acid sequence shown in SEQ ID NO: 11, SEQ ID NO: 12, or SEQ ID NO: 13, and has at least one of an adipogenesis inhibitory function and a lipolytic function.

The protein of the present invention is also, for example, a protein which consists of an amino acid sequence having deletion, substitution, or addition of one or several amino acids in an amino acid sequence of AIM of an animal, and has at least one of an adipogenesis inhibitory function and a lipolytic function.

Also in this case, the animal is not particularly limited as long as the animal is an animal other than a human. The animal, for example, is a mammal such as a rodent (a mouse, a rat, a guinea pig, a rabbit etc.), a dog, a cat, a pig, a cow or bull, a horse, or a monkey. More specifically, the animal is, for example, a mouse, a dog, or a cat.

That is, the protein of the present invention is, for example, a protein which consists of an amino acid sequence having deletion, substitution, or addition of one or several amino acids in the amino acid sequence shown in SEQ ID NO: 5 (amino acid sequence of mouse AIM), and has at least one of an adipogenesis inhibitory function and a lipolytic function.

In this case, the protein of the present invention is a protein consisting of an amino acid sequence having 80% or more homology to the amino acid sequence shown in SEQ ID NO: 5. The protein of the present invention may be a secretory type protein. The protein of the present invention may have an apoptosis inhibitory function.

Likewise, the protein of the present invention is, for example, a protein which consists of an amino acid sequence having deletion, substitution, or addition of one or several amino acids in the amino acid sequence shown in SEQ ID NO: 11 (amino acid sequence of dog AIM), the amino acid sequence shown in SEQ ID NO: 12 (amino acid sequence of chimpanzee AIM), or the amino acid sequence shown in SEQ ID NO: 13 (amino acid sequence of rat AIM) and has at least one of an adipogenesis inhibitory function and a lipolytic function.

The protein of the present invention is, for example, a protein which consists of an amino acid sequence having deletion, substitution, or addition of one or more amino acids in an amino acid sequence of AIM of an animal having an SRCR1 domain, an SRCR2 domain, and an SRCR3 domain, is formed by tandemly linking a first domain consisting of one of the amino acid sequence of the SRCR1 domain and an amino acid sequence having deletion, substitution, or addition of one or more amino acids in the amino acid sequence of the SRCR1 domain and having 80% or more homology to the amino acid sequence of the SRCR1 domain, a second domain consisting of one of the amino acid sequence of the SRCR2 domain and an amino acid sequence having deletion, substitution, or addition of one or more amino acids in the amino acid sequence of the SRCR2 domain and having 80% or more homology to the amino acid sequence of the SRCR2 domain, and a third domain consisting of one of the amino acid sequence of the SRCR3 domain and an amino acid sequence having deletion, substitution, or addition of one or more amino acids in the amino acid sequence of the SRCR3 domain and having 80% or more homology to the amino acid sequence of the SRCR3 domain, and has at least one of an adipogenesis inhibitory function and a lipolytic function.

In this case, the protein of the present invention may be a protein consisting of an amino acid sequence having 80% or more homology to an amino acid sequence of AIM of an animal. The protein of the present invention may be a secretory type protein. The protein of the present invention may have an apoptosis inhibitory function. The protein of the present invention may be a protein having 300 to 400, preferably 320 to 380, and more preferably 340 to 360 amino acid residues in its amino acid sequence.

In addition, at least one of the first domain, the second domain, and the third domain may be a domain consisting of an amino acid sequence having deletion, substitution, or addition of one or more amino acids in the amino acid sequence of the SRCR domain corresponding to the at least one domain and having 80% or more homology to the amino acid sequence of the corresponding SRCR domain. The first domain, the second domain, and the third domain may be sequentially linked from the N terminal side.

In this case, the animal is not particularly limited as long as the animal is an animal other than a human. The animal, for example, is a mammal such as a rodent (a mouse, a rat, a guinea pig, a rabbit etc.), a dog, a cat, a pig, a cow or bull, a horse, or a monkey. More specifically, the animal is, for example, a mouse, a dog, or a cat.

That is, for example, the amino acid sequence of AIM of an animal is the amino acid sequence shown in SEQ ID NO: 5 (amino acid sequence of mouse AIM), the amino acid sequence of the SRCR1 domain is the amino acid sequence shown in SEQ ID NO: 6, the amino acid sequence of the SRCR2 domain is the amino acid sequence shown in SEQ ID NO: 7, and the amino acid sequence of the SRCR3 domain is the amino acid sequence shown in SEQ ID NO: 8.

Likewise, the amino acid sequence of AIM of an animal may be, for example, the amino acid sequence shown in SEQ ID NO: 11 (amino acid sequence of dog AIM), the amino acid sequence shown in SEQ ID NO: 12 (amino acid sequence of chimpanzee AIM), or the amino acid sequence shown in SEQ ID NO: 13 (amino acid sequence of rat AIM).

Further, the protein of the present invention is, for example, a protein which is formed by tandemly linking a first domain consisting of one of the amino acid sequence of the above-mentioned SRCR1 domain and an amino acid sequence having deletion, substitution, or addition of one or several amino acids in the amino acid sequence of the SRCR1 domain, a second domain consisting of one of the amino acid of the above-mentioned SRCR2 domain and an amino acid sequence having deletion, substitution, or addition of one or several amino acids in the amino acid sequence of the SRCR2 domain, and a third domain consisting of one of the amino acid of the above-mentioned SRCR3 domain and an amino acid sequence having deletion, substitution, or addition of one or several amino acids in the amino acid sequence of the SRCR3 domain, and has at least one of an adipogenesis inhibitory function and a lipolytic function.

Also in this case, the animal is not particularly limited as long as the animal is an animal other than a human. The animal, for example, is a mammal such as a rodent (a mouse, a rat, a guinea pig, a rabbit etc.), a dog, a cat, a pig, a cow or bull, a horse, or a monkey. More specifically, the animal is, for example, a mouse, a dog, or a cat.

That is, the protein of the present invention is, for example, a protein which is formed by tandemly linking a first domain consisting of one of the amino acid sequence shown in SEQ ID NO: 6 and an amino acid sequence having deletion, substitution, or addition of one or several amino acids in the amino acid sequence shown in SEQ ID NO: 6, a second domain consisting of one of the amino acid sequence shown in SEQ ID NO: 7 and an amino acid sequence having deletion, substitution, or addition of one or several amino acids in the amino acid sequence shown in SEQ ID NO: 7, and a third domain consisting of one of the amino acid sequence shown in SEQ ID NO: 8 and an amino acid sequence having deletion, substitution, or addition of one or several amino acids in the amino acid sequence shown in SEQ ID NO: 8, and has at least one of an adipogenesis inhibitory function and a lipolytic function.

That is, the protein of the present invention has three domains, i.e., one of the SRCR1 domain of mouse AIM and a mutated form thereof, one of the SRCR2 domain of mouse AIM and a mutated form thereof, and one of the SRCR3 domain of mouse AIM and a mutated form thereof. In this case, the protein of the present invention is also a protein consisting of an amino acid sequence having deletion, substitution, or addition of one or more amino acids in the amino acid sequence shown in SEQ ID NO: 5. That is, the protein of the present invention may be a protein consisting of an amino acid sequence having 80% or more homology to the amino acid sequence shown in SEQ ID NO: 5. The protein of the present invention may be a secretory type protein. The protein of the present invention may have an apoptosis inhibitory function. The protein of the present invention may be a protein having 300 to 400, preferably 320 to 380, and more preferably 340 to 360 amino acid residues in its amino acid sequence.

The protein of the present invention is, for example, a protein which is formed by tandemly linking a first domain consisting of the amino acid sequence of the above-mentioned SRCR1 domain, a second domain consisting of the amino acid sequence of the above-mentioned SRCR2 domain, and a third domain consisting of the amino acid sequence of the above-mentioned SRCR3 domain, and has at least one of an adipogenesis inhibitory function and a lipolytic function.

Also in this case, the animal is not particularly limited as long as the animal is an animal other than a human. The animal, for example, is a mammal such as a rodent (a mouse, a rat, a guinea pig, a rabbit etc.), a dog, a cat, a pig, a cow or bull, a horse, or a monkey. More specifically, the animal is, for example, a mouse, a dog, or a cat.

That is, the protein of the present invention is, for example, a protein which consists of an amino acid sequence having deletion, substitution, or addition of one or more amino acids in the amino acid sequence shown in SEQ ID NO: 5, is formed by tandemly linking a first domain consisting of the amino acid sequence shown in SEQ ID NO: 6 (SRCR1 domain of mouse AIM), a second domain consisting of the amino acid sequence shown in SEQ ID NO: 7 (SRCR2 domain of mouse AIM), and a third domain consisting of the amino acid sequence shown in SEQ ID NO: 8 (SRCR3 domain of mouse AIM), and has at least one of an adipogenesis inhibitory function and a lipolytic function.

That is, the protein of the present invention has three domains, i.e., the SRCR1 domain, the SRCR2 domain, and the SRCR3 domain of mouse AIM as the SRCR domains. In this case, the protein of the present invention may be a protein including an amino acid sequence having 80% or more homology to the amino acid sequence shown in SEQ ID NO: 5. That is, the protein of the present invention may be, for example, a protein consisting of an amino acid sequence having deletion, substitution, or addition of one or several amino acids in the amino acid sequence shown in SEQ ID NO: 5. The protein of the present invention may be a secretory type protein. The protein of the present invention may have an apoptosis inhibitory function. The protein of the present invention may be a protein having 300 to 400, preferably 320 to 380, and more preferably 340 to 360 amino acid residues in its amino acid sequence.

In addition, any one of the proteins of the present invention having the first domain, the second domain, and the third domain described above may be a protein which is formed by tandemly and directly linking the first domain, the second domain, and the third domain, and has at least one of an adipogenesis inhibitory function and a lipolytic function.

That is, in this case, the protein of the present invention is a protein consisting of an amino acid sequence formed by tandemly and directly linking the amino acid sequence of the first domain, the amino acid sequence of the second domain, and the amino acid sequence of the third domain. However, the protein of the present invention having the first domain, the second domain, and the third domain described above is not limited thereto, and may be a protein having a connecting portion between the domains.

The protein of the present invention is, for example, a protein which consists of an amino acid sequence having deletion, substitution, or addition of one or more amino acids in an amino acid sequence of AIM of an animal having an SRCR1 domain, an SRCR2 domain, and an SRCR3 domain, is formed by tandemly linking a first domain consisting of one of the amino acid sequence of the SRCR1 domain and an amino acid sequence having deletion, substitution, or addition of one or more amino acids in the portion other than the consensus sequence in the amino acid sequence of the SRCR1 domain, a second domain consisting of one of the amino acid sequence of the SRCR2 domain and an amino acid sequence having deletion, substitution, or addition of one or more amino acids in the portion other than the consensus sequence in the amino acid sequence of the SRCR2 domain, and a third domain consisting of one of the amino acid sequence of the SRCR3 domain and an amino acid sequence having deletion, substitution, or addition of one or more amino acids in the portion other than the consensus sequence in the amino acid sequence of the SRCR3 domain, and has at least one of an adipogenesis inhibitory function and a lipolytic function.

In this case, the protein of the present invention may be a protein consisting of an amino acid sequence having 80% or more homology to an amino acid sequence of AIM of an animal. The protein of the present invention may be a secretory type protein. The protein of the present invention may have an apoptosis inhibitory function. The protein of the present invention may be a protein having 300 to 400, preferably 320 to 380, and more preferably 340 to 360 amino acid residues in its amino acid sequence.

In addition, at least one of the first domain, the second domain, and the third domain may be a domain consisting of an amino acid sequence having deletion, substitution, or addition of one or more amino acids in the portion other than the consensus sequence in the amino acid sequence of the SRCR domain corresponding to the at least one domain. At least one of the first domain, the second domain, and the third domain may be a domain consisting of an amino acid sequence having 80% or more homology to the amino acid sequence of the SRCR domain corresponding to the at least one domain. That is, at least one of the first domain, the second domain, and the third domain may be a domain consisting of an amino acid sequence having deletion, substitution, or addition of one or several amino acids in the portion other than the consensus sequence in the amino acid sequence of the SRCR domain corresponding to the at least one domain. The first domain, the second domain, and the third domain may be linked sequentially from the N terminal side.

The animal is not particularly limited as long as the animal is an animal other than a human. The animal, for example, is a mammal such as a rodent (a mouse, a rat, a guinea pig, a rabbit etc.), a dog, a cat, a pig, a cow or bull, a horse, or a monkey. More specifically, the animal is, for example, a mouse, a dog, or a cat.

That is, the protein of the present invention is, for example, a protein which is formed by tandemly linking a first domain consisting of one of the amino acid sequence shown in SEQ ID NO: 6 and an amino acid sequence having deletion, substitution, or addition of one or more amino acids in the portion other than the consensus sequence (consensus sequence in the SRCR1 domain shown in FIG. 3) in the amino acid sequence shown in SEQ ID NO: 6, a second domain consisting of one of the amino acid sequence shown in SEQ ID NO: 7 and an amino acid sequence having deletion, substitution, or addition of one or more amino acids in the portion other than the consensus sequence (consensus sequence in the SRCR2 domain shown in FIG. 3) in the amino acid sequence shown in SEQ ID NO: 7, and a third domain consisting of one of the amino acid sequence shown in SEQ ID NO: 8 and an amino acid sequence having deletion, substitution, or addition of one or more amino acids in the portion other than the consensus sequence (consensus sequence in the SRCR3 domain shown in FIG. 3) in the amino acid sequence shown in SEQ ID NO: 8, and has at least one of an adipogenesis inhibitory function and a lipolytic function.

That is, the protein of the present invention has three domains, i.e., one of the SRCR1 domain of mouse AIM and a domain having a mutation in the portion other than the consensus sequence in the SRCR1 domain of mouse AIM, one of the SRCR2 domain of mouse AIM and a domain having a mutation in the portion other than the consensus sequence in the SRCR2 domain of mouse AIM, and one of the SRCR3 domain of mouse AIM and a domain having a mutation in the portion other than the consensus sequence in the SRCR3 domain of mouse AIM, as SRCR domains. In this case, the protein of the present invention may be a protein consisting of an amino acid sequence having 80% or more homology to the amino acid sequence shown in SEQ ID NO: 5. The protein of the present invention may be a secretory type protein. The protein of the present invention may have an apoptosis inhibitory function. The protein of the present invention may be a protein having 300 to 400, preferably 320 to 380, and more preferably 340 to 360 amino acid residues in its amino acid sequence.

Likewise, the amino acid sequence of AIM of an animal may be, for example, the amino acid sequence shown in SEQ ID NO: 11 (amino acid sequence of dog AIM), the amino acid sequence shown in SEQ ID NO: 12 (amino acid sequence of chimpanzee AIM), or the amino acid sequence shown in SEQ ID NO 13 (amino acid sequence of rat AIM).

Any one of the protein of the present inventions having the first domain, the second domain, and the third domain, which have a mutation in the portion other than the consensus sequence described above, may be a protein which is formed by tandemly and directly linking the first domain, the second domain, and the third domain, and has at least one of an adipogenesis inhibitory function and a lipolytic function.

That is, in this case, the protein of the present invention is a protein consisting of an amino acid sequence formed by tandemly and directly linking the amino acid sequence of the first domain, the amino acid sequence of the second domain, and the amino acid sequence of the third domain. However, the protein of the present invention having the first domain, the second domain, and the third domain, which have a mutation in the portion other than the consensus sequence described above is not limited thereto, and may be a protein having a connecting portion between the domains.

Further, the protein of the present invention is one of the following proteins (p1), (p2), and (p3), which has at least one of an adipogenesis inhibitory function and a lipolytic function: (p1) one of a first domain protein consisting of the amino acid sequence of an SRCR1 domain of AIM of an animal and a protein formed by tandemly linking a plurality of the first domain proteins; (p2) one of a second domain protein consisting of the amino acid sequence of an SRCR2 domain of AIM of an animal and a protein formed by tandemly linking a plurality of the second domain proteins; and (p3) one of a third domain protein consisting of the amino acid sequence of an SRCR3 domain of AIM of an animal and a protein formed by tandemly linking a plurality of the third domain proteins.

That is, in this case, the protein of the present invention is, for example, a protein consisting of an SRCR1 domain of AIM of an animal (first domain protein), or a protein formed by tandemly linking a plurality of the SRCR1 domains (protein (p1) described above). The protein of the present invention is, for example, a protein consisting of an SRCR2 domain of AIM of an animal (second domain protein), or a protein formed by tandemly linking a plurality of the SRCR2 domains (protein (p2) described above). The protein of the present invention is, for example, a protein consisting of an SRCR3 domain of AIM of an animal (third domain protein), or a protein formed by tandemly linking a plurality of the SRCR3 domains (protein (p3) described above).

The protein of the present invention is likewise, for example, one of the following proteins (q1), (q2), and (q3), which has at least one of an adipogenesis inhibitory function and a lipolytic function: (q1) one of a first domain protein consisting of an amino acid sequence having deletion, substitution, or addition of one or more amino acids in the amino acid sequence of an SRCR1 domain of AIM of an animal and having 80% or more homology to the amino acid sequence of the SRCR1 domain, and a protein formed by tandemly and directly linking a plurality of the first domain proteins; (q2) one of a second domain protein consisting of an amino acid sequence having deletion, substitution, or addition of one or more amino acids in the amino acid sequence of an SRCR2 domain of AIM of an animal and having 80% or more homology to the amino acid sequence of the SRCR2 domain, and a protein formed by tandemly and directly linking a plurality of the second domain proteins; and (q3) one of a third domain protein consisting of an amino acid sequence having deletion, substitution, or addition of one or more amino acids in the amino acid sequence of an SRCR3 domain of AIM of an animal and having 80% or more homology to the amino acid sequence of the SRCR3 domain, and a protein formed by tandemly and directly linking a plurality of the third domain proteins.

The protein of the present invention is likewise, for example, one of the following proteins (r1), (r2), and (r3), which has at least one of an adipogenesis inhibitory function and a lipolytic function: (r1) one of a first domain protein consisting of an amino acid sequence having deletion, substitution, or addition of one or more amino acids in the portion other than the consensus sequence in the amino acid sequence of an SRCR1 domain having at least one of an adipogenesis inhibitory function and a lipolytic function of an animal and a protein formed by tandemly and directly linking a plurality of the first domain proteins; (r2) one of a second domain protein consisting of an amino acid sequence having deletion, substitution, or addition of one or more amino acids in the portion other than the consensus sequence in the amino acid sequence of an SRCR2 domain having at least one of an adipogenesis inhibitory function and a lipolytic function of an animal and a protein formed by tandemly and directly linking a plurality of the second domain proteins; and (r3) one of a third domain protein consisting of an amino acid sequence having deletion, substitution, or addition of one or more amino acids in the portion other than the consensus sequence in the amino acid sequence of an SRCR3 domain having at least one of an adipogenesis inhibitory function and a lipolytic function of an animal and a protein formed by tandemly and directly linking a plurality of the third domain proteins.

Any one of the protein of the present inventions having the first domain protein, the second domain protein, or the third domain protein described above may be a protein formed by tandemly and directly linking a plurality of the first domain proteins, the second domain proteins, or the third domain proteins. However, the protein of the present invention is not limited thereto, and may be a protein having a connecting portion between the domains.

In those cases, the animal is not particularly limited as long as the animal is an animal other than a human. The animal, for example, is a mammal such as a rodent (a mouse, a rat, a guinea pig, a rabbit etc.), a dog, a cat, a pig, a cow or bull, a horse, or a monkey. More specifically, the animal is, for example, a mouse, a dog, or a cat.

That is, for example, when AIM of an animal is mouse AIM, the amino acid sequence of the SRCR1 domain is the amino acid sequence shown in SEQ ID NO: 6, the amino acid sequence of the SRCR2 domain is the amino acid sequence shown in SEQ ID NO: 7, and the amino acid sequence of the SRCR3 domain is the amino acid sequence shown in SEQ ID NO: 8.

Likewise, the amino acid sequence of AIM of an animal may be the amino acid sequence shown in SEQ ID NO: 11 (amino acid sequence of dog AIM), the amino acid sequence shown in SEQ ID NO: 12 (amino acid sequence of chimpanzee AIM), or the amino acid sequence shown in SEQ ID NO: 13 (amino acid sequence of rat AIM).

The pharmaceutical composition of the present invention contains at least one of the above-mentioned proteins of the present invention as an active ingredient. The pharmaceutical composition of the present invention may further contain a pharmaceutically acceptable carrier. The pharmaceutically acceptable carrier is not particularly limited, and those which may be used for so-called protein preparations, for example, antibody drug may be preferably used. Specifically, for example, one kind or two or more kinds of excipients, solvents, diluents, dispersants, emulsifiers, dissolution aids, suspending agents, stabilizers, tonicity agents, buffers, pH adjusters, soothing agents, preservatives, and antioxidants may be used.

A dosage form of the pharmaceutical composition of the present invention is not particularly limited, and, for example, may be made into an injection, tablet, pill, capsule, powder, granule, solution, or syrup. That is, the pharmaceutical composition of the present invention, for example, may be made into local injection to be injected into tissues in a living body, intravenous injection, intraarterial injection, and infusion drugs to be injected into blood, and injection drugs to be injected intraperitoneally.

When the pharmaceutical composition of the present invention is a local injection, the pharmaceutical composition of the present invention may be made into, for example, an adipose tissue injection to be directly injected into adipose tissues such as visceral adipose tissues and subcutaneous adipose tissues, a subcutaneous injection, and an intramuscular injection.

Further, when the pharmaceutical composition of the present invention is an injection, the pharmaceutical composition of the present invention may be made into a powder prepared by drying a solution containing the protein of the present invention and the above-mentioned pharmaceutically acceptable carriers by a method such as lyophilization, and aseptically stored in a container such as an ampule. It should be noted that it has been confirmed by the inventors of the present invention that the functions of AIM are not lost by such drying and redissolution.

Also, when the pharmaceutical composition of the present invention is administered, the powder is dissolved in an appropriate solvent such as physiological saline, Ringer solution, or other solutions for injection to prepare the pharmaceutical composition of the present invention consisting of a liquid injection containing the protein of the present invention as an active ingredient. When the pharmaceutical composition of the present invention is an injection, for example, a solution containing the protein of the present invention and the above-mentioned pharmaceutically acceptable carriers may be directly stored aseptically in a container such as an ampule.

A content of the protein of the present invention in the pharmaceutical composition of the present invention is appropriately determined depending on the dosage form, dosage amount, and the like, and for example, the pharmaceutical composition of the present invention may be a liquid injection containing the protein of the present invention in an amount of 0.1 to 10% by weight.

The pharmaceutical composition of the present invention is used for the diagnosis, treatment, or prevention of diseases in a human or an animal. The animal is not particularly limited as long as the animal is an animal other than a human. The animal is preferably an animal that expresses wild-type AIM and has adipocytes expressing CD36. Specifically, the animal is a mammal such as a rodent (a mouse, a rat, a guinea pig, a rabbit etc.), a dog, a cat, a pig, a cow or bull, a horse, or a monkey. More specifically, the animal is, for example, a mouse, a dog, or a cat. That is, the pharmaceutical composition of the present invention is used for the diagnosis, treatment, or prevention of diseases in a human or a mammal other than a human such as a rodent (a mouse, a rat, a guinea pig, a rabbit etc.), a dog, a cat, a pig, a cow or bull, a horse, or a monkey, and more specifically is used or the diagnosis, treatment, or prevention of diseases in a human, a mouse, a dog, or a cat.

That is, the pharmaceutical composition of the present invention is, for example, a pharmaceutical composition to be administered to a human (pharmaceutical composition for a human).

The pharmaceutical composition of the present invention is, for example, a pharmaceutical composition to be administered to an animal (pharmaceutical composition for an animal). The animal is not particularly limited as long as the animal is an animal other than a human. The animal is preferably an animal that expresses wild-type AIM and has adipocytes expressing CD36. Specifically, the animal is a mammal such as a rodent (a mouse, a rat, a guinea pig, a rabbit etc.), a dog, a cat, a pig, a cow or bull, a horse, or a monkey. More specifically, the animal is, for example, a mouse, a dog, or a cat. That is, the pharmaceutical composition of the present invention is, for example, a pharmaceutical composition to be administered to a human or a mammal other than a human such as a rodent (a mouse, a rat, a guinea pig, a rabbit etc.), a dog, a cat, a pig, a cow or bull, a horse, or a monkey, and more specifically is a pharmaceutical composition to be administered to a human, a mouse, a dog, or a cat.

It should be noted that target diseases to which the pharmaceutical composition of the present invention is applied should be broadly interpreted, and include all states having some structural or functional defects in a living body. That is, the pharmaceutical composition of the present invention is a pharmaceutical composition to be administered to a living body, for example, in order to diagnose, treat or prevent metabolic disorders, fatty neoplasm (tumor), and degenerative disorders (including nerves). Those disease areas include, for example, diabetes, obesity, hypertension, cardiovascular diseases including arteriosclerosis, and lipoma.

More specifically, the pharmaceutical composition of the present invention is used for the diagnosis, treatment, or prevention of defects associated with the adipose tissue. Examples of the defects associated with the adipose tissues include obesity and liposarcoma. That is, the pharmaceutical composition of the present invention is used in order to appropriately control the amount of visceral fat and/or subcutaneous fat for the purpose of solving or preventing defects caused in association with obesity. The pharmaceutical composition of the present invention is used for reducing liposarcoma or inhibiting the growth of liposarcoma. The pharmaceutical composition of the present invention may be used for the procedure in cosmetic surgery and plastic surgery for the purpose of controlling the adipose tissue mass at a desired site which is visible outwardly. That is, the pharmaceutical composition of the present invention is administered to a living body for the purpose of decreasing the adipose tissues, inhibiting the growth of the adipose tissues, and reducing the growth level of the adipose tissues.

One of the methods according to embodiments of the present invention (hereinafter referred to as "methods of the present invention") is, for example, a method of administering an effective amount of the protein of the present invention to a living body. That is, the method of the present invention is a method of administering the above-mentioned pharmaceutical composition of the present invention to a living body.

Here, the living body is, for example, a human. The living body is, for example, an animal. The animal is not particularly limited as long as the animal is an animal other than a human. The animal is preferably an animal that expresses wild-type AIM and has adipocytes expressing CD36. Specifically, the animal is a mammal such as a rodent (a mouse, a rat, a guinea pig, a rabbit etc.), a dog, a cat, a pig, a cow or bull, a horse, or a monkey. More specifically, the animal is, for example, a mouse, a dog, or a cat.

The method of the present invention is, for example, a method of administering the protein of the present invention (i.e., the pharmaceutical composition of the present invention), in order to diagnose, treat, or prevent diseases in a human or a mammal other than a human, in an effective amount for the diagnosis, treatment, or prevention to the human or the mammal other than a human.

The method of administering the protein of the present invention is not particularly limited, and includes, for example, a local administration by a local injection etc., an intravascular administration by an intravenous injection, an intraarterial injection, or an infusion etc., and an oral administration.

When the protein of the present invention is locally administered, for example, the pharmaceutical composition of the present invention is prepared as an injection and the injection is injected into a tissue in a living body by using an instrument for local administration, such as a syringe. That is, for example, the pharmaceutical composition of the present invention is directly injected into the adipose tissues such as the visceral adipose tissue and the subcutaneous adipose tissue for the purpose of decreasing or preventing obesity, or for cosmetic surgery. The pharmaceutical composition of the present invention is, for example, locally injected in the liposarcoma tissue in patients with liposarcoma.

When the protein of the present invention is intravascularly administered, the pharmaceutical composition of the present invention is prepared as an injection, and the injection is injected into a blood vessel in a living body by using an instrument for intravascular administration, such as a syringe and an instrument for infusion. When the protein of the present invention is orally administered, the pharmaceutical composition of the present invention is prepared as an orally administered agent such as a tablet, a pill, a capsule, a powder, a granule, a solution, or a syrup, and a patient takes the orally administered agent. It should be noted that AIM is stable in its molecular structure and does not lose its functions even under an acidic condition at a pH of about 2 to 3.

The administration of the protein of the present invention to a living body as described above effectively decreases the adipose tissue mass, inhibits the growth of the adipose tissues, or reduces the growth level of the adipose tissues, in the living body. Of those, the administration of the protein of the present invention by the injection, particularly the local administration of the protein of the present invention into the adipose tissues, more effectively decreases the adipose tissue mass, inhibits the growth of the adipose tissues, or reduces the growth level of the adipose tissue.

The dosage amount of the protein of the present invention is appropriately determined depending on conditions such as a symptom, an age, and a body weight of a subject to be administered, and one dosage amount may be, for example, 0.1 to 5 mg per kg of the body weight. It should be noted that the dosage amount of the protein of the present invention is not limited thereto as long as the dosage amount is within the effective range for decreasing the adipose tissue mass, inhibiting the growth of the adipose tissues, or reducing the growth level of the adipose tissues in a living body as a subject to be administered. That is, for example, the dosage amount in a local administration may be reduced compared to that of a systemic administration such as an intravascular administration because the protein of the present invention is efficiently and specifically delivered to a site on which the protein of the present invention is intended to act.

Likewise, an administration schedule of the protein of the present invention is appropriately determined depending on conditions such as a symptom, age, and body weight of a subject to be administered, and for example, the protein of the present invention may be administered in multiple doses over several weeks to several months at intervals of one to several weeks.

The administration of the protein of the present invention described above induces lipolysis in mature adipocytes and inhibits the differentiation of preadipocytes to mature adipocytes in the adipose tissues, in a living body to which the protein of the present invention has been delivered. That is, the pharmaceutical composition of the present invention may be designated as a differentiation inhibitor of preadipocytes and a lipolysis inducer in mature adipocytes. The administration of the protein of the present invention provides effects of decreasing the adipose tissue mass, inhibiting the growth of the adipose tissues, reducing the growth level of the adipose tissues, in a living body, and consequently provides an effect of decreasing the body weight.

Further, the method of the present invention is not limited to the above-mentioned examples as long as the method is associated with the use of the protein of the present invention. That is, the method of the present invention is, for example, a method of using the protein of the present invention as an active ingredient of a pharmaceutical composition. The method of the present invention is also, for example, a method of producing a pharmaceutical composition containing the protein of the present invention as an active ingredient. In this case, the method of the present invention may be, for example, a method of mixing the protein of the present invention and a pharmaceutically acceptable carrier, and producing a pharmaceutical composition containing the protein of the present invention and the carrier.

Further, the protein of the present invention may be applied to a food or drink. That is, a food or drink according to an embodiment of the present invention (hereinafter referred to as "food or drink of the present invention") is a food or drink containing the protein of the present invention (i.e., (I) AIM or (II) the protein which consists of an amino acid sequence having deletion, substitution, or addition of one or more amino acids in an amino acid sequence of the AIM and having homology to the amino acid sequence of the AIM, and has at least one of an adipogenesis inhibitory function and a lipolytic function). That is, the food or drink of the present invention is, for example, food containing the protein of the present invention. The food or drink of the present invention is, for example, a drink containing the protein of the present invention.

Further, the food or drink of the present invention is, for example, a composition for oral ingestion containing the protein of the present invention. The composition for oral ingestion is a composition for a consumer to ingest not as a pharmaceutical product but to supplementarily ingest similarly to a supplement such as a vitamin preparation, and is produced in a form of a tablet, a capsule, a granule, a jelly, or the like. The food or drink of the present invention is, for example, an additive for a food or drink containing the protein of the present invention. The additive for a food or drink is, for example, a composition used as a part of raw materials or added to the raw materials in a step of producing the food or drink.

Further, with respect to the food or drink of the present invention, the method of the present invention is, for example, a method of using the protein of the present invention as a part of raw materials of the food or drink. The method of the present invention is a method of producing a food or drink containing the protein of the present invention. In this case, the method of the present invention may be, for example, a method of mixing the protein of the present invention and other raw materials, and producing a food or drink containing the protein of the present invention and the other raw materials.

Here, one aspect of the present invention is described. A pharmaceutical composition according to one embodiment of the present invention is a pharmaceutical composition containing, as an active ingredient, one or more of the following proteins (a) to (l): (a) a protein consisting of the amino acid sequence shown in SEQ ID NO: 1; (b) a protein consisting of the amino acid sequence shown in SEQ ID NO: 5; (c) a protein which consists of an amino acid sequence having deletion, substitution, or addition of one or several amino acids in the amino acid sequence shown in SEQ ID NO: 1, and has a function of inhibiting the differentiation of preadipocytes to mature adipocytes and/or a function of inducing lipolysis in the mature adipocytes; (d) a protein which consists of an amino acid sequence having deletion, substitution, or addition of one or several amino acids in the amino acid sequence shown in SEQ ID NO: 5, and has a function of inhibiting the differentiation of preadipocytes to mature adipocytes and/or a function of inducing lipolysis in the mature adipocytes; (e) a protein which consists of an amino acid sequence having deletion, substitution, or addition of one or more amino acids in the amino acid sequence shown in SEQ ID NO: 1 and having 80% or more homology to the amino acid sequence shown in SEQ ID NO: 1, and has a function of inhibiting the differentiation of preadipocytes to mature adipocytes and/or a function of inducing lipolysis in the mature adipocytes; (f) a protein which consists of an amino acid sequence having deletion, substitution, or addition of one or more amino acids in the amino acid sequence shown in SEQ ID NO: 5 and having 80% or more homology to the amino acid sequence shown in SEQ ID NO: 5, and has a function of inhibiting the differentiation of preadipocytes to mature adipocytes and/or a function of inducing lipolysis in the mature adipocytes; (g) a protein which is formed by tandemly linking a first domain consisting of the amino acid sequence shown in SEQ ID NO: 2, a second domain consisting of the amino acid sequence shown in SEQ ID NO: 3, and a third domain consisting of the amino acid sequence shown in SEQ ID NO: 4, and has a function of inhibiting the differentiation of preadipocytes to mature adipocytes and/or a function of inducing lipolysis in the mature adipocytes; (h) a protein which is formed by tandemly linking a first domain consisting of the amino acid sequence shown in SEQ ID NO: 6, a second domain consisting of the amino acid sequence shown in SEQ ID NO: 7, and a third domain consisting of the amino acid sequence shown in SEQ ID NO: 8, and has a function of inhibiting the differentiation of preadipocytes to mature adipocytes and/or a function of inducing lipolysis in the mature adipocytes; (i) a protein which is formed by tandemly linking a first domain consisting of one of the amino acid sequence shown in SEQ ID NO: 2 and an amino acid sequence having deletion, substitution, or addition of one or several amino acids in the amino acid sequence shown in SEQ ID NO: 2, a second domain consisting of one of the amino acid sequence shown in SEQ ID NO: 3 and an amino acid sequence having deletion, substitution, or addition of one or several amino acids in the amino acid sequence shown in SEQ ID NO: 3, and a third domain consisting of one of the amino acid sequence shown in SEQ ID NO: 4 and an amino acid sequence having deletion, substitution, or addition of one or several amino acids in the amino acid sequence shown in SEQ ID NO: 4, and has a function of inhibiting the differentiation of preadipocytes to mature adipocytes and/or a function of inducing lipolysis in the mature adipocytes; (j) a protein which is formed by tandemly linking a first domain consisting of one of the amino acid sequence shown in SEQ ID NO: 6 and an amino acid sequence having deletion, substitution, or addition of one or several amino acids in the amino acid sequence shown in SEQ ID NO: 6, a second domain consisting of one of the amino acid sequence shown in SEQ ID NO: 7 and an amino acid sequence having deletion, substitution, or addition of one or several amino acids in the amino acid sequence shown in SEQ ID NO: 7, and a third domain consisting of one of the amino acid sequence shown in SEQ ID NO: 8 and an amino acid sequence having deletion, substitution, or addition of one or several amino acids in the amino acid sequence shown in SEQ ID NO: 8, and has a function of inhibiting the differentiation of preadipocytes to mature adipocytes and/or a function of inducing lipolysis in the mature adipocytes; (k) a protein which is formed by tandemly linking a first domain consisting of one of the amino acid sequence shown in SEQ ID NO: 2 and an amino acid sequence having deletion, substitution, or addition of one or more amino acids in a portion other than a consensus sequence in the amino acid sequence shown in SEQ ID NO: 2, a second domain consisting of one of the amino acid sequence shown in SEQ ID NO: 3 and an amino acid sequence having deletion, substitution, or addition of one or more amino acids in a portion other than a consensus sequence in the amino acid sequence shown in SEQ ID NO: 3, and a third domain consisting of one of the amino acid sequence shown in SEQ ID NO: 4 and an amino acid sequence having deletion, substitution, or addition of one or more amino acids in a portion other than a consensus sequence in the amino acid sequence shown in SEQ ID NO: 4, and has a function of inhibiting the differentiation of preadipocytes to mature adipocytes and/or a function of inducing lipolysis in the mature adipocytes; and (l) a protein which is formed by tandemly linking a first domain consisting of one of the amino acid sequence shown in SEQ ID NO: 6 and an amino acid sequence having deletion, substitution, or addition of one or more amino acids in a portion other than a consensus sequence in the amino acid sequence shown in SEQ ID NO: 6, a second domain consisting of one of the amino acid sequence shown in SEQ ID NO: 7 and an amino acid sequence having deletion, substitution, or addition of one or more amino acids at the portion other than a consensus sequence in the amino acid sequence shown in SEQ ID NO: 7, and a third domain consisting of one of the amino acid sequence shown in SEQ ID NO: 8 and an amino acid sequence having deletion, substitution, or addition of one or more amino acids in a portion other than a consensus sequence in the amino acid sequence shown in SEQ ID NO: 8, and has a function of inhibiting the differentiation of preadipocytes to mature adipocytes and/or a function of inducing lipolysis in the mature adipocytes.

A method according to one embodiment of the present invention includes administering the above-mentioned pharmaceutical composition to a living body. A method according to one embodiment of the present invention includes administering an effective amount of at least one of the above-mentioned proteins (a) to (l) to a living body. A method according to one embodiment of the present invention includes using at least one of the above-mentioned proteins (a) to (l) as an active ingredient of a pharmaceutical composition. A method according to one embodiment of the present invention includes producing a pharmaceutical composition containing at least one of the above-mentioned proteins (a) to (l) as an active ingredient. A food or drink according to one embodiment of the present invention includes containing at least one of the above-mentioned proteins (a) to (l). A method according to one embodiment of the present invention includes producing a food or drink containing at least one of the above-mentioned proteins (a) to (l).

Subsequently, specific examples according to embodiments of the present invention are described.

EXAMPLES

Example 1

Expression of AIM by Macrophages in Adipose Tissue

A high fat diet (HFD, fat calorie 60%) was given to C57BL/6 mice for 20 weeks. Likewise, HFD was also given to adiponectin-knockout mice (Adipo$^{-/-}$ mice) which were more obese. Subsequently, intraabdominal visceral adipose tissues were collected from those mice. Paraffin sections made from this adipose tissue were double-stained with an anti-macrophage monoclonal antibody (F4/80) and anti-mouse AIM polyclonal antibody (SA-1).

Figure 4:
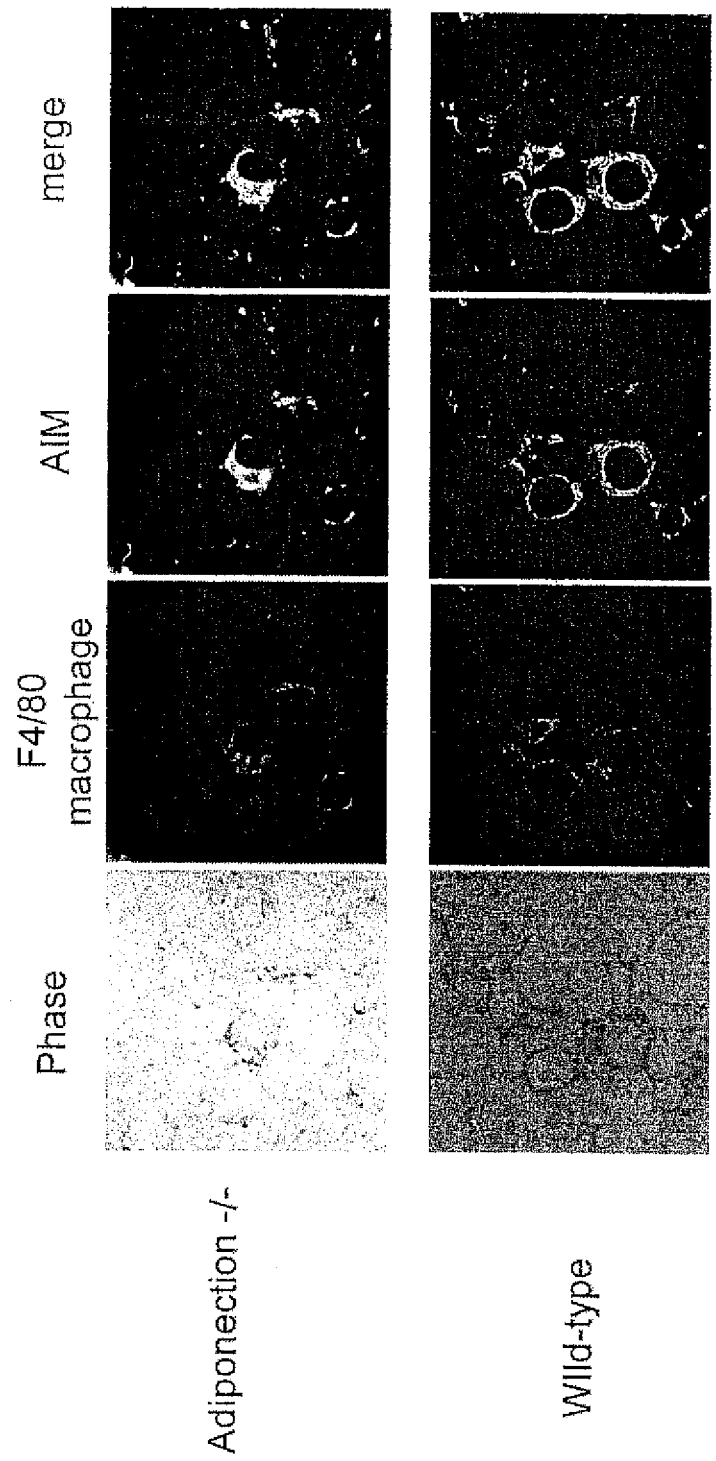
FIG. 4 is an explanatory diagram showing examples of micrographs showing that macrophages infiltrating adipose tissues produce AIM.

FIG. 4 shows an example of the results of observing the stained sections under a phase contrast microscope and a fluorescent microscope. In FIG. 4, photos under the phase contrast microscope (Phase), photos of stained macrophages under the fluorescent microscope (F4/80 macrophage), photos of stained AIM under the fluorescent microscope (AIM), and photos obtained by merging those fluorescence micrographs (merge) are shown for wild-type C57BL/6 mice (Wild-type) and Adipo$^{-/-}$ mice (Adiponectin-/-).

As shown in FIG. 4, portions of the stained macrophages were overlapped with portions of the stained AIM in both the wild-type mice and the Adipo$^{-/-}$ mice, confirming that the macrophages infiltrating the adipose tissues strongly expressed AIM.

Example 2

Inhibition of Differentiation of Adipocytes by AIM

In order to examine how AIM produced by the macrophages infiltrating the adipose tissues works on surrounding adipocytes, an experiment in which AIM was loaded during a culture process of differentiating 3T3-L1 preadipocytes into the mature adipocytes was performed.

Figure 5A:
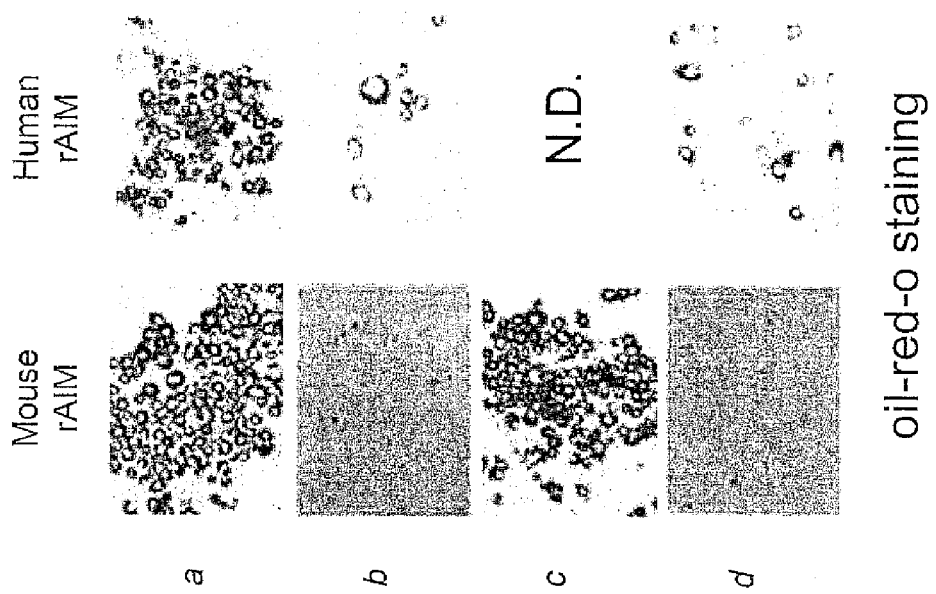
FIG. 5A is an explanatory diagram illustrating one example of a loading schedules of AIM for adipocytes.

That is, as illustrated in FIG. 5A, a culture of 3T3-L1 cells was performed in the following four mutually different schedules (a) to (d); (a) AIM was not loaded, (b) AIM was loaded for 10 days (day 2 to day 12) after the initiation of stimuli for differentiation induction, (c) AIM was loaded in a period of clonal expansion alone (day −2 to day 2) before the differentiation induction, and (d) AIM was loaded in the early phase alone (day 2 to day 4) of the stimuli for differentiation induction.

A recombinant mouse AIM protein and a recombinant human AIM protein were used as AIM. Those recombinant AIM proteins were prepared by culturing human-derived HEK293T cells transfected with a vector expressing mouse AIM or human AIM and isolating and purifying the protein from its culture supernatant. The same recombinant AIM proteins were also used as AIM in other examples shown below. AIM was loaded by adding AIM at a concentration of 5 μg/mL to the culture medium.

Differentiation induction (Induction) of the 3T3-L1 cells was initiated by first culturing the 3T3-L1 cells for 4 days (day −2 to day 2) to proliferate the cells (Cell proliferation) and subsequently culturing the cells in a culture medium containing insulin, dexamethasone (DEX), and isobutylmethylxanthine (IBMX) for 2 days (day 2 to day 4). The differentiation induction was further continued by culturing the cells in a culture medium containing insulin for 2 days (day 4 to day 6).

After the period of the differentiation induction (day 2 to day 6), the culture was continued in a culture medium not containing those differentiation-inducing factors. Then, the cells on the 10th day (day 12) after the initiation of the stimuli for differentiation induction were stained with oil-red-o, and the differentiation of the 3T3-L1 cells to mature adipocytes was observed.

Figure 5B:
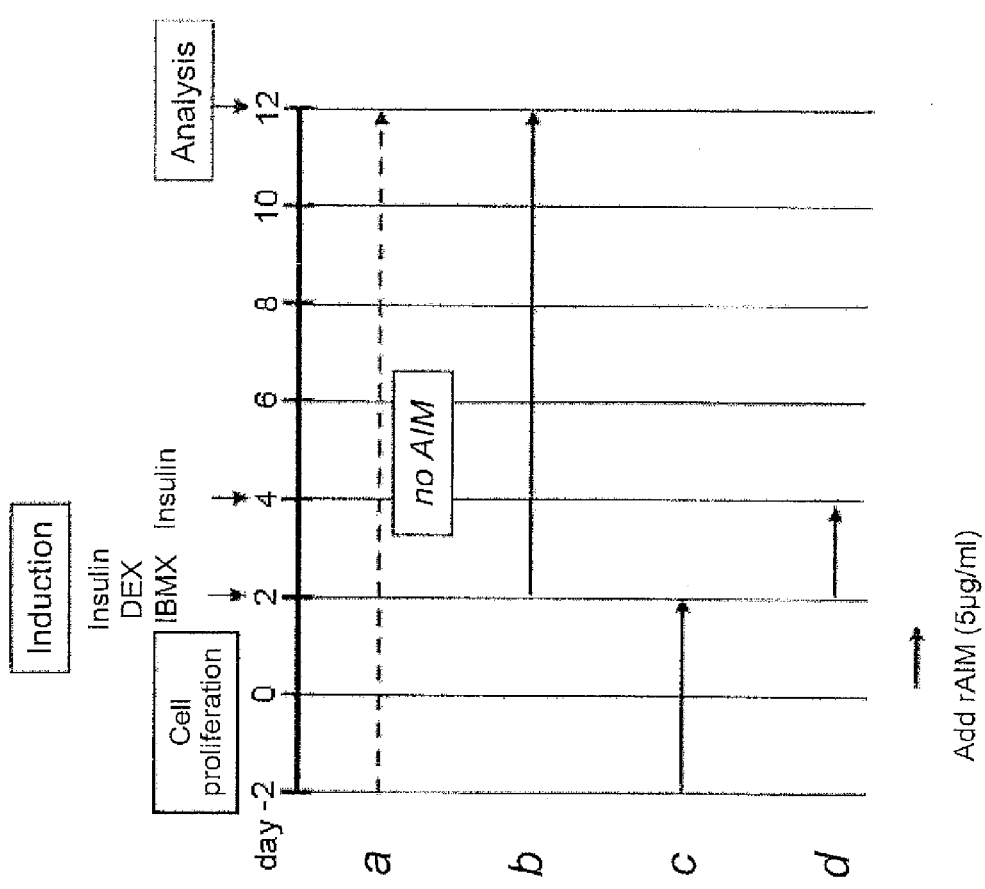
FIG. 5B is an explanatory diagram showing one example of results of loading cells with AIM according to the schedule illustrated in FIG. 5A, and then staining fats in the cells with oil-red-o.

FIG. 5B shows micrographs of the stained cells obtained in the experiments in which mouse AIM (Mouse rAIM) or human AIM (Human rAIM) was loaded in each of the four schedules (a) to (d) (note, however, that no AIM was loaded according to the schedule (a)). No micrograph was taken for the experiment using human AIM according to the schedule (c) (N.D.).

As shown in FIG. 5B, cells having lipid droplets were scarcely observed and the differentiation of the 3T3-L1 cell was almost completely inhibited when AIM was loaded in the early phase alone (day 2 to day 4) of the stimuli for differentiation induction according to the schedule (d). That is, AIM inhibited the differentiation of the 3T3-L1 cells in the presence of the above-mentioned differentiation-inducing factors.

Even when a culture medium containing differentiation-inducing factors and AIM was prepared and subsequently AIM was removed from the culture medium using a purification column, an ability of the differentiation-inducing factors to differentiate the 3T3-L1 cells was not lost (data not shown). Therefore, it was thought that the differentiation-inducing factors were not substantially chemically interacting with AIM.

Cells having lipid droplets were also scarcely observed and the differentiation of the 3T3-L1 cells was almost completely inhibited when AIM was loaded for 10 days (day 2 to day 12) after the initiation of the stimuli for differentiation induction according to the schedule (b). This differentiation inhibitory effect by AIM was confirmed to be dependent on the concentration of AIM (data not shown). That is, when the concentration of AIM loaded to the 3T3-L1 cells was reduced to 1 µg/mL and 0.1 µg/mL, the differentiation inhibitory effect by AIM was also reduced.

An increase of the number of dead cells due to the loading of AIM was not observed. Therefore, it was considered that the differentiation inhibition by AIM was caused by reducing the number of the 3T3-L1 cells which differentiated to the mature adipocytes without inducing the cell death.

Meanwhile, when AIM was loaded only before the differentiation induction (day −2 to day 2) according to the schedule (c), it was confirmed that most cells had lipid droplets and most 3T3-L1 cells differentiated to mature adipocytes as with the case of loading no AIM according to the schedule (a). That is, even when AIM was loaded before the differentiation induction, the differentiation of the 3T3-L1 cells to the mature adipocytes was not inhibited. In this regard, however, when AIM was continuously loaded from before the differentiation induction through the differentiation induction period and thereafter (day −2 to day 12), the differentiation of the 3T3-L1 cells to the mature adipocytes was completely inhibited (data not shown).

Here, the homology between the amino acid sequences of mouse AIM and human AIM is about 68%, which is high. The consensus sequences (amino acid sequences also conserved in other molecules having a SRCR domain such as CD5 and CD6) in the SRCR domains are completely identical in mouse AIM and human AIM as shown in FIG. 3. Also as described above, human AIM also inhibited the differentiation of 3T3-L1 cells derived from mice as was the case with mouse AIM. That is, the function of AIM was interchangeable between mouse and human.

Example 3

Induction of Lipolysis by AIM

The effect of AIM on mature adipocytes was examined. As illustrated in FIG. 6A, as was the case with above Example 2, 3T3-L1 cells were cultured while loading mouse AIM for 6 days (day 6 to day 12) after the 3T3-L1 cells differentiated and lipid droplets were formed in the cells as a schedule (e).

Then, the cells on the 10th day (day 12) after the initiation of the stimuli for differentiation induction were stained with oil-red-o. The number of cells having lipid droplets was counted. Further, the diameter of lipid droplets was measured in the cells having lipid droplets. For comparison, the number of the cells was counted and the diameter of lipid droplets was measured for the cells cultured in the above-mentioned schedules (a) and (d).

Further, the supernatant of the culture medium after the cells were cultured while loading AIM according to the schedule (e) was collected, and amounts of glycerol and free fatty acid (FFA) contained in the supernatant were measured by ELISA. For the comparison, the amounts of glycerol and free fatty acid in the culture supernatant obtained according to the schedule (a) were also measured.

In order to avoid adsorption of free fatty acid to albumin contained in the culture medium, the culture medium supplemented with 10% FBS (fetal bovine serum) was exchanged to a serum-free culture medium on the 10th day (day 12) after the initiation of the differentiation induction, further the cells were cultured in the serum-free culture medium for 6 hours, and subsequently the amounts of glycerol and free fatty acid contained in the supernatant of the serum-free culture medium were measured.

Figure 6B:
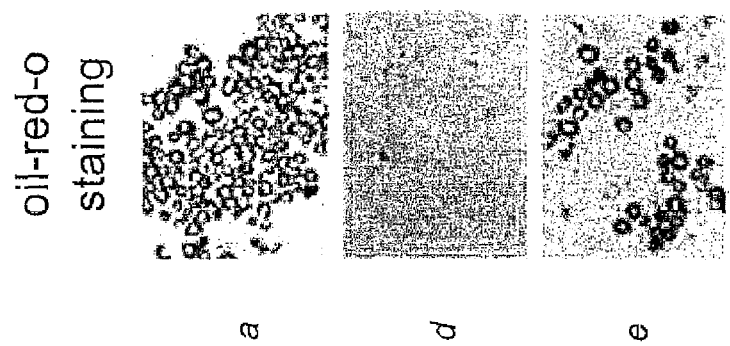
FIG. 6B is an explanatory diagram showing one example of results of loading cells with AIM according to the schedule illustrated in FIG. 6A, and then staining fats in the cells with oil-red-o.
Figure 6A:
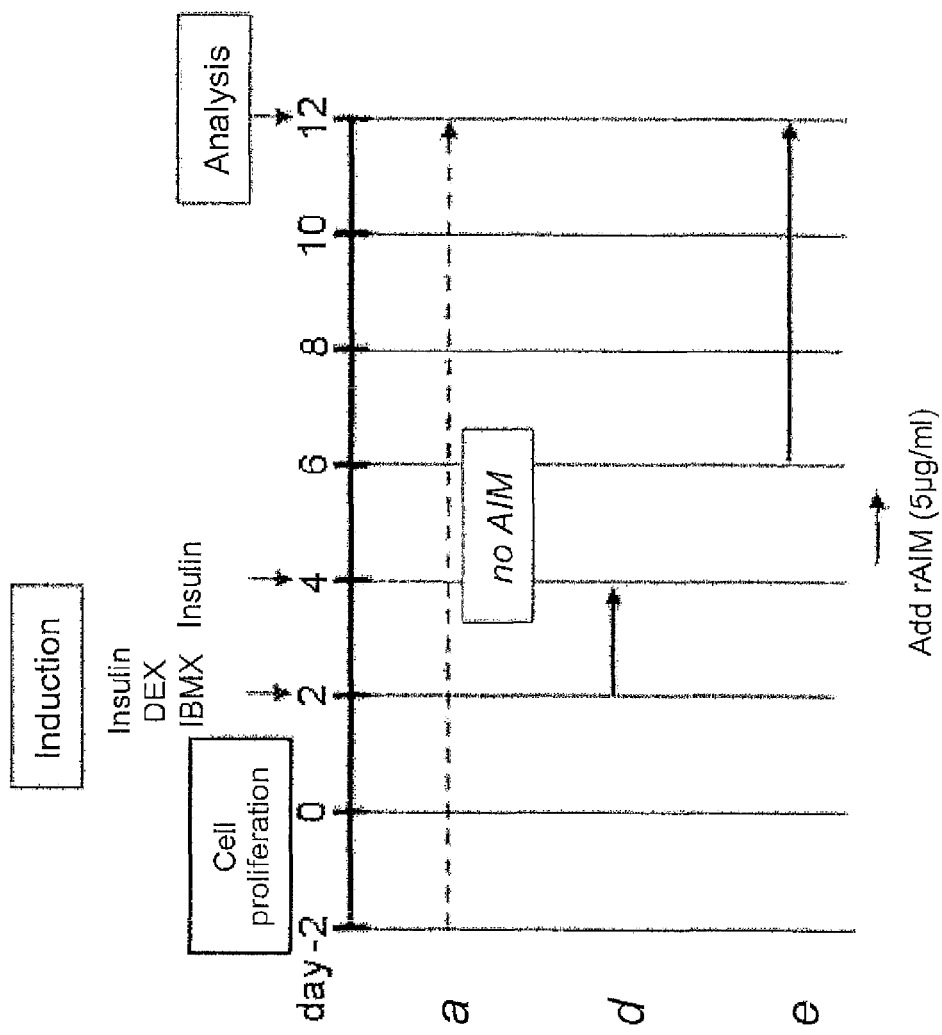
FIG. 6A is an explanatory diagram illustrating one example of loading schedules of AIM for adipocytes.
Figure 7:
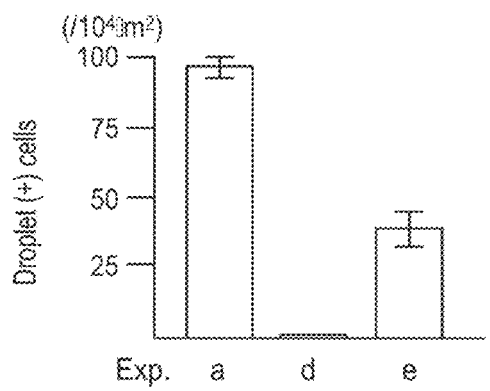
FIG. 7A is an explanatory diagram illustrating one example of results of measuring the number of cells having lipid droplets obtained when AIM was loaded according to the schedule illustrated in FIG. 6A.
FIG. 7B is an explanatory diagram illustrating one example of results of measuring the diameter of lipid droplets in the cells having lipid droplets obtained when AIM was loaded according to the schedule illustrated in FIG. 6A.
Figure 7:
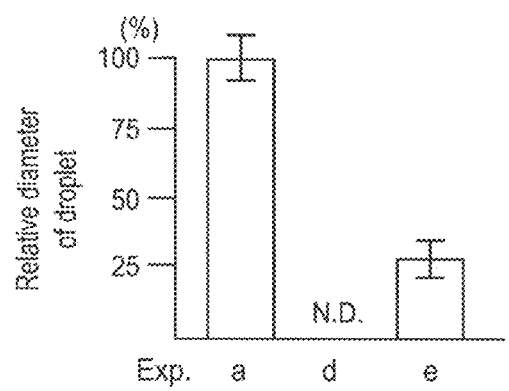
Figure 8:
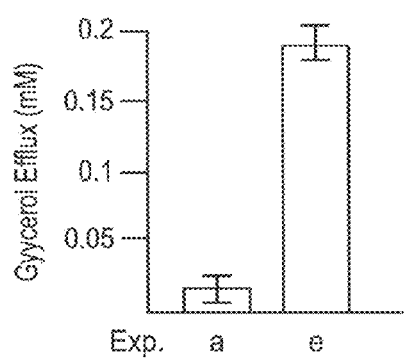
FIG. 8A is an explanatory diagram illustrating one example of results of measuring the amount of glycerol released in the culture supernatant when AIM was loaded according to the schedule illustrated in FIG. 6A.
FIG. 8B is an explanatory diagram illustrating one example of results of measuring the amount of free fatty acid released in the culture supernatant when AIM was loaded according to the schedule illustrated in FIG. 6A.
Figure 8:
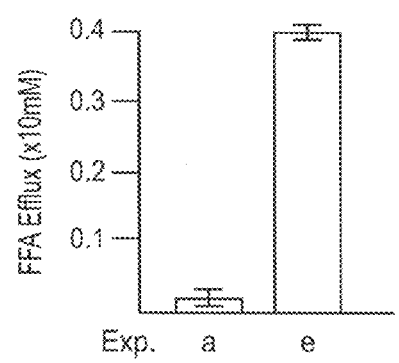

FIG. 6B shows micrographs of the cells fat-stained with oil-red-o. FIG. 7A and FIG. 7B illustrate the evaluation results of the number (per $10^4$ µm$^2$) of cells having lipid droplets (Droplet (+) cells) and the relative diameter of lipid droplets (%) obtained according to the schedules (a), (d), and (e) (Exp. a, d, and e), respectively. The relative diameter of lipid droplets illustrated in FIG. 7B was calculated by defining the diameter of lipid droplets in the cells obtained according to the schedule (a) without AIM loading as 100%. FIG. 8A and FIG. 8B illustrate the concentration of glycerol (Glycerol Efflux, mM) and the concentration of free fatty acid (FFA Efflux, ×10 mM) in the culture medium obtained according to the schedules (a) and (e) (Exp. a and e), respectively.

As shown in FIG. 6B and illustrated in FIG. 7A, the number of the cells having lipid droplets when the adipocytes after the differentiation were loaded with AIM and their culture was continued according to the schedule (e) was remarkably decreased compared with those when the adipocytes after the differentiation were cultured without AIM loading according to the schedule (a).

In addition, as illustrated in FIG. 7B, the diameter of lipid droplets contained in adipocytes obtained according to the schedule (e) was reduced to about 25% compared with that of the cells obtained according to the schedule (a):

In addition, as illustrated in FIG. 8A and FIG. 8B, both the concentration of glycerol and the concentration of free fatty acid in the culture supernatant when AIM was loaded according to the schedule (e) were remarkably increased compared with those when AIM was not loaded according to the schedule (a).

Further, when AIM was loaded according to the schedule (e), it was observed that the viscosity of the culture medium was rapidly increased after AIM was loaded. This observation result supported the fact that the amounts of glycerol and free fatty acid had been remarkably increased in the culture medium.

As described above, it was confirmed that AIM induced lipolysis in mature adipocytes. From the above-mentioned results, it was confirmed that AIM not only inhibited the differentiation and maturation of preadipocytes but also induced lipolysis in mature adipocytes to exert a "function of slimming down" the mature adipocytes.

Example 4

Control by AIM of Expression of Gene Group Associated with Adipocyte Differentiation The cells cultured in the above-mentioned five schedules (a) to (e) in Examples 2 and 3 above were collected on the 10th day (day 12) after the initiation of the stimuli for differentiation induction, and the expression of genes associated with adipose differentiation was analyzed using quantitative RT-PCR (QPCR).

Figure 9:
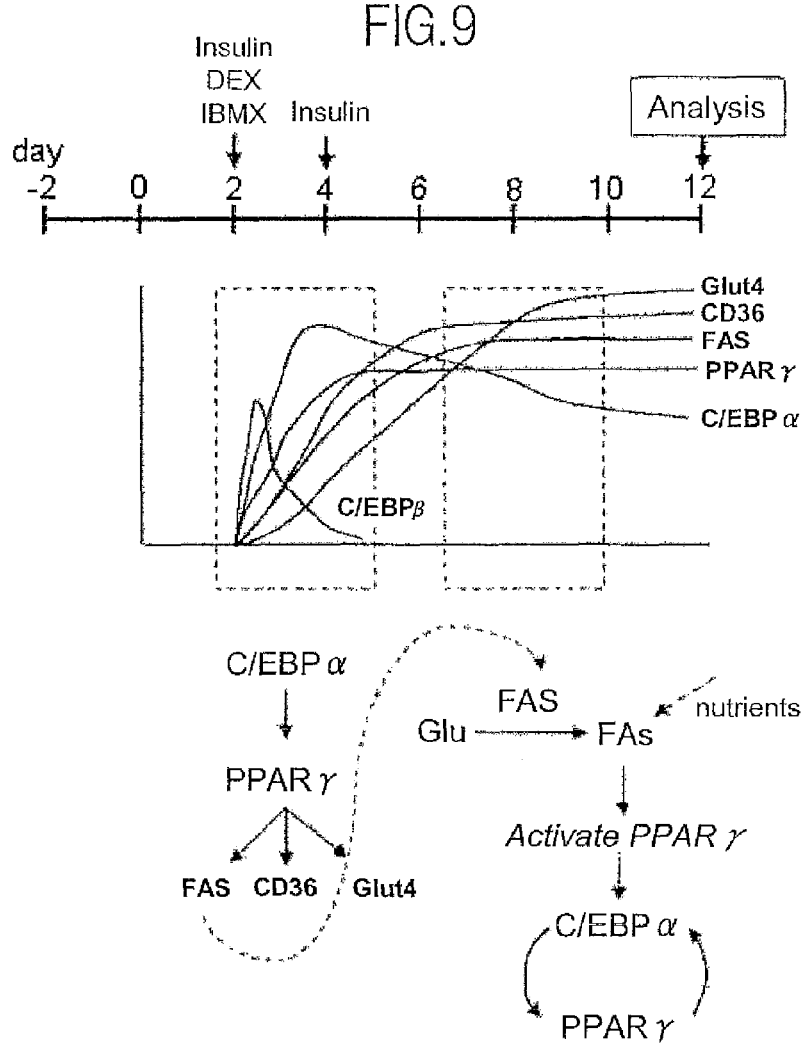
FIG. 9 is an explanatory diagram schematically illustrating expression patterns of major genes associated with the differentiation of adipocytes.

Here, FIG. 9 illustrates expression manners of the major genes associated with differentiation of adipocytes. As illustrated in a left dotted line box in FIG. 9, the expression of C/EBPβ is transiently induced by the stimuli for differentiation induction in a differentiation induction phase, thereby increasing the expression of C/EBPα and then PPARγ. Further, PPARγ induces the expression of functional genes such as a fatty acid synthase (FAS) gene, a CD36 gene, and a glucose transporter 4 (Glut4) gene which are necessary for differentiated adipocyte.

Subsequently, when the expression of the genes downstream of the C/EBPα gene is increased to some extent, as illustrated in a right dotted line box in FIG. 9, fatty acids (FAs) produced by FAS activates a PPARγ protein, and this keeps the expression of the C/EBPα gene at a certain level. The C/EBPα gene further induces the expression of the PPARγ gene. By such an alternate stimulation, a mechanism of keeping the expression levels of the PPARγ and C/EBPα genes is established even when the expression of C/EBPβ is decreased (see the right dotted line box in FIG. 9).

Figure 10:
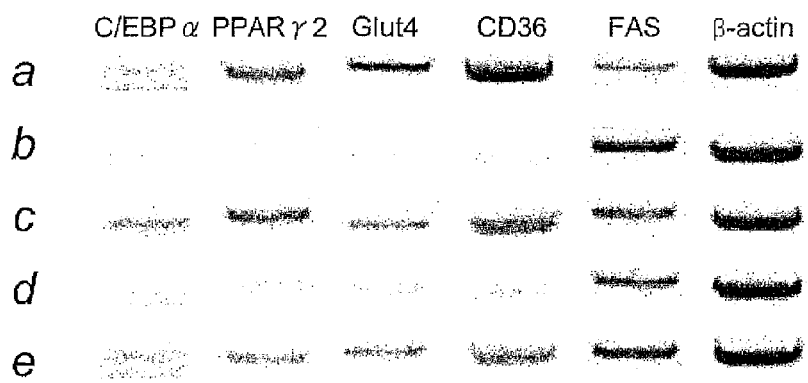
FIG. 10 is an explanatory diagram showing examples of results of analyzing the expression of genes in the cells loaded with AIM according to the schedules illustrated in FIG. 5A and FIG. 6A.

FIG. 10 shows the results of analyzing the gene expression in the cells cultured in the five schedules (a) to (e). As shown in FIG. 10, the expressions of the C/EBPα, PPARγ, CD36, and Glut4 genes were almost completely inhibited when AIM (mouse AIM, hereinafter the same AIM applies in Example 4) was loaded in the early phase alone (day 2 to day 4) of the stimuli for differentiation induction according to the schedule (d) and when AIM was loaded for 10 days after the initiation of the stimuli for differentiation induction (day 2 to day 12) according to the schedule (b) Interestingly, the expression of only the FAS gene was slightly increased in those cases.

Meanwhile, compared with the case of loading no AIM according to the schedule (a), the gene expression patterns were not changed when AIM was loaded only before the differentiation induction (day −2 to day 2) according to the schedule (c) and when AIM was loaded only after the differentiation induction (day 6 to day 12) according to the schedule (e). As described above, the expression of the genes other than the FAS gene was controlled by loading AIM in accord with the results of the morphological changes in the cells in above-mentioned Example 2.

Example 5

Inhibition of FAS Enzyme Activity by AIM

Figure 11A:
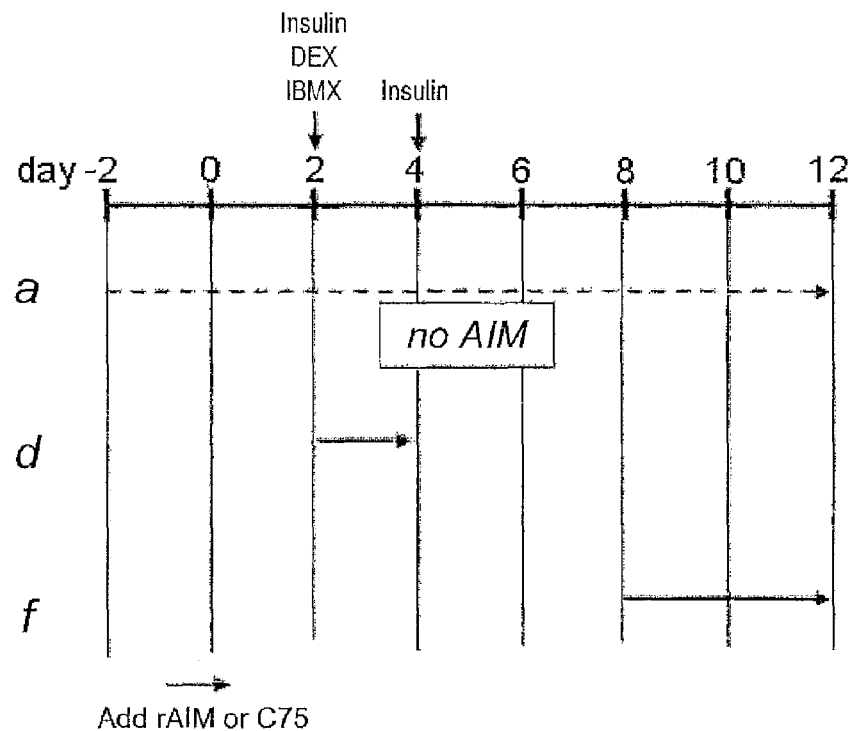
FIG. 11A is an explanatory diagram illustrating one example of loading schedules of AIM for adipocytes.

Whether AIM affected an enzyme activity of FAS or not was examined. That is, as illustrated in FIG. 11A, AIM (mouse AIM, hereinafter the same AIM applies in Example 5) was loaded to the 3T3-L1 cells in the early phase alone (day 2 to day 4) of the differentiation induction in the above-mentioned schedule (d), the cells were collected on the 2nd day (day 4) after the initiation of the differentiation induction, cell lysates were prepared, and the enzyme activity of FAS was measured.

In addition, as a schedule (f) similar to the above-mentioned schedule (e), AIM was loaded for 4 days (day 8 to day 12) after the 3T3-L1 cells differentiated, subsequently the cells were collected on the 10th day (day 12) after the initiation of the differentiation induction, cell lysates were prepared, and the enzyme activity of FAS was measured. The enzyme activity of FAS was measured based on a consumption amount of malonyl-CoA.

In addition, using a FAS inhibitor (C75) in place of AIM, the FAS inhibitor at a concentration of 25 μM was loaded according to the schedules (d) and (f), and as was the case with the above-mentioned AIM, the cells were collected on the 2nd day (day 4: schedule (d)) and 10th day (day 12: schedule (f)) after the initiation of the differentiation induction, and the enzyme activity of FAS was measured.

Further, for comparison, the cells cultured without loading AIM in the above-mentioned schedule (a) were also collected at times of the 2nd day (day 4) and 10th day (day 12) after the initiation of the differentiation induction, and the enzyme activity of FAS was measured.

Figure 11B:
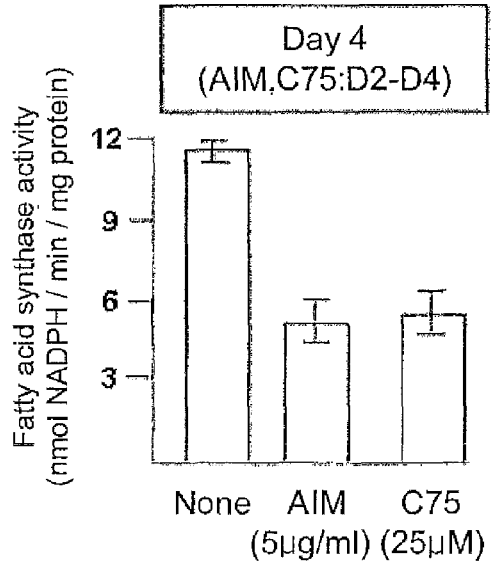
FIG. 11B is an explanatory diagram illustrating one example of results of measuring the enzyme activity of FAS in cells loaded with AIM or a FAS inhibitor according to the schedule illustrated in FIG. 11A.
Figure 11C:
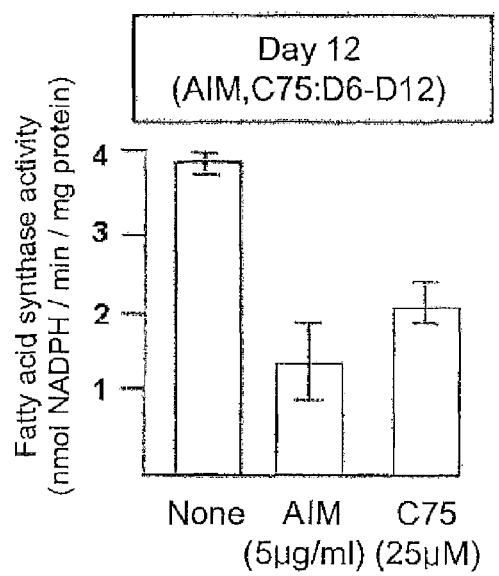
FIG. 11C is an explanatory diagram illustrating another example of results of measuring the enzyme activity of FAS in the cells loaded with AIM or the FAS inhibitor according to the schedule illustrated in FIG. 11A.

FIG. 11B and FIG. 11C illustrate the results of measuring the FAS enzyme activity (Fatty acid synthase activity) (nmol NADPH/min/mg protein). FIG. 11B illustrates the results obtained on the 2nd day (day 4) after the initiation of the differentiation induction in the case of loading no AIM according to the schedule (a) (None), the case of loading AIM according to the schedule (d) (AIM (5 μg/mL)), and the case of loading the FAS inhibitor according to the schedule (d) (C75 (25 μM)). FIG. 11C illustrates the results obtained on the 10th day (day 12) after the initiation of the differentiation induction in the case of loading no AIM according to the schedule (a) (None), the case of loading AIM according to the schedule (f) (AIM (5 μg/mL)), and the case of loading the FAS inhibitor according to the schedule (f) (C75 (25 μM)).

As illustrated in FIG. 11B and FIG. 11C, the enzyme activity of FAS was remarkably reduced in the case of loading AIM compared with the case of loading no AIM in both schedules. The levels of reduction of the FAS enzyme activity by AIM were almost the same as those in the case of loading the FAS inhibitor C75 at an effective concentration (25 μM).

FIG. 12A and FIG. 12B show the results of staining the cells with oil-red-o and analyzing the gene expression by RT-PCR on the 2nd day (day 4) after the initiation of the differentiation induction in the case of loading no AIM according to the schedule (a) (None), the case of loading AIM according to the schedule (d) (AIM (5 μg/mL)), and the case of loading the FAS inhibitor according to the schedule (d) (C75 (25 μM)), respectively.

In addition, FIG. 13A and FIG. 13B illustrate the results of measuring the glycerol concentration (glycerol efflux, mM) and the free fatty acid concentration (FFA efflux, ×10 mM) in the culture medium on the 10th day (day 12) after the initiation of the differentiation induction in the case of loading no AIM according to the schedule (a) (None), the case of loading AIM according to the schedule (f) (AIM), and the case of loading the FAS inhibitor according to the schedule (f) (C75), respectively.

As shown in FIG. 12A and FIG. 12B and illustrated in FIG. 13A and FIG. 13B, similar effects were observed on morphology of the cells, the gene expression, and extracellular release of glycerol and free fatty acid in the case of loading AIM and the case of loading the FAS inhibitor (C75). That is, AIM and C75 exhibited similar effects on both differentiation of preadipocytes and lipolysis in mature adipocytes.

It was thought that the expression of only the FAS gene was not inhibited by AIM in Example 4 above because the inhibition of the FAS function by AIM probably induced a negative feedback and the expression of the FAS gene was increased by an expression control system other than PPARγ (e.g., control by LXR-SREBP1 system).

It was also thought that when AIM was loaded to mature adipocytes to inhibit the FAS function, the amount of endogenous free fatty acids (FFAs) was decreased, and thus, lipolysis was induced as its feedback to regulate the amount of FFAs.

Example 6

Binding of AIM to FAS in Adipocytes

The FAS activity in cells is regulated not by protein modification such as phosphorylation but basically by expression control and molecular structure regulation. Even when the FAS activity is reduced by loading AIM, the expression of FAS is not decreased either in its mRNA level or in its protein amount as described above. Therefore, as one possibility, it was thought that AIM was bound to FAS to structurally inhibit its activity.

Thus, in order to confirm the fact, first, HEK293T cells which co-expressed both AIM (mouse AIM) fused with an HA-tag and FAS fused with a FLAG-tag were produced. Also, the HEK293T cells were collected after being cultured for a predetermined period of time, its cell lysate was prepared, and an immunoprecipitation was performed using an anti-FLAG antibody.

Figure 14:
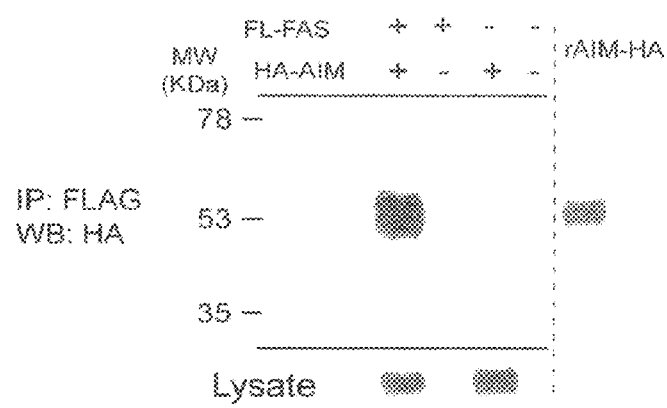
FIG. 14 is an explanatory diagram showing one example of results of immunoprecipitation which confirms a binding of AIM tagged with HA to FAS tagged with FLAG.

As a result, co-precipitation of AIM fused with the HA-tag (HA-AIM) and FAS fused with the FLAG-tag (FL-FAS) was observed as shown in FIG. 14. That is, it was confirmed that AIM had a potential to be bound to FAS. The result supported the above-mentioned hypothesis.

Example 7

Endocytosis of AIM into Adipocytes

AIM is a soluble protein secreted from macrophages. Typically, a secretory protein molecule is bound to its receptor present on the membrane surface of target cells, and elicits a signal transduction to functionally act upon the target cells. However, in order for AIM to bind to FAS to inhibit its activity as described above, AIM must be endocytosed as a molecule into the cells.

In order to prove this fact, the differentiation of 3T3-L1 cells was induced in the same manner as in the above-mentioned other examples, and the cells were loaded with AIM (mouse AIM, 5 μg/mL) for 3 hours on the 4th day (day 4) of the culture immediately after the induction of the differentiation. Subsequently, the cells were collected, and intracellularly stained using an anti-AIM antibody. Further, nuclei in the cells were stained using DAPI.

Figure 15A:
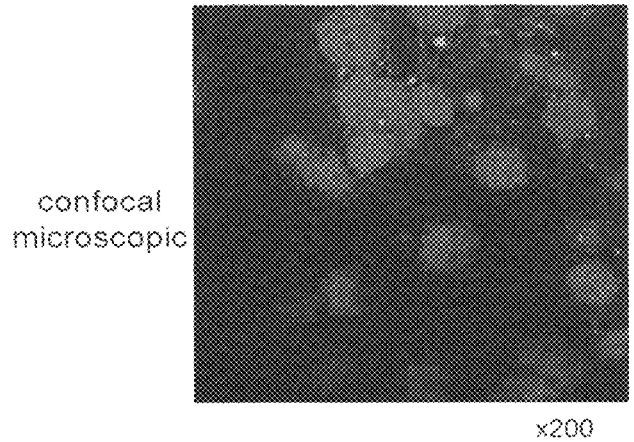
FIG. 15A is an explanatory diagram showing one example of confocal microscopic photos of cells loaded with AIM and stained with an anti-AIM antibody.
Figure 15B:
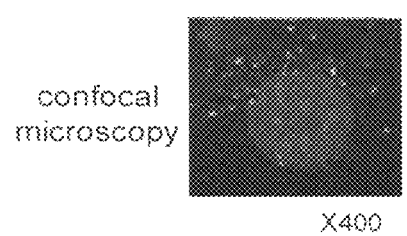
FIG. 15B is an explanatory diagram showing another example of the confocal microscopic photos of cells loaded with AIM and stained with the anti-AIM antibody.

FIG. 15A and FIG. 15B show one example of the results of observing the cells stained after being cultured for 3 hours after being loaded with AIM under a confocal microscope. FIG. 15A and FIG. 15B show the results photographed at a magnification of 200 times and 400 times, respectively. As shown in FIG. 15A and FIG. 15B, it was confirmed that AIM had been endocytosed like dots (red in an original photo) into the cytoplasm.

Figure 16B:
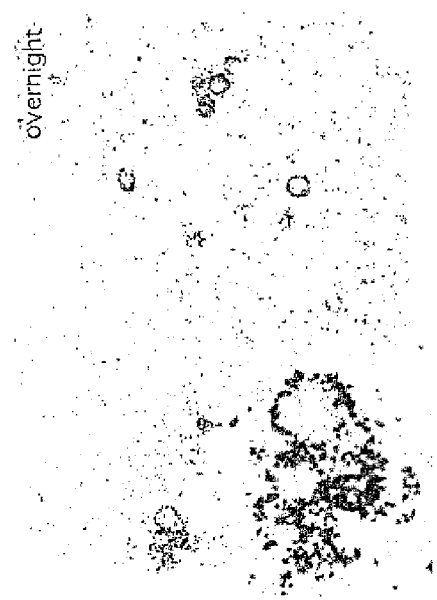
FIG. 16B is an explanatory diagram showing another example of the immunoelectron microscopic photos of cells loaded with AIM.
Figure 16A:
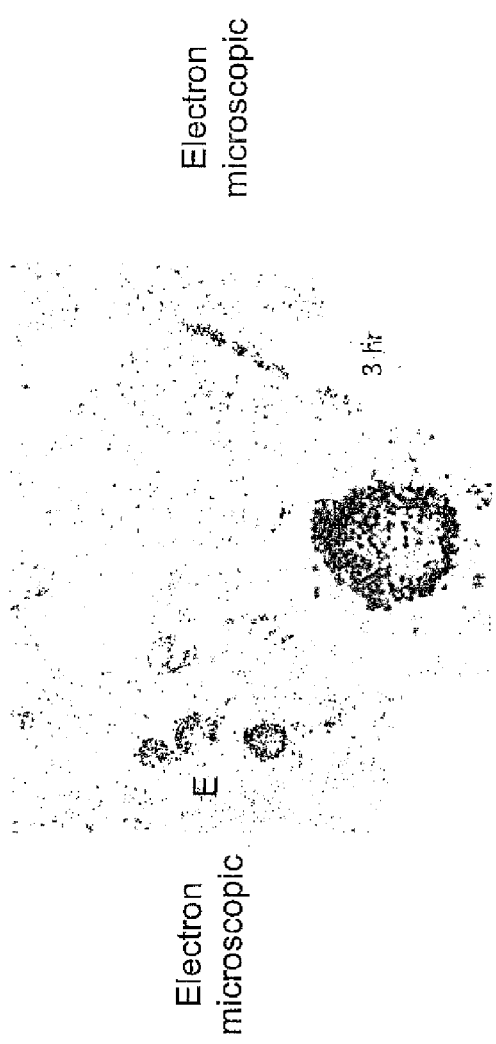
FIG. 16A is an explanatory diagram showing one example of immunoelectron microscopic photos of cells loaded with AIM.

Further, by an immunoelectron microscope using an anti-AIM antibody labeled with gold colloid, it was confirmed that AIM was endocytosed into adipocytes. FIG. 16A and FIG. 16B show immunoelectron micrographs of the cells cultured for 3 hours (3 hr) and 12 hours (overnight) after being loaded with AIM, respectively. FIG. 16A shows the results of the cells collected 3 hours after loading of AIM, and FIG. 16B shows the results of the cells collected after 12 hours passed from the loading of AIM.

As shown in FIG. 16A, AIM was accumulated like the dots on the membrane of particles thought to be endosomes in the cytoplasm of the cells cultured in the presence of AIM for 3 hours. This appeared to be AIM directly endocytosed together with a surface molecule after AIM was bound to the surface molecule on the surface of adipocytes.

Figure 17:
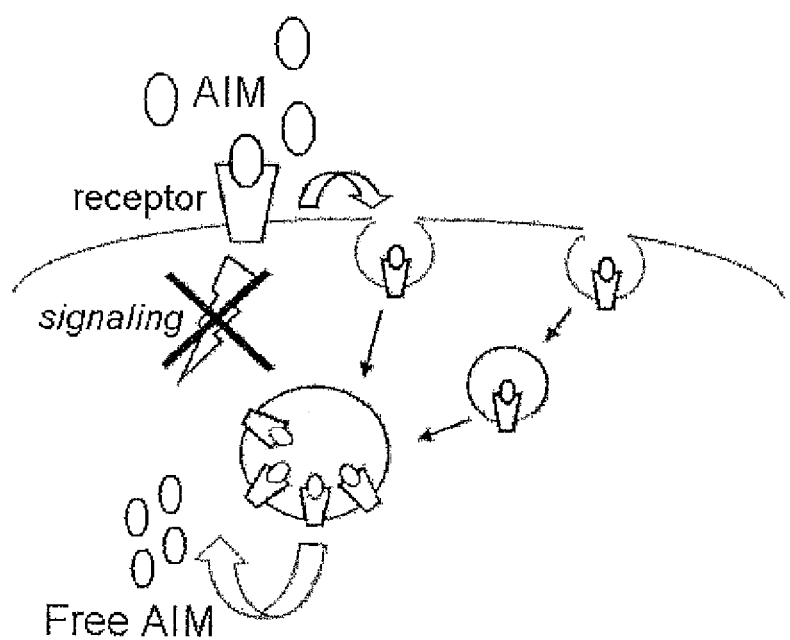
FIG. 17 is an explanatory diagram schematically illustrating a mechanism in which AIM is internalized into cells.

In addition, as shown in FIG. 16B, it was also observed that endosomes were degenerated and AIM migrated therefrom into the cytoplasm of the cell cultured in the presence of AIM for 12 hours. No AIM was accumulated on phagosomes, phagolysosomes, or mitochondria. A mechanism in which AIM is endocytosed in cells, which was speculated based on those findings, is schematically illustrated in FIG. 17.

Example 8

Internalization of AIM Via CD36 Molecule on Cell Surface

As described above, AIM was thought to be internalized into cells via cell surface molecule. Thus, the cell surface molecule was identified.

CD36 is a twice-transmembrane-type molecule, is expressed on adipocytes and macrophages, and is involved in intracellular internalization of many molecules including fatty acids, LDL, and the like. Thus, HEK293 cells in which mouse CD36 fused with a FLAG-tag at its C terminus was overexpressed were produced, and the cells were cultured with mouse AIM for 3 hours. Subsequently, the cells were collected, stained using an anti-AIM antibody and an anti-CD36 antibody, and observed under a confocal microscope.

Figure 18C:
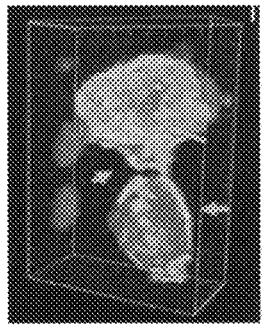
FIG. 18C is an explanatory diagram showing another example of results of the three-dimensional analysis of adipocytes co-stained for AIM and CD36 using the confocal microscope.
Figure 18D:
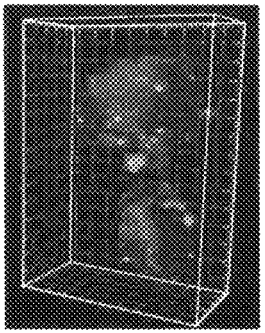
FIG. 18D is an explanatory diagram showing still another example of results of the three-dimensional analysis of adipocytes co-stained for AIM and CD36 using the confocal microscope.
Figure 18B:
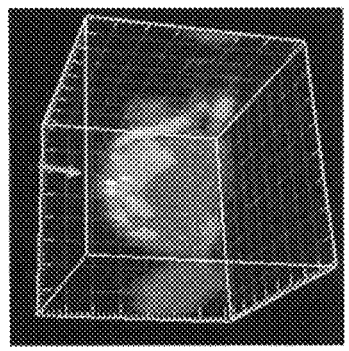
FIG. 18B is an explanatory diagram showing one example of results of three-dimensional analysis of adipocytes co-stained for AIM and CD36 using the confocal microscope.
Figure 18A:
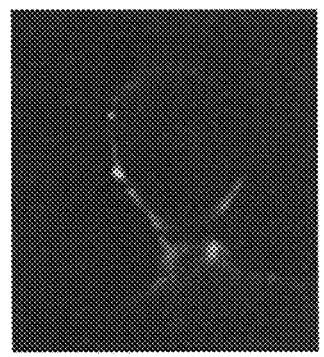
FIG. 18A is an explanatory diagram showing one example of results of two-dimensional analysis of adipocytes co-stained for AIM and CD36 using a confocal microscope.

Obtained confocal micrographs are shown in FIG. 18A to FIG. 18D. FIG. 18A shows the result of a 2-dimensional analysis and FIG. 18B to FIG. 18D show the results of 3-dimensional analyses. As shown in FIG. 18A to FIG. 18D, it was confirmed in the 2-dimensional and 3-dimensional analyses that dots of AIM (shown by green in an original photo) had been bound to sites (where FLAG is shown by red in an original photo) at which CD36 was expressed on the cells. In some cells, it was observed that AIM had been internalized into the cell. From those results, it was thought that AIM was bound to CD36 and internalized into the cells.

In this regard, however, it was mainly observed in the HEK293T cells used in this case that AIM was present on the cell surface, and it was not often observed compared with adipocytes (the differentiated 3T3-L1 cells) in Example 7 that AIM had been internalized into the cells. It was thought that this was because an ability for endocytosis in the HEK293T cells was weaker than that in adipocytes, and AIM bound to CD36 easily remained on the cell surface.

Further, in order to confirm that AIM is internalized via CD36, a neutralizing antibody which inhibited the binding of a ligand to CD36 was simultaneously loaded when the 3T3-L1 adipocyte differentiated by the above-mentioned differentiation induction was loaded with AIM. Subsequently, the cultured 3T3-L1 adipocytes were collected, and stained using an anti-AIM antibody. The 3T3-L1 adipocytes loaded with AIM alone without loading the neutralizing antibody against CD36 were cultured and stained in the same manner as described above.

Figure 19A:
FIG. 19A is an explanatory diagram showing one example of results of staining cells, which were loaded with AIM in the absence of a neutralizing antibody against CD36, with an anti-AIM antibody.
Figure 19B:
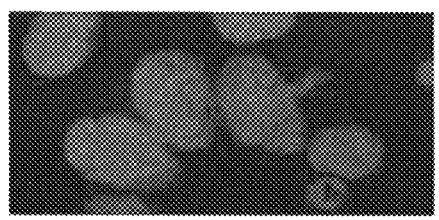
FIG. 19B is an explanatory diagram showing one example of results of staining cells, which were loaded with AIM together with the neutralizing antibody against CD36, with the anti-AIM antibody.

FIG. 19A and FIG. 19B show the results of staining when the neutralizing antibody against CD36 was not loaded (no CD36 antibody) and when the neutralizing antibody against CD36 was loaded (with CD36 neutralizing antibody), respectively. As shown in FIG. 19A, when the neutralizing antibody against CD36 was not loaded, it was observed that AIM had been internalized into the cells (AIM was detected as red dots in the cells in an original photo). Meanwhile, as shown in FIG. 19B, when the neutralizing antibody against CD36 was loaded, nothing was stained with the anti-AIM antibody in the cells, and the internalization of AIM was not observed.

That is, the internalization of AIM into the cells was remarkably inhibited by loading the neutralizing antibody against CD36. From the above-mentioned results, it was demonstrated that at least one of the molecules involved in the internalization of AIM into adipocytes was CD36.

Example 9

Increase of Body Weight and Fat Amount in AIM-Deficient Mice

From the experimental results obtained in the above-mentioned examples, it was demonstrated that AIM inhibited the maturation and the differentiation of preadipocytes and induced lipolysis in mature adipocytes. Thus, in order to examine the effect of those actions in the living body, a high fat diet (HFD) was given to AIM-deficient mice (AIM$^{-/-}$ mice) in which AIM had been knockouted and normal mice (AIM$^{+/+}$ mice) in which AIM had not been knockouted for 20 weeks or more, and the body weight and the weight of visceral white fat were measured. As a result, the increases of the body weight and the weight of visceral white fat were significantly facilitated in the AIM$^{-/-}$ AIM-deficient mice compared with the AIM$^{+/+}$ mice (data not shown).

In order to further augment the progression of obesity, an adiponectin-knockout mouse (Adipo$^{-/-}$ mouse) was crossed with each mouse to produce AIM$^{-/-}$ Adipo$^{-/-}$ mice and AIM$^{+/+}$ Adipo$^{-/-}$ mice. Then, RFD was also given to those mice for 20 weeks or more, and analyzed.

Figure 20A:
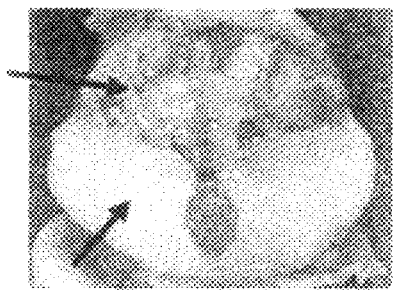
FIG. 20A is an explanatory diagram showing one example of photos obtained by photographing intraperitoneal adipose tissues in AIM$^{-/-}$ Adipo$^{-/-}$ mice.
Figure 20B:
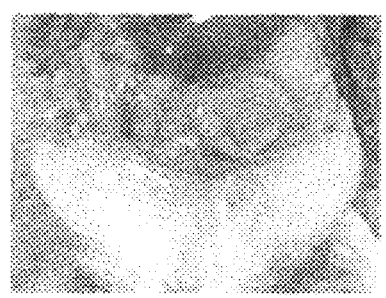
FIG. 20B is an explanatory diagram showing one example of photos obtained by photographing intraperitoneal adipose tissues in AIM$^{+/+}$ Adipo$^{-/-}$ mice.
Figure 21A:
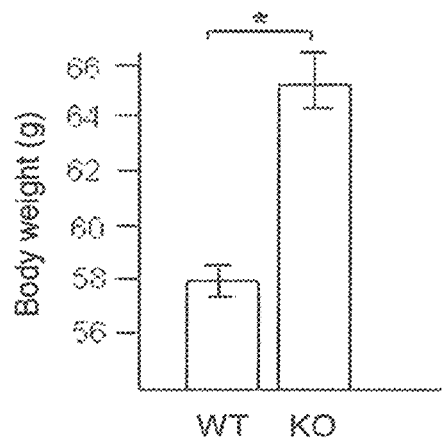
FIG. 21A is an explanatory diagram illustrating one example of results of measuring the body weight of the AIM$^{-/-}$ Adipo$^{-/-}$ mice and the AIM$^{+/+}$ Adipo$^{-/-}$ mice.
Figure 21B:
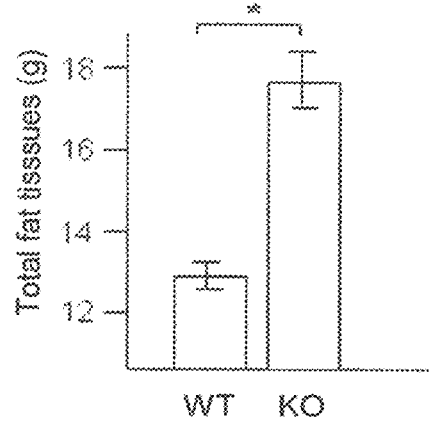
FIG. 21B is an explanatory diagram illustrating one example of results of measuring the weight of adipose tissues in the AIM$^{-/-}$ Adipo$^{-/-}$ mice and the AIM$^{+/+}$ Adipo$^{-/-}$ mice.

FIG. 20A and FIG. 20B show photos obtained by taking intraperitoneal appearances in the AIM$^{-/-}$ Adipo$^{-/-}$ mouse (AIM$^{-/-}$) and the AIM$^{+/+}$ Adipo$^{-/-}$ mouse (AIM$^{+/+}$), respectively. In FIG. 20A, an upper arrow indicates mesenteric adipose tissue and a lower arrow indicates epididymal adipose tissue. FIG. 21A and FIG. 21B illustrate the results of measuring the body weight (Body weight (g)) and the weight of visceral white fat (Total fat tissue (g)) in the AIM$^{+/+}$ Adipo$^{-/-}$ mice (WT) and the AIM$^{-/-}$ Adipo$^{-/-}$ mice (KO), respectively.

As illustrated in FIG. 21A and FIG. 21B, the increases of the body weight and the weight of visceral white fat were facilitated in the AIM$^{-/-}$ Adipo$^{-/-}$ AIM-deficient mice compared with the AIM$^{+/+}$ Adipo$^{-/-}$ mice as was the case with the above-mentioned mice in which adiponectin had not been knockouted. This facilitation of the increase of the body weight was mainly due to the facilitation of the increase of the adipose tissue weight.

Those results supported the fact that AIM secreted from macrophages infiltrating adipose tissues reduced the FAS activity in the surrounding adipose tissues to induce the lipolysis and inhibit the differentiation to new mature adipocytes, thereby regulating adipose tissue mass suppressively.

It has been reported that administration of a FAS inhibitor (C75) to mice reduces the amount of a neuropeptide Y (NPY) produced in the hypothalamus to cause remarkable appetite loss and body weight loss.

On the contrary, the amounts of food intake were not different between the AIM$^{-/-}$ mice and the AIM$^{+/+}$ mice. Therefore, in the present AIM administration experiments, it was thought that no action upon the cerebral nervous system as observed when the above-mentioned FAS inhibitor (C75) was systemically given was present, and that the increase of fat amount in the AIM$^{-/-}$ mice was attributed to the effect on adipocytes directly given by AIM deficiency.

It was thought that this was because the presence of CD36 which was a specific endocytosis mediator and was not present in hypothalamus cells, but present in adipocytes, was necessary for AIM to act.

Example 10

Induction of Lipolysis by Administration of AIM to Obese Mice

Obese AIM$^{-/-}$ mice were produced by giving HFD for 20 weeks or more. Meanwhile, a purified recombinant mouse AIM protein was prepared, and an AIM solution in which the AIM protein had been dissolved at a concentration of 0.2 mg/mL in phosphate buffered saline (PBS, pH 7.4) was prepared as an injection. Then, the AIM injection was administered to the mice from the tail vein twice a week for 4 weeks.

A dosage was 1 μg per 1 g of the body weight of the mouse. The dosage was determined based on the AIM concentration in the culture medium in the above-mentioned in vitro experiments, by considering that the AIM concentration in the blood of the mouse was a similar level to the AIM concentration in the culture medium.

In addition, as a control, the same amount of bovine serum albumin (BSA) was administered via the tail vein in the same schedule to the obese AIM$^{-/-}$ mice produced by giving HFD for 20 weeks or more. Then, the body weight of the mice after being administered was measured, and the visceral white adipose tissue was collected and its weight was measured.

As a result, although no significant difference in body weight and total weight of the adipose tissue was observed in the presence and absence of AIM administration, shrinkage and lysis of adipocytes, macrophages accumulated to process them, and preadipocytes (3T3-L1 like cells before the differentiation induction) thought to be adipocytes which had probably almost completely released (lysed) lipid droplets were observed locally (in a spotty pattern) in the adipose tissues collected from the mice to which AIM had been administered.

FIG. 22A and FIG. 22B show the results of observing adipose tissue sections stained with hematoxylin and eosin (HE) under a microscope. The result of the mouse to which albumin was administered (BSA injected (control)) is shown in FIG. 22A. The result of the mouse to which AIM was administered (rAIM injected) is shown in FIG. 22B.

As shown in FIG. 22A and FIG. 22S, the size of adipocytes in the adipose tissues were remarkably reduced, and the remarkable accumulation of macrophages was confirmed when AIM was administered compared with those when albumin was administered. That is, the systemic intravenous administration of the purified AIM protein to the obese mouse induced lipolysis in the adipose tissues of the obese mouse.

A reason why the lipolysis was locally observed in parts of the adipose tissues in this experiment has been thought to be that it is highly likely that local concentrations of AIM are not sufficiently increased in the systemic intravenous administration (the local concentration is thought to be dependent on runs of capillary blood vessels), resulting not in inducing lipolysis in the entire adipose tissues to reduce the total weight of the adipose tissues and the body weight. However, it was confirmed that AIM obviously exhibited the action of inducing lipolysis in the living body, as described above. No change in the amount of food intake due to the administration of AIM was observed.

As described above, in order to induce lipolysis by AIM, it was thought to be effective that the local concentration of AIM was increased in the living body. Therefore, it was thought that lipolysis would be reliably induced and the weight of the adipose tissues and the body weight would be effectively reduced by locally injecting AIM into the adipose tissues by local injection. It was also thought that the differentiation of preadipocytes would also be inhibited in the living body by the systemic administration and the local administration of AIM.

Here, parts of findings obtained in Examples 1 to 10 above are described. In Example 1, it was confirmed that the macrophage infiltrating the adipose tissues produced AIM in the obese mouse. It has been known that macrophages are also infiltrating to the adipose tissues in obese humans. Therefore, it was also thought that macrophages infiltrating the adipose tissues produced AIM in humans.

In Example 2, it was confirmed that AIM inhibited the maturation and the differentiation of preadipocytes. Both mouse AIM and human AIM exhibited the similar differentiation inhibitory function. It was thought that the compatibility of the differentiation inhibitory function between mouse AIM and human AIM was attributed to the high homology between the amino acid sequences of both AIM as well as the high homology of the molecules involved in the differentiation of preadipocytes and the expression of the AIM function.

In Example 3, it was confirmed that AIM acted upon mature adipocytes to induce lipolysis in the mature adipocytes. In Examples 7 and 8, it was confirmed that AIM was bound to the CD36 molecule on the cell membrane surface of adipocytes and internalized into the cytoplasm by endocytosis.

In Examples 5 and 6, it was confirmed that AIM internalized into the cells migrated to the cytoplasm and was bound to the fatty acid synthase (FAS) to inhibit its enzyme activity. Therefore, it was thought that the inhibition of the preadipocyte differentiation by AIM and the induction of lipolysis in mature adipocytes by AIM were attributed to the FAS inhibition by AIM.

In Example 9, it was confirmed that the increase of the body weight and the weight of the adipose tissues were facilitated in the AIM-deficient mice ($AIM^{-/-}$) compared with the normal ($AIM^{+/+}$) mice when a high fat diet (HFD) was loaded.

However, no difference in the amounts of food intake was observed between the AIM-deficient ($AIM^{-/-}$) mice and the normal ($AIM^{+/+}$) mice. That is, it was thought that AIM inhibited the increase of the body weight and the weight of the adipose tissues by a quite different mechanism (mechanism in which AIM specifically and directly acts upon adipocytes or adipose tissue) without inducing the loss of appetite as was observed in the conventional anti-obesity drugs.

Further, in Example 10, it was confirmed that the lipolysis locally occurred in the adipose tissues when the purified recombinant AIM protein was systemically administered (for 4 weeks) from the tail vain to the obese $AIM^{-/-}$ mice. That is, the same effect as that on the cultured cells confirmed in vitro was also actually confirmed in the living body.

As described above, human AIM and mouse AIM have the conserved characteristic three domains (SRCR1 to SRCR3) and the high homology of 68% in their amino acid sequences. In addition, CD36 involved in the internalization of AIM into adipocytes and FAS which is one of the target molecules of AIM also have the high homology between human and mouse. That is, both the molecules involved in the differentiation of preadipocytes by AIM and lipolysis by AIM in mature adipocytes have the high homology between human and mouse. Conventionally, some other pharmaceuticals sometimes exhibited no effect in humans regardless of exhibiting the effect in mice. This is primarily based on the low homology of the molecules involved in the effect between mice and humans.

Further, both human AIM and mouse AIM similarly exerted differentiation inhibitory function and lipolysis induction function in the adipocytes derived from mice in the same range of concentrations in vitro. Also, when AIM in dosages corresponding to the concentrations at which the effect had been obtained in vitro was administered to living mice, lipolysis in the adipose tissues was actually confirmed. Therefore, it was thought that it was highly likely that AIM would bring similar effects on adipocytes in the living body of humans.

The internalization of AIM into cells via CD36 must be required for AIM to exert the functions described above. According to the action mechanism, no side effect on the cerebral nervous system as observed in the conventional FAS inhibitors is conceivable when AIM is administered to the living body.

Actually, the amount of food intake in AIM-deficient mice was not different from that in normal mice. Therefore, it was thought that at least no side effect on the cerebral nervous system as observed in the conventional FAS inhibitors occurred when AIM was administered to the human living body.

Example 11

Endocytosis of AIM Administered to Obese Mice into Adipocytes and Binding of AIM to FAS Adipose tissues specimens collected from obese mice were co-stained with an anti-macrophage F4/80 antibody (red) and an anti-mouse AIM polyclonal antibody (SA-1) (green), and observed under a fluorescence microscope. As a result, some adipocytes surrounding macrophages were stained with the anti-AIM antibody. Meanwhile, the adipocytes distant from the macrophages were not stained with the anti-AIM antibody. Those results were thought to indicate that AIM derived from the macrophages was endocytosed into adipocytes in the adipose tissue.

Further, mouse rAIM was directly injected into epididymal adipose tissue in obese $AIM^{-/-}$ mice, and the adipose tissue was histologically analyzed. That is, total 100 μg of rAIM was directly injected into several sites of the epididymal adipose tissue. At 3 hours after the injection, tissue sections from the epididymal adipose tissue were made, and the tissue sections were stained with the anti-AIM antibody and the anti-macrophage antibody.

As a result, $AIM^{-/-}$ adipocytes were stained as AIM positive in the adipose tissues to which rAIM had been injected. That is, it was confirmed that exogenous rAIM was endocytosed into adipocytes in the adipose tissue. At a higher magnification, the dot-forming accumulation of endocytosed rAIM was observed in the cytoplasm of adipocytes under the fluorescence microscope.

In addition, rAIM was systemically administered by intravenous injection to $AIM^{-/-}$ mice, and subsequently adipose tissues were histologically analyzed. That is, 200 μg of rAIM was systemically administered by the intravenous injection to the $AIM^{-/-}$ mice. At 3 hours after the injection, tissue sections were made from the epididymal adipose tissue, and the tissue sections were stained with the anti-AIM antibody and the anti-macrophage antibody.

As a result, signals from the endocytosed rAIM were detected in the adipocytes in the adipose tissues, although their levels were lower than those when rAIM was directly injected into the tissue as described above. Interestingly, the macrophages in the adipose tissues were also stained with the anti-AIM antibody. The results suggested that the exogenous rAIM was also endocytosed into the macrophages.

Further, the endocytosed rAIM was precipitated using lysates derived from those adipose tissues to examine whether endogenous FAS was co-precipitated or not. That is, the presence of FAS in the precipitate was analyzed by Western blotting using HA-tagged rAIM and an anti-HA antibody.

As a result, both the rAIM protein and the FAS protein were co-precipitated. The result confirmed the association of endocytosed rAIM with cytosolic FAS.

All those results ensured that the endocytosis of AIM into adipocytes and the subsequent binding of AIM to cytosolic FAS had been physiologically accomplished in vivo.

Example 12

Promotion of Obesity Brought by AIM Deficiency

In order to test the effect of AIM on adipocytes in vivo, the state of obesity of $AIM^{-/-}$ $Adipo^{-/-}$ mice and $AIM^{+/+}$ $Adipo^{-/-}$ mice to which HFD had been given for 40 weeks or more were analyzed. Employment of the $Adipo^{-/-}$ background mice was useful for excluding the involvement of adiponectin when the effect of the AIM deficiency on the adipose tissue mass was tested.

Figure 23A:
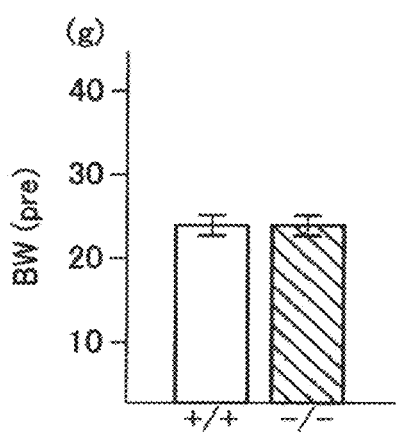
FIG. 23A is an explanatory diagram illustrating one example of results of measuring the body weight of the AIM$^{-/-}$ Adipo$^{-/-}$ mice and the AIM$^{+/+}$ Adipo$^{-/-}$ mice before the administration of HFD.
Figure 23B:
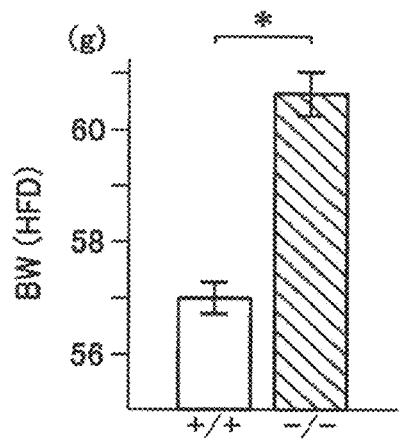
FIG. 23B is an explanatory diagram illustrating one example of results of measuring the body weight of the AIM$^{-/-}$ Adipo$^{-/-}$ mice and the AIM$^{+/+}$ Adipo$^{-/-}$ mice after the administration of HFD.
Figure 23C:
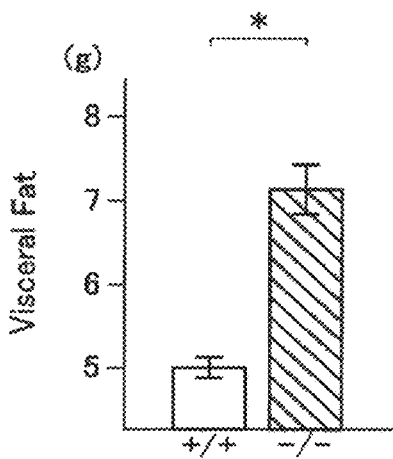
FIG. 23C is an explanatory diagram illustrating one example of results of measuring the weight of visceral fat in the AIM$^{-/-}$ Adipo$^{-/-}$ mice and the AIM$^{+/+}$ Adipo$^{-/-}$ mice.
Figure 23D:
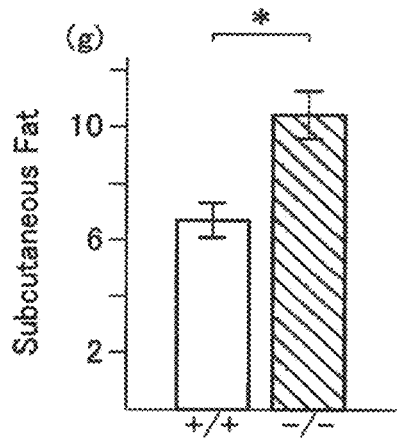
FIG. 23D is an explanatory diagram illustrating one example of results of measuring the weight of subcutaneous fat in the AIM$^{-/-}$ Adipo$^{-/-}$ mice and the AIM$^{+/+}$ Adipo$^{-/-}$ mice.
Figure 23E:
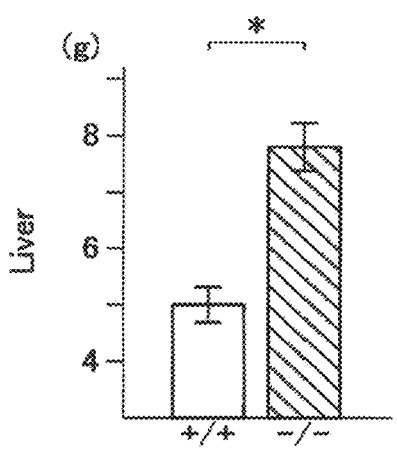
FIG. 23E is an explanatory diagram illustrating one example of results of measuring the weight of liver in the AIM$^{-/-}$ Adipo$^{-/-}$ mice and the AIM$^{+/+}$ Adipo$^{-/-}$ mice.
Figure 24A:
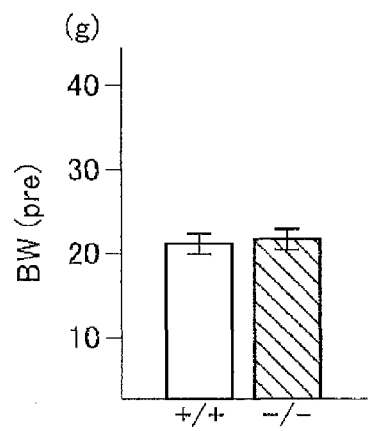
FIG. 24A is an explanatory diagram illustrating one example of results of measuring the body weight of AIM$^{-/-}$ mice and AIM$^{+/+}$ mice before the administration of HFD.
Figure 24B:
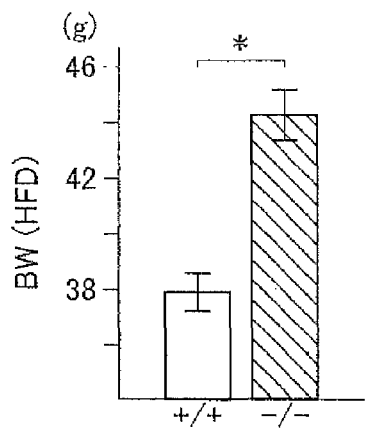
FIG. 24B is an explanatory diagram illustrating one example of results of measuring the body weights of the AIM$^{-/-}$ mice and the AIM$^{+/+}$ mice after the administration of HFD.
Figure 24C:
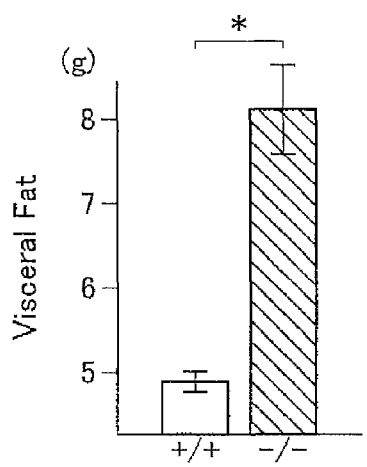
FIG. 24C is an explanatory diagram illustrating one example of results of measuring the weight of visceral adipose tissue in the AIM$^{-/-}$ mice and the AIM$^{+/+}$ mice.
Figure 24D:
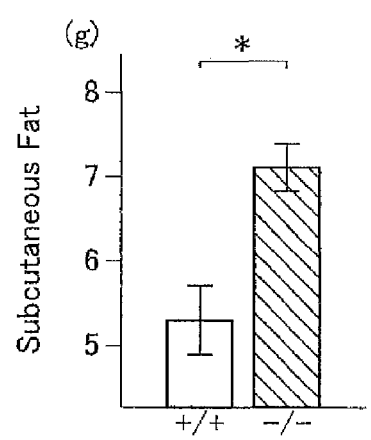
FIG. 24D is an explanatory diagram illustrating one example of results of measuring the weight of subcutaneous adipose tissue in the AIM$^{-/-}$ mice and the AIM$^{+/+}$ mice.
Figure 24E:
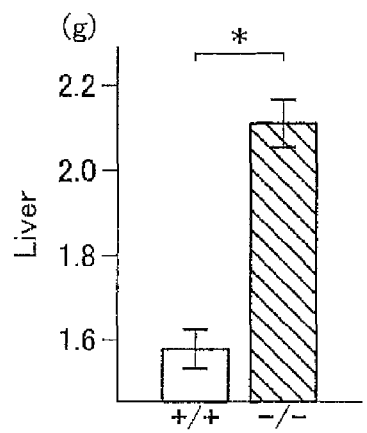
FIG. 24E is an explanatory diagram illustrating one example of results of measuring the weight of liver in the AIM$^{-/-}$ mice and the AIM$^{+/+}$ mice.

The results of the above-mentioned analysis are illustrated in FIG. 23A to FIG. 23E. The body weight before giving HFD (BW (pre), g) is shown in FIG. 23A, and the body weight after giving HFD (BW (HFD), g) is illustrated in FIG. 23B. FIG. 23C, FIG. 23D, and FIG. 23E illustrate the weight of visceral fat (g), the weight of subcutaneous fat (g), and the weight of liver (g) after giving HFD, respectively. In FIG. 23A to FIG. 23E, a symbol "+/+" denotes the results of the $AIM^{+/+}$ $Adipo^{-/-}$ mice and a symbol "−/−" denotes the results of the $AIM^{-/-}$ $Adipo^{-/-}$ mice.

As illustrated in FIG. 23A and FIG. 23B, the increase of the body weight was accelerated in the $AIM^{-/-}$ $Adipo^{-/-}$ mice compared with the $AIM^{+/+}$ $Adipo^{-/-}$ mice. The difference was mainly caused by the increase in the weight of the adipose tissues as illustrated in FIG. 23C and FIG. 23D.

As illustrated in FIG. 23E, the weight of the liver tissue was also remarkably increased in the $AIM^{-/-}$ $Adipo^{-/-}$ mice compared with the $AIM^{+/+}$ $Adipo^{-/-}$ mice. Those results indicated a possibility that AIM also acted upon hepatocytes to control glycerol storage in the hepatocytes. The weights of other organs such as heart and kidney were almost the same in both types of mice.

Similar results were also observed in the analysis of $AIM^{-/-}$ mice and $AIM^{+/+}$ mice in which adiponectin had not been knockouted and to which HFD had been given for 40 weeks or more. The results of the analysis are illustrated in FIG. 24A to FIG. 24E. As illustrated in FIG. 24A to FIG. 24E, the increase in the body weight, the adipose tissue weight, and the liver weight was more remarkable in the $AIM^{-/-}$ mice than the $AIM^{+/+}$ mice, as was the case with the $Adipo^{-/-}$ background mice.

Figure 25:
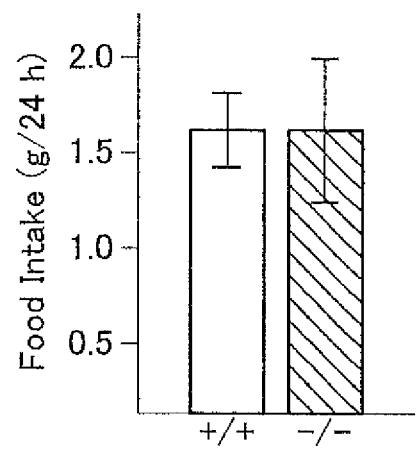
FIG. 25 is an explanatory diagram illustrating one example of results of measuring the amount of food intake in the AIM$^{-/-}$ mice and the AIM$^{+/+}$ mice.

The result of evaluating the amounts of food intake (Food intake (g/24 h)) which was an index of the appetite in the $AIM^{-/-}$ mice and the $AIM^{+/+}$ mice to which HFD had been given is illustrated in FIG. 25. The symbol "+/+" denotes the results of the $AIM^{+/+}$ mice and the symbol "−/−" denotes the results of the $AIM^{-/-}$ mice in FIG. 25.

Here, as described in above Example 9, it has been reported that the administration of a FAS inhibitor C75 reduces the production of a neuropeptide Y (NPY) in hypothalamus, resulting in remarkable loss of appetite, and thus the weight loss is totally accelerated in mice (Loftus, T. M. of al. Reduced food intake and body weight in mice treated with fatty acid synthase inhibitors. *Science* 288, 2379-2381 (2000); Kumar, M. V., Shimokawa, T., Nagy, T. R. & Lane, M. D. Differential effects of a centrally acting fatty acid synthase inhibitor in lean and obese mice. *Proc. Natl. Acad. Sci. U.S.A.* 99, 1921-1925 (2002); Shimokawa, T., Kumar, M. V. & Lane, M. D. Effect of a fatty acid synthase inhibitor on food intake and expression of hypothalamic neuropeptides. *Proc. Natl. Acad. Sci. U.S.A.* 99, 66-71 (2002); and Chakravarthy, M. V. et al. Inactivation of hypothalamic FAS protects mice from diet-induced obesity and inflammation. *J. Lipid Res.* 50, 630-640 (2009)).

On the contrary, the amounts of the food intake for 24 hours (g/24 h) were at the same level in the $AIM^{-/-}$ mice and the $AIM^{+/+}$ mice in the experiment according to the present invention, as illustrated in FIG. 25. That is, it was demonstrated that AIM had no neurological effect. It is thought that this is because the action of AIM requires the specific endocytotic process via CD36 which has not been reported to be expressed in the cells in the hypothalamus.

It should be noted that levels of TNFα and IL-6 in serum were not remarkably different and blood glucose levels were at the same level in the $AIM^{-/-}$ mice and the $AIM^{+/+}$ mice to which HFD had been given regardless of having the $Adipo^{-/-}$ background or the $Adipo^{+/+}$ background.

Example 13

Increase in Adipocyte Size, Adipose Tissue Mass, and Body Weight in AIM-Deficient Mice HFD was given to $AIM^{-/-}$ mice and $AIM^{+/+}$ mice for 20 weeks. Then, tissue sections of epididymis adipose tissues collected from each mouse were stained with HE, and observed under a microscope. The sizes of independent 50 adipocytes were evaluated in different areas within a microscopic field of each tissue section using a computer in which an image analysis software had been installed. The size of the adipocytes was expressed as mean±standard error of mean (SEM) (in pixels).

Figure 26:
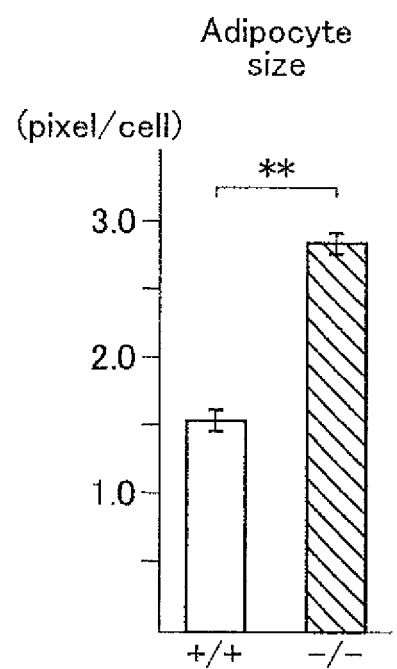
FIG. 26 is an explanatory diagram illustrating one example of results of measuring the size of adipocytes in the AIM$^{+/+}$ mice and the AIM$^{-/-}$ mice.

FIG. 26 illustrates the results of measuring adipocyte sizes (pixel/cell) in the $AIM^{+/+}$ mice ("+/+") and the $AIM^{-/-}$ mice ("−/−"). FIG. 27A and FIG. 27B show the results of observing tissue sections of visceral adipose tissue collected from the $AIM^{+/+}$ mice ("+/+") and the $AIM^{-/-}$ mice ("−/−") and stained with HE under a phase contrast microscope, respectively. A scale bar in FIG. 27A and FIG. 27B indicates a length of 100 μm.

As illustrated in FIG. 26, FIG. 27A, and FIG. 27B, the size of visceral adipocytes was larger in the obese $AIM^{-/-}$ mice than those in the obese $AIM^{+/+}$ mice, in line with the above-mentioned observation in the 3T3-L1 cells in vitro.

In addition, HFD was given to $AIM^{-/-}$ mice and $AIM^{+/+}$ mice for 12 weeks, and their body weight and weight of the adipose tissues were measured. FIG. 28A, FIG. 28B, and FIG. 28C illustrate the results of measuring the body weight (Body) (g), the weight of the visceral adipose tissue (Visceral fat) (g), and the weight of the subcutaneous adipose tissue (Subcutaneous fat) (g) in the $AIM^{+/+}$ mice ("+/+") and the $AIM^{-/-}$ mice ("−/−"), respectively.

As illustrated in FIG. 28A to FIG. 28C, the increases in the body weight, the weight of the visceral adipose tissue, and the weight of the subcutaneous adipose tissue after giving HFD for 12 weeks were further accelerated in the $AIM^{-/-}$ mice compared with the $AIM^{+/+}$ mice, in connection with the above-mentioned enlargement of the adipocytes.

Figure 29A:
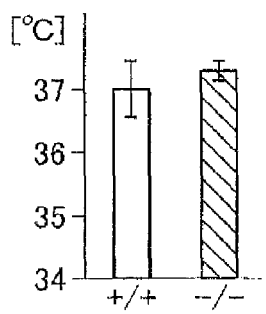
FIG. 29A is an explanatory diagram illustrating one example of results of measuring the body temperature of the AIM$^{+/+}$ mice and the AIM$^{-/-}$ mice.
Figure 29B:
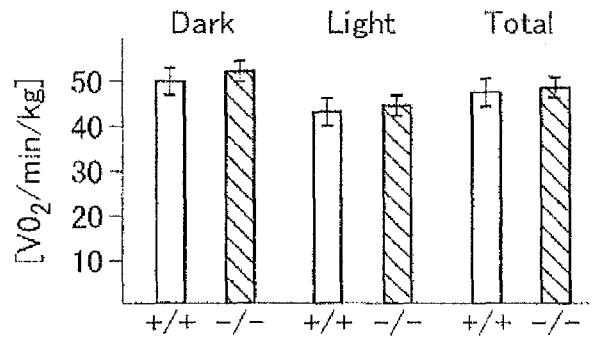
FIG. 29B is an explanatory diagram illustrating one example of results of measuring the rate of oxygen consumption in the AIM$^{+/+}$ mice and the AIM$^{-/-}$ mice.
Figure 29C:
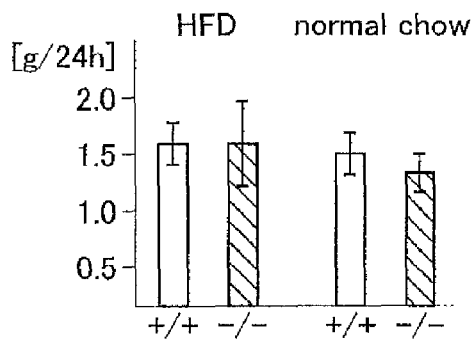
FIG. 29C is an explanatory diagram illustrating one example of results of measuring the amount of food intake in the AIM$^{+/+}$ mice and the AIM$^{-/-}$ mice.

Here, it is noteworthy that metabolic rates were at the same level in the $AIM^{+/+}$ mice and the $AIM^{-/-}$ mice to which HFD had been given. FIG. 29A, FIG. 29B, and FIG. 29C illustrate the results of evaluating body temperature (Body temperature) (° C.), oxygen consumption rates (Oxygen consumption) (VO₂/min/kg), and the amount of food intake (Food intake) (g/24 h) as the indices reflecting the metabolic rate in the AIM$^{+/+}$ mice ("+/+") and the AIM$^{-/-}$ mice ("-/-"), respectively. The amounts of food ingested per 24 hours when HFD was given (HFD) and when normal chow was given (normal chow) are illustrated in FIG. 29C. There was not much difference in body weights, oxygen consumption rates, and amounts of food intake between the AIM$^{+/+}$ mice and the AIM$^{-/-}$ mice, as illustrated in FIG. 29A to FIG. 29C.

Figure 29D:
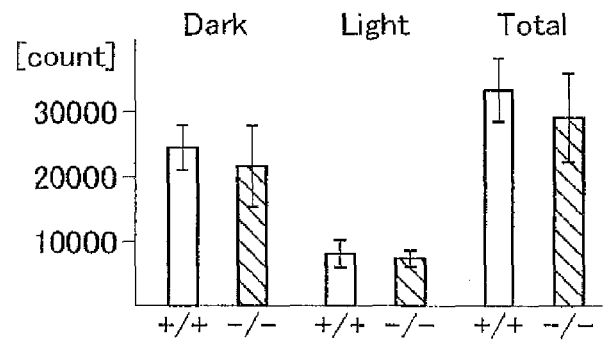
FIG. 29D is an explanatory diagram illustrating one example of results of evaluating the locomotor activity in the AIM$^{+/+}$ mice and the AIM$^{-/-}$ mice.

Further, locomotor activity was also at the same level in the AIM$^{+/+}$ mice and the AIM$^{-/-}$ mice to which HFD had been given. FIG. 29D illustrates the results of evaluating the locomotor activity (counts) in the AIM$^{+/+}$ mice ("+/+") and the AIM$^{-/-}$ mice ("-/-"). The locomotor activity under a dark environment for 12 hours (Dark), the locomotor activity under a light environment for 12 hours (Light), and the total locomotor activity for total 24 hours (Total) are illustrated in FIG. 29D.

From those results, it was thought that AIM influenced the adipose tissue mass by specifically acting upon adipocytes.

Example 14

Inhibition of Increase in Adipose Tissue Mass and Body Weight by Administration of AIM to AIM-Deficient Mice While giving HFD to AIM$^{-/-}$ mice for 15 weeks, mouse rAIM was intraperitoneally injected into the AIM$^{-/-}$ mice for the last 9 weeks to examine whether the administration of rAIM inhibits the increase of the adipose tissue mass. That is, rAIM was intraperitoneally injected three times a week into the AIM$^{-/-}$ mice ((150 μg/injection/mouse)×(three times/week)=(450 μg/mouse/week)) over the last 9 weeks, and the body weight, the weight of the visceral fat, and the weight of the subcutaneous fat were measured in the 15th week. The body weight, the weight of the visceral fat, and the weight of the subcutaneous fat were also measured in the AIM$^{-/-}$ mice as the control to which BSA (bovine serum albumin) had been intraperitoneally administered in the same administration schedule.

Figure 30A:
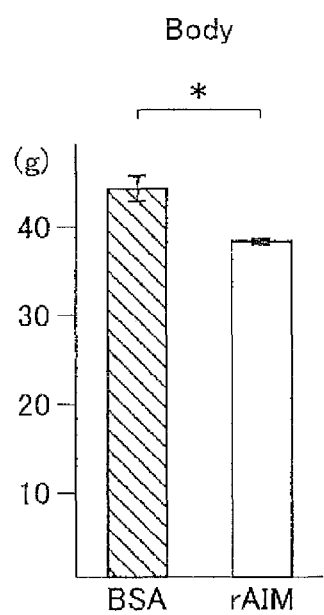
FIG. 30A is an explanatory diagram illustrating one example of results of measuring the body weight of the AIM$^{-/-}$ mice to which AIM or BSA was administered.
Figure 30B:
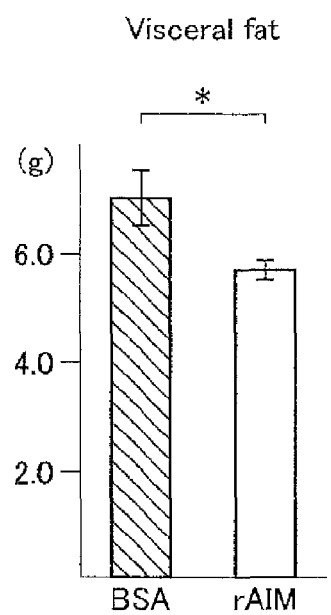
FIG. 30B is an explanatory diagram illustrating one example of results of measuring the weight of the visceral adipose tissue in the mice to which AIM or BSA was administered.
Figure 30C:
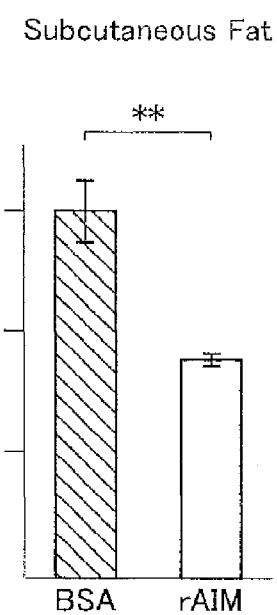
FIG. 30C is an explanatory diagram illustrating one example of results of measuring the weight of the subcutaneous adipose tissue in the AIM$^{-/-}$ mice to which AIM or BSA was administered.

FIG. 30A, FIG. 30B, and FIG. 30C show the results (n=3) of measuring the body weight (Body) (g), the weight of the visceral adipose tissue (Visceral fat) (g), and the amount of the subcutaneous adipose tissue (Subcutaneous fat) (g) in the AIM/mice to which BSA was administered (BSA) and the AIM$^{-/-}$ mice to which rAIM was administered (rAIM), respectively.

As illustrated in FIG. 30A, FIG. 30B, and FIG. 30C, the increases in both weights of the visceral fat and the subcutaneous fat as well as the body weight gain were remarkably small in the mice to which rAIM had been injected compared with the mice to which BSA had been injected as controls.

Further, mRNA levels of FSP27, perilipin, and adipophilin were evaluated in each of the AIM$^{-/-}$ mice to which BSA was administered and the AIM$^{-/-}$ mice to which rAIM was administered. The mRNA levels were measured using RNA isolated from epididymal fat and using QPCR.

Figure 31:
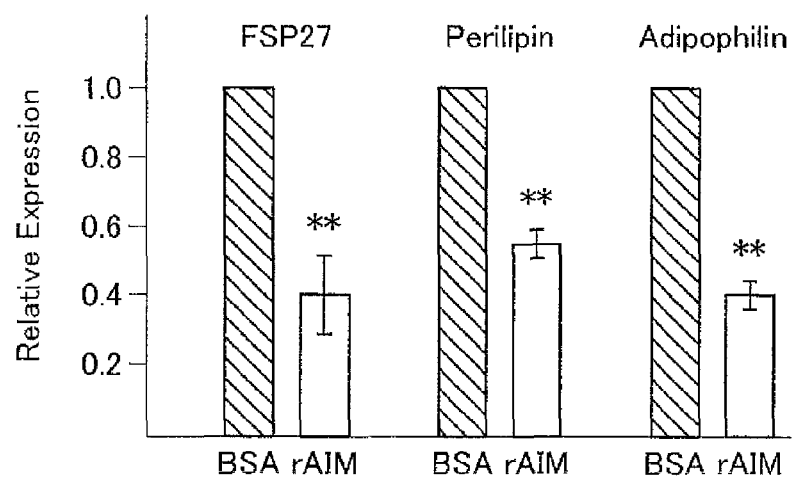
FIG. 31 is an explanatory diagram illustrating one example of results of evaluating mRNA levels in the AIM$^{-/-}$ mice to which AIM or BSA was administered.

FIG. 31 illustrates the mRNA levels (n=3) of FSP27, perilipin, and adipophilin evaluated in each of the AIM$^{-/-}$ mice to which BSA was administered (BSA) and the AIM$^{-/-}$ mice to which rAIM was administered (rAIM). It should be noted that values illustrated in FIG. 31 were normalized to GAPDH and represented as expressions relative to the results in the mice to which BSA had been injected.

As illustrated in FIG. 31, the mRNA levels of FSP27, perilipin, and adipophilin, which decreased as the lipolysis progressed, were also low in the mice to which rAIM had been injected compared with the mice to which BSA had been injected as controls, in the same way as being observed when the 3T3-L1 adipocytes were treated with rAIM as described above. Therefore, it was thought that the lipolysis had progressed in the living body by the injection of AIM.

Example 15

Binding of AIM to FAS

Figure 32:
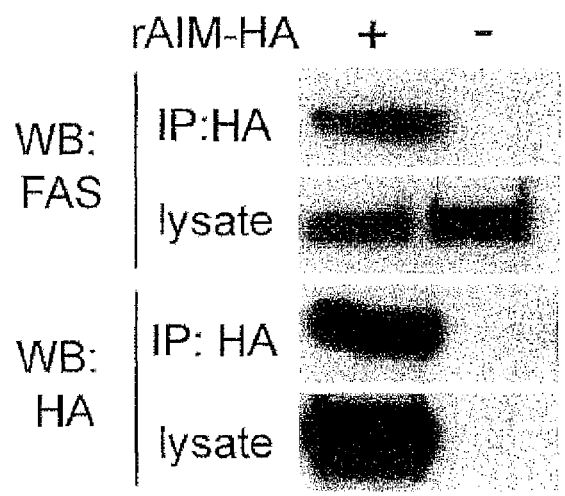
FIG. 32 is an explanatory diagram showing one example of results of confirming the binding of AIM to FAS in vivo.

It was confirmed that AIM was bound to FAS both in vivo and in vitro. That is, mouse rAIM tagged with HA in a total amount of 100 μg was directly injected in several sites in the epididymal adipose tissue in the obese AIM$^{-/-}$ mouse. At 3 hours after the injection, the epididymal adipose tissues were collected. Then, endocytosed rAIM was precipitated from a lysate of the adipose tissues using an anti-HA antibody. Then, it was analyzed by immunoblotting (WB) whether FAS was present in the resulting precipitate. As a result, both the proteins were co-precipitated as shown in FIG. 32, confirming that endocytosed rAIM was bound to endogenous FAS in the cytoplasm.

Figures 33A, 33B:
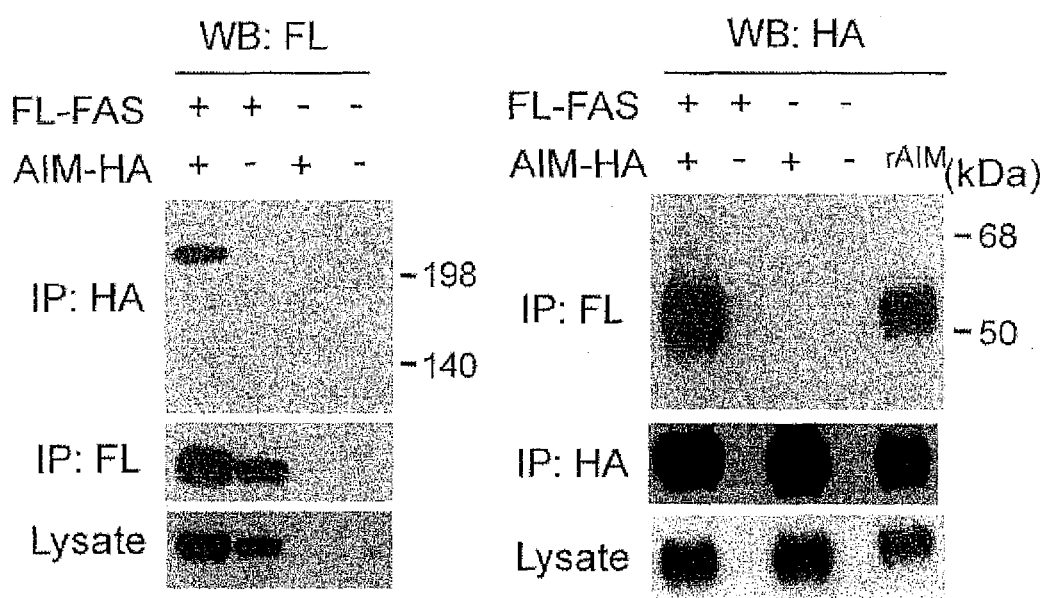
FIG. 33A is an explanatory diagram showing one example of results of confirming the binding of AIM to FAS in vitro.
FIG. 33B is an explanatory diagram showing another example of results of confirming the binding of AIM to FAS in vitro.

In addition, a co-immunoprecipitation study was performed using HEK293T cells which express both FAS tagged with FLAG and mouse AIM tagged with HA, and an anti-FLAG antibody or an anti-HA antibody. As a result, both the proteins were co-precipitated mutually as shown in FIG. 33A and FIG. 33B. Therefore, it was thought that AIM had an ability to bind to FAS.

Figure 34A:
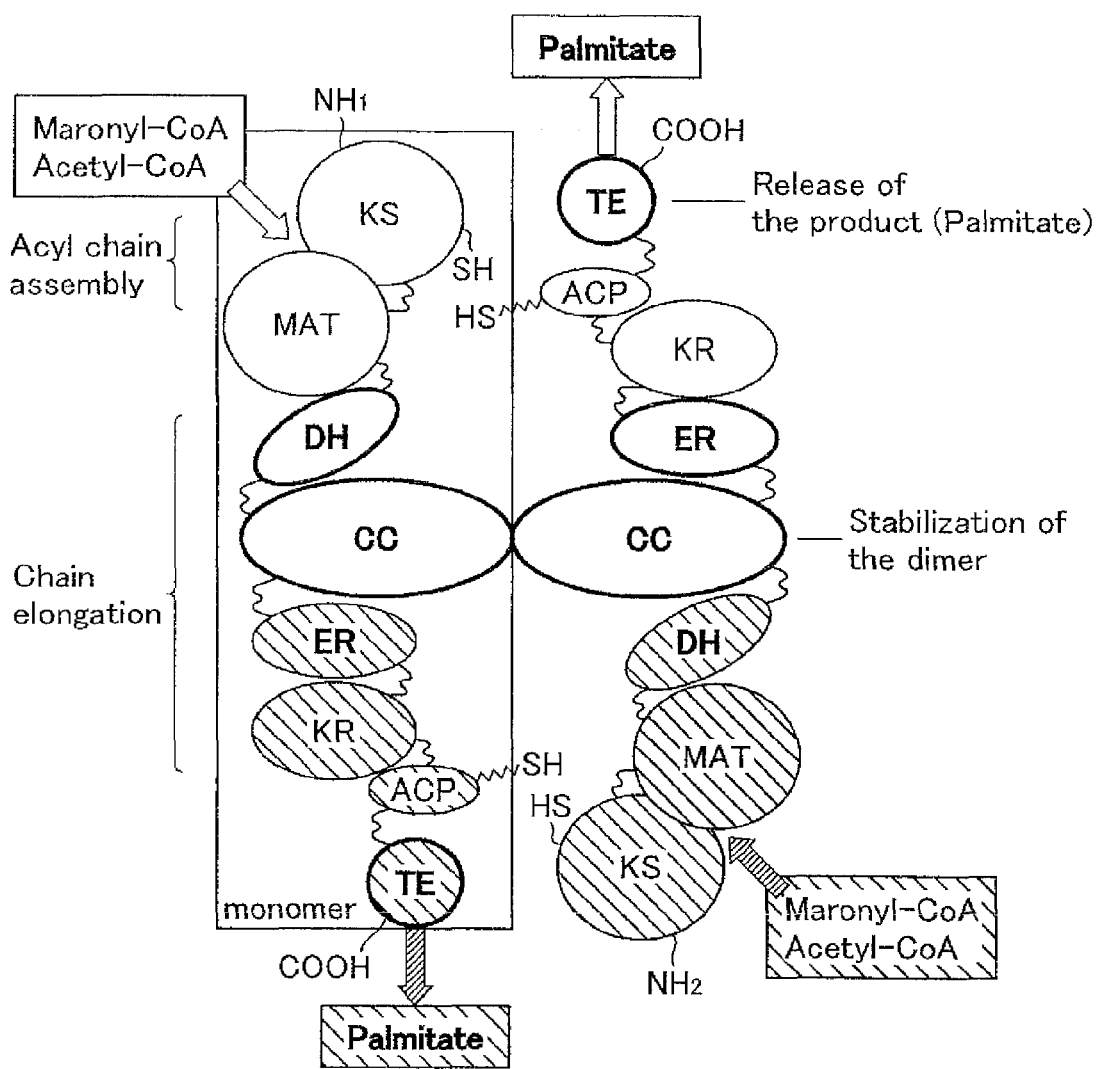
FIG. 34A is an explanatory diagram illustrating dimerized FAS and major functions of its respective regions.

Further, it was attempted to map a binding region of FAS to AIM. FAS has the following distinct seven functional domains, i.e., ketoacyl synthase (KS), malonyl/acetyl transferase (MAT), dehydrase (DH), enoylreductase (ER), ketoreductase (KR), acyl carrier protein (ACP), and thioesterase (TE), as illustrated in FIG. 34A. There is a central core (CC) between the DH domain and the ER domain. It is believed that the central core has no known catalytic function and plays a structural role in stabilization of the dimer. FIG. 34A illustrates FAS dimerized through head-to-tail interaction and major functions of its respective regions.

Figure 34B:
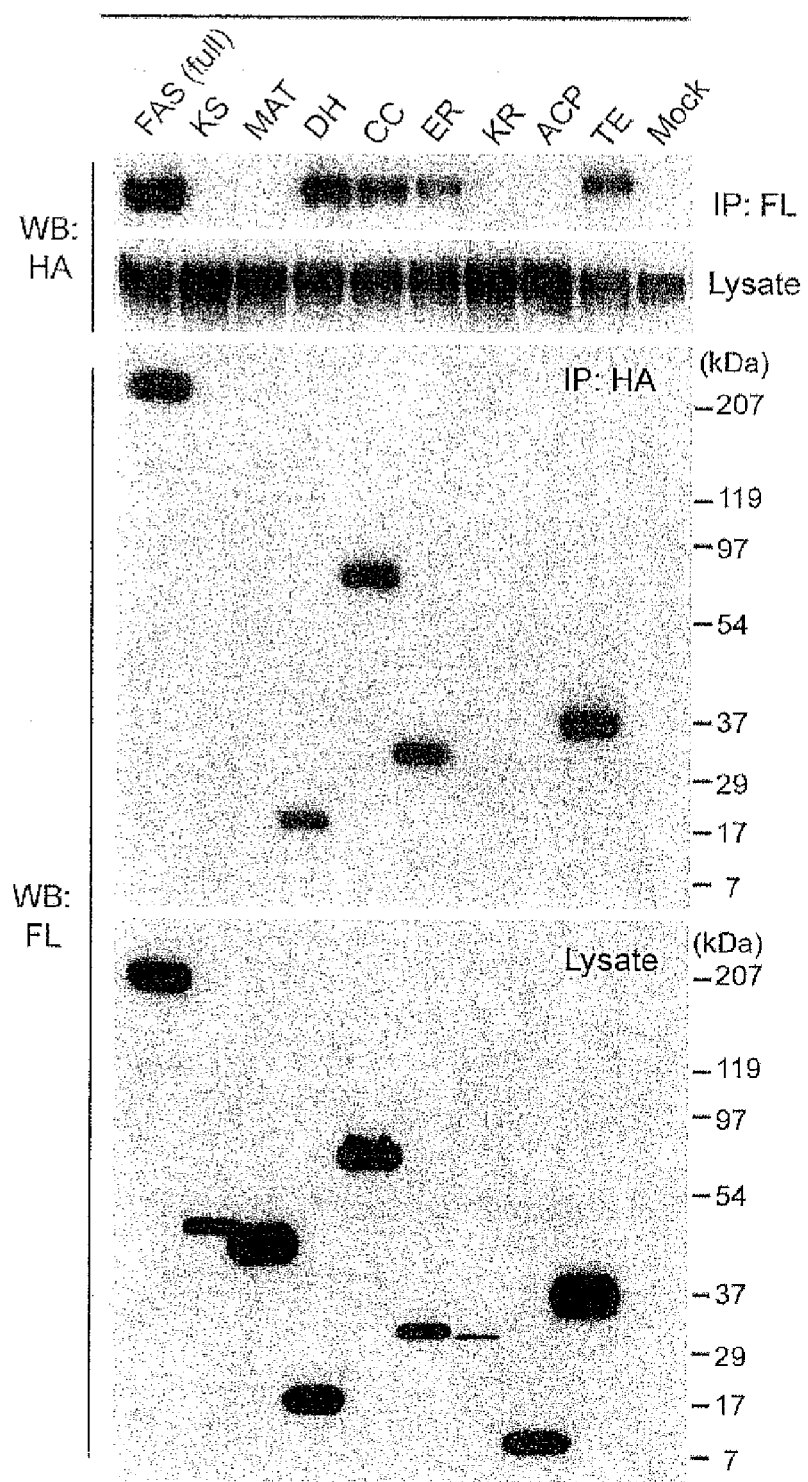
FIG. 34B is an explanatory diagram showing one example of results of tagging each region of FAS with a FLAG sequence and examining the binding of the each region to HA-tagged AIM by a co-precipitation study.

Thus, an association of each region in FAS tagged with FLAG with AIM tagged with HA was examined by a co-precipitation study. That is, each domain from FAS tagged with FLAG at the N terminus was expressed in HEK293T cells in which mouse AIM tagged with HA was stably expressed. Then, the association of each region with AIM was examined by a co-immunoprecipitation study using an anti-FLAG antibody and an anti-HA antibody. As a result, AIM was specifically bound to the ER, DH, TE, and CC domains as shown in FIG. 34B. However, AIM was not bound to an N terminal region including the KS and MAT domains (see FIG. 34A) involved in initial acyl chain assembly (i.e., condensation of acetyl group and malonyl group to 3-ketobutyryl-ACP associated with release of carbon dioxide). Therefore, it was thought that AIM affected elongation of a fatty acid chain (which involves ER and DH) and the release of synthesized palmitate (which depends on TE). Over-expression of ER or KR led to death of many cells. This caused the reduction of the signals in WB using the cell lysates of them [lower panel in FIG. 34B, lanes: ER and KR).

Example 16

Internalization of AIM Via CD36 on Cell Surface

Mouse rAIM was intravenously injected into each of a CD36$^{-/-}$ mouse which was deficient for CD36 and a wild-type CD36$^{+/+}$ mouse, and the incorporation of rAIM into the adipose tissues was analyzed. That is, an injection prepared by dissolving rAIM in PBS was intravenously injected into each of the CD36$^{-/-}$ mouse and the CD36$^{+/+}$ mouse (300 μg/mouse). At 16 hours after the injection, the mice were sacrificed, and tissue sections were made from their epididymal adipose tissue. Then, the tissue sections were stained with an anti-AIM antibody.

As a result, as shown in FIG. 35A and FIG. 35B, the levels of AIM signals detected in the adipose tissues from the CD36$^{-/-}$ mouse (CD36$^{-/-}$) were remarkably lower than those in the CD36$^{+/+}$ mouse (CD36$^{+/+}$). That is, the amount of rAIM internalized into the adipocytes was remarkably smaller in the CD36$^{-/-}$ mouse than in the CD36$^{+/+}$ mouse.

Example 17

Inhibition of Maturation of Human Preadipocytes by Human rAIM

In order to confirm that AIM also acts upon adipogenesis in human cells, the differentiation of human mesenchymal stem cells (HMSCs) (Lonza Walkersville Inc., USA) was stimulated in the presence or absence of recombinant human AIM (rhAIM).

That is, HMSCs were cultured in a mesenchymal stem cell basal medium (MSCBM) (Lonza Walkersville Inc.) for 10 days until the cells became confluent. Subsequently, the adipogenesis of the cells was stimulated by culturing the cells in the presence or absence of rhAIM (10 μg/mL) together with human insulin, MCGS, dexamethasone, indomethacin, and IBMX for 3 days (adipogenesis induction) (reference: Janderrova et al., Obes. Res., 11: 65, 2003). After the stimulation, the cells were cultured in MSCBM in which human insulin and MCGS had been added for an additional 10 days. Then, the cells were collected and stained with oil-red-o.

Figure 36A:
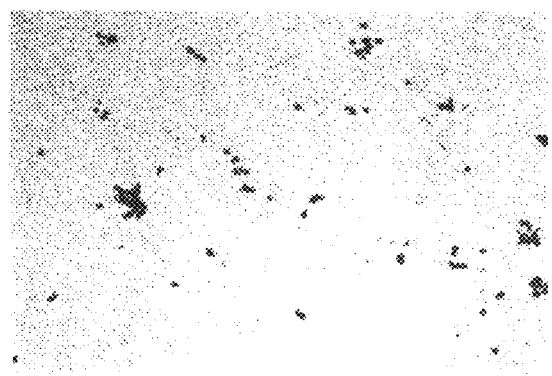
FIG. 36A is an explanatory diagram showing one example of results of observing HMSCs before stimulation under the phase contrast microscope.
Figure 36B:
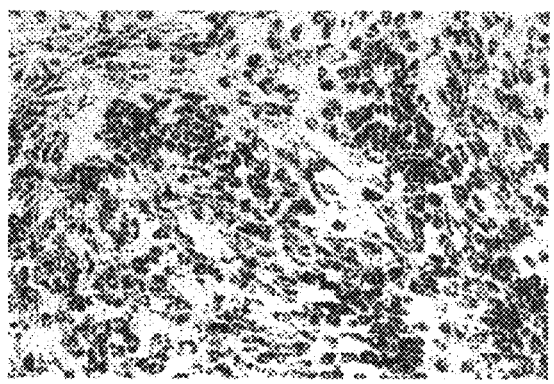
FIG. 36B is an explanatory diagram showing one example of results of observing HMSCs after stimulation in the absence of rhAIM under the phase contrast microscope.
Figure 36C:
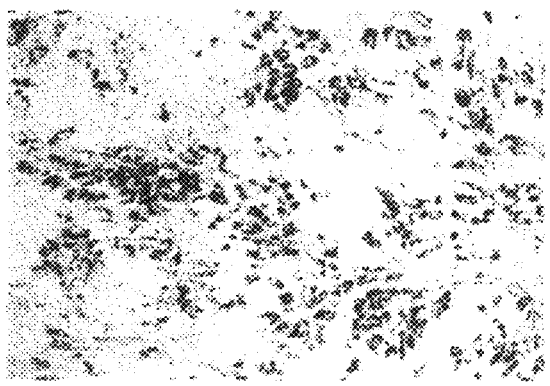
FIG. 36C is an explanatory diagram showing one example of results of observing HMSCs after differential stimulation in the presence of rhAIM under the phase contrast microscope.

FIG. 36A, FIG. 36B, and FIG. 36C show the results of observing the cells before the stimulation of adipogenesis (Pre-stimulation), after the stimulation in the absence of rhAIM (rhAIM (−)), and after the stimulation in the presence of 10 μg/mL rhAIM (rhAIM (10 μg/mL)) under the phase contrast microscope, respectively.

Figure 37:
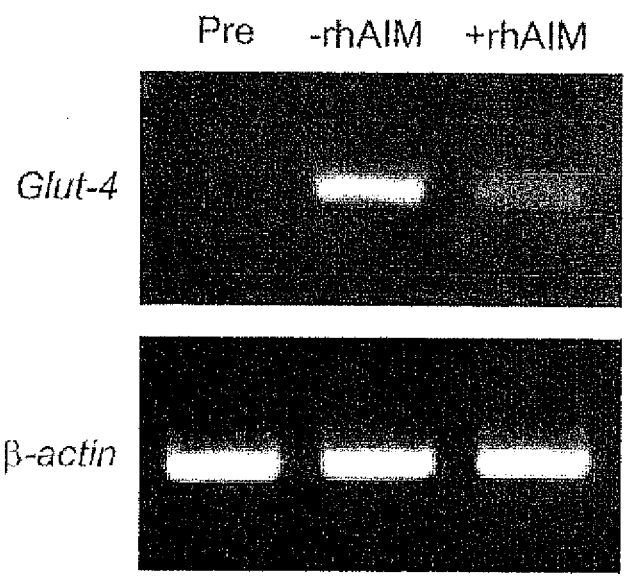
FIG. 37 is an explanatory diagram showing one example of results of evaluating the mRNA level of Glut-4 in HMSCs.

As shown in FIG. 36A, FIG. 36B, and FIG. 36C, rhAIM dramatically inhibited the differentiation of HMSCs. The mRNA level of Glut-4 which was expressed in mature adipocytes was evaluated by RT-PCR. The mRNA level of β-actin was also evaluated in the same way. The results are shown in FIG. 37. FIG. 37 shows the results of evaluating the mRNA levels of Glut-4 and β-actin before the stimulation of adipogenesis (Pre), after the stimulation in the absence of rhAIM (−rhAIM), and after the stimulation in the presence of 10 μg/mL rhAIM (+rhAIM). As shown in FIG. 37, the mRNA level of Glut-4 was remarkably decreased in the presence of rhAIM compared with that in the absence of rhAIM, in line with the results of the above-mentioned histological analysis.

Example 18

Expression of AIM in Dogs and Cats

In order to examine the expression of AIM in the dog and the cat, the Western blotting of sera collected from three dogs and three cats was performed using an anti-mouse AIM polyclonal antibody (SA-1). For comparison, the Western blotting of a serum from a mouse was also performed.

Figure 38:
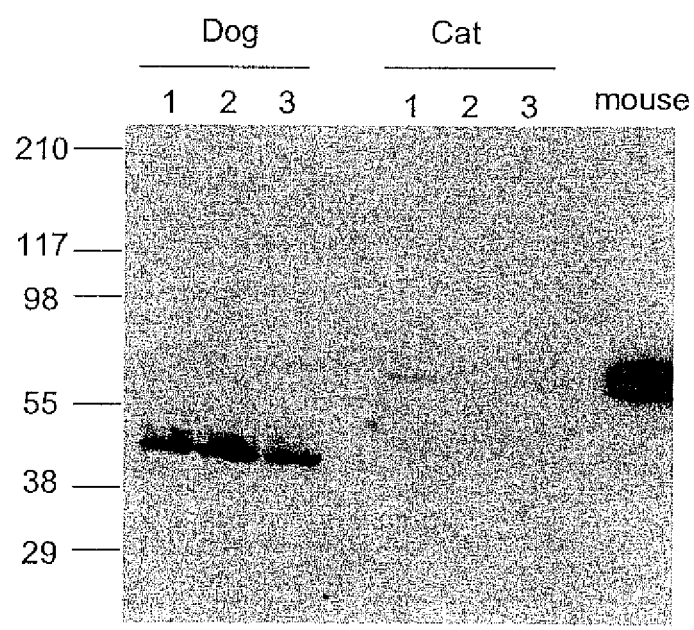
FIG. 38 is an explanatory diagram showing one example of results of performing Western blotting of dog sera and cat sera using an anti-mouse AIM antibody.

FIG. 38 shows the results of the Western blotting for the three dogs (dogs 1, 2, and 3), the three cats (cats 1, 2, and 3), and the mouse. As shown in FIG. 38, a clear band was detected for the sera from the dogs. Meanwhile, a thin band at the molecular weight, which was larger than that in the dogs and was about the same as that in the mouse, was detected for the sera from the cats. That is, it was confirmed that AIM was expressed, which had a homology to an extent that the AIM was detected by the anti-mouse AIM polyclonal antibody, in the dogs and the cats.

Here, parts of the findings obtained in Examples 11 to 18 above are described. In Example 11, it was shown that the administered exogenous rAIM was endocytosed into adipocytes and the endocytosed rAIM was bound to endogenous FAS in the cytoplasm both when rAIM was directly injected into the epididymal adipose tissue in the AIM$^{-/-}$ mouse and when rAIM was intravenously injected into the AIM$^{-/-}$ mouse. In Example 16, it was confirmed that when rAIM was intravenously injected into each of the CD36$^{-/-}$ mouse and the wild-type CD36$^{+/+}$ mouse, the amount of rAIM endocytosed into the adipocyte was remarkably small in the CD36$^{-/-}$ mouse compared with that in the CD36$^{+/+}$ mouse. That is, phenomena confirmed in vitro using the cultured cells in above-mentioned Examples 5 to 8 were also confirmed in vivo using the mice. In Example 15, it was reconfirmed that AIM was bound to FAS in the cell, and the finding for the binding region of FAS to AIM was also obtained.

In Example 12 and Example 13, it was shown that the increases in the body weight, the weight of the adipose tissues, the weight of the liver, and the sizes of the adipocytes included in the adipose tissues were remarkably promoted in the AIM$^{-/-}$ mice to which HFD had been given compared with those in the AIM$^{+/+}$ mice to which HFD had been also given, but none the less, the amount of the food intake, the metabolic rate, and the locomotor activity were at about the same levels in the AIM$^{-/-}$ mice and the AIM$^{+/+}$ mice. That is, the phenomena confirmed in above-mentioned Example 9 were also confirmed in more detail.

In Example 14, it was shown that the increases in the body weight, the weight of the visceral fat, and the weight of the subcutaneous fat were remarkably inhibited in the AIM$^{-/-}$ mice to which HFD and the intraperitoneal injection of rAIM were given simultaneously compared with those in the AIM$^{-/-}$ mice to which HFD and the intraperitoneal injection of BSA were given simultaneously. Such effects by AIM were also confirmed by the analysis results showing that the mRNA levels of FSP27, perilipin, and adipophilin, which decreased as the lipolysis progressed, were lower in the AIM$^{-/-}$ mice to which rAIM was intraperitoneally injected than in the AIM$^{-/-}$ mice to which BSA was intraperitoneally injected. That is, as already understood in above-mentioned Example 10, it was clearly confirmed that the administration of AIM inhibited the increases in the body weight and the weight of the adipose tissues, by the intraperitoneal injection which increases the local concentration in the adipose tissues compared with the intravenous injection.

In Example 17, it was confirmed that the differentiation of human preadipocytes to human adipocytes was inhibited by allowing human AIM to act upon the preadipocytes. That is, as already understood based on the findings obtained in above-mentioned Examples 1 to 10 and the homology for the structures of the AIM molecules and their action mechanisms between the mouse and the human, it was confirmed that human AIM acted upon the human cells in the same way that mouse AIM acted upon the mouse cells. The result reinforced the bases which supported the understanding that AIM also inhibited the differentiation of preadipocytes, induced lipolysis in the adipocyte, inhibited the increase in the weight of the adipose tissues and inhibited the body weight gain in the human living body as in the mouse living body.

In Example 18, it was confirmed that AIM having the homology to mouse AIM to an extent that AIM was detected using the anti-mouse AIM polyclonal antibody was also expressed in the dog and the cat. In fact, dog AIM including the amino acid sequence shown in SEQ ID NO: 11 has 66% homology to human AIM shown in SEQ ID NO: 1, and 60% homology to mouse AIM shown in SEQ ID NO: 5.

As described above, the findings have been obtained that AIM brings about the effects, based on the homology of the amino acid sequences of AIM and the similarity of the action mechanisms of AIM among various mammalian species, such as decrease of the adipose tissue mass and the body weight, inhibition of increases of the adipose tissue mass and the body weight, and reduction of increasing levels of the adipose tissue mass and the body weight, in a living body, by being administered to the living body. Further, the findings have been also obtained that AIM specifically acts upon adipocytes in the living body, based on the mechanism that AIM acts upon the cell by being internalized into the cell via CD36, without changing the metabolic state in the living body, and the findings are extremely interesting in terms of usefulness and safety as a pharmaceutical.

What is claimed is:

1. A method of decreasing adipose tissues or inhibiting growth of adipose tissues, comprising:
   administering an effective amount of a composition to a human or nonhuman animal in need of decreasing adipose tissues or inhibiting growth of adipose tissues, the composition comprising:
   an apoptosis inhibitor of macrophage (AIM) consisting of the amino acid sequence set forth in SEQ ID NO: 1, and
   a pharmaceutically acceptable carrier.

2. The method according to claim 1, wherein the composition is administered to a human.

3. The method according to claim 1, wherein the method inhibits differentiation of preadipocytes to mature adipocytes and/or induces lipolysis in mature adipocytes.

4. A method of decreasing adipose tissues or inhibiting growth of adipose tissues, comprising:
   administering an effective amount of a composition to a human or nonhuman animal in need of decreasing adipose tissues or inhibiting growth of adipose tissues, the composition comprising a protein selected from the group consisting of:
   (a) a first domain protein consisting of the amino acid sequence set forth in SEQ ID NO: 2,
   (b) a second domain protein consisting of the amino acid sequence set forth in SEQ ID NO: 3, and
   (c) a third domain protein consisting of the amino acid sequence set forth in SEQ ID NO: 4; and
   a pharmaceutically acceptable carrier.

5. A method of decreasing adipose tissues or inhibiting growth of adipose tissues, comprising:
   administering an effective amount of a composition to a human or nonhuman animal in need of decreasing adipose tissues or inhibiting growth of adipose tissues, the composition comprising:
   an apoptosis inhibitor of macrophage (AIM) consisting of the amino acid sequence set forth in SEQ ID NO: 5, and
   a pharmaceutically acceptable carrier.

6. The method according to claim 5, wherein the composition is administered to a nonhuman animal.

7. The method according to claim 5, wherein the method inhibits differentiation of preadipocytes to mature adipocytes and/or induces lipolysis in mature adipocytes.

8. A method of decreasing adipose tissues or inhibiting growth of adipose tissues, comprising:
   administering an effective amount of a composition to a human or nonhuman animal in need of decreasing adipose tissues or inhibiting growth of adipose tissues, the composition comprising a protein selected from the group consisting of:
   (a) a first domain protein consisting of the amino acid sequence set forth in SEQ ID NO: 6,
   (b) a second domain protein consisting of the amino acid sequence set forth in SEQ ID NO: 7, and
   (c) a third domain protein consisting of the amino acid sequence set forth in SEQ ID NO: 8; and
   a pharmaceutically acceptable carrier.

* * * * *

```
                         SEQUENCE LISTING

<160> NUMBER OF SEQ ID NOS: 13

<210> SEQ ID NO 1
<211> LENGTH: 347
<212> TYPE: PRT
<213> ORGANISM: human

<400> SEQUENCE: 1

Met Ala Leu Leu Phe Ser Leu Ile Leu Ala Ile Cys Thr Arg Pro Gly
1               5                   10                  15

Phe Leu Ala Ser Pro Ser Gly Val Arg Leu Val Gly Gly Leu His Arg
                20                  25                  30

Cys Glu Gly Arg Val Glu Val Glu Gln Lys Gly Gln Trp Gly Thr Val
            35                  40                  45

Cys Asp Asp Gly Trp Asp Ile Lys Asp Val Ala Val Leu Cys Arg Glu
        50                  55                  60

Leu Gly Cys Gly Ala Ala Ser Gly Thr Pro Ser Gly Ile Leu Tyr Glu
65                  70                  75                  80

Pro Pro Ala Glu Lys Glu Gln Lys Val Leu Ile Gln Ser Val Ser Cys
                85                  90                  95

Thr Gly Thr Glu Asp Thr Leu Ala Gln Cys Glu Gln Glu Glu Val Tyr
            100                 105                 110

Asp Cys Ser His Asp Glu Asp Ala Gly Ala Ser Cys Glu Asn Pro Glu
        115                 120                 125

Ser Ser Phe Ser Pro Val Pro Glu Gly Val Arg Leu Ala Asp Gly Pro
    130                 135                 140

Gly His Cys Lys Gly Arg Val Glu Val Lys His Gln Asn Gln Trp Tyr
145                 150                 155                 160

Thr Val Cys Gln Thr Gly Trp Ser Leu Arg Ala Ala Lys Val Val Cys
                165                 170                 175

Arg Gln Leu Gly Cys Gly Arg Ala Val Leu Thr Gln Lys Arg Cys Asn
            180                 185                 190

Lys His Ala Tyr Gly Arg Lys Pro Ile Trp Leu Ser Gln Met Ser Cys
        195                 200                 205

Ser Gly Arg Glu Ala Thr Leu Gln Asp Cys Pro Ser Gly Pro Trp Gly
    210                 215                 220

Lys Asn Thr Cys Asn His Asp Glu Asp Thr Trp Val Glu Cys Glu Asp
225                 230                 235                 240

Pro Phe Asp Leu Arg Leu Val Gly Gly Asp Asn Leu Cys Ser Gly Arg
                245                 250                 255

Leu Glu Val Leu His Lys Gly Val Trp Gly Ser Val Cys Asp Asp Asn
            260                 265                 270

Trp Gly Glu Lys Glu Asp Gln Val Val Cys Lys Gln Leu Gly Cys Gly
```

```
                275                 280                 285
Lys Ser Leu Ser Pro Ser Phe Arg Asp Arg Lys Cys Tyr Gly Pro Gly
        290                 295                 300

Val Gly Arg Ile Trp Leu Asp Asn Val Arg Cys Ser Gly Glu Glu Gln
305                 310                 315                 320

Ser Leu Glu Gln Cys Gln His Arg Phe Trp Gly Phe His Asp Cys Thr
                325                 330                 335

His Gln Glu Asp Val Ala Val Ile Cys Ser Gly
        340                 345

<210> SEQ ID NO 2
<211> LENGTH: 102
<212> TYPE: PRT
<213> ORGANISM: Artificial
<220> FEATURE:
<223> OTHER INFORMATION: SRCR1 domain of human AIM

<400> SEQUENCE: 2

Val Arg Leu Val Gly Gly Leu His Arg Cys Glu Gly Arg Val Glu Val
1               5                   10                  15

Glu Gln Lys Gly Gln Trp Gly Thr Val Cys Asp Asp Gly Trp Asp Ile
            20                  25                  30

Lys Asp Val Ala Val Leu Cys Arg Glu Leu Gly Cys Gly Ala Ala Ser
        35                  40                  45

Gly Thr Pro Ser Gly Ile Leu Tyr Glu Pro Pro Ala Glu Lys Glu Gln
    50                  55                  60

Lys Val Leu Ile Gln Ser Val Ser Cys Thr Gly Thr Glu Asp Thr Leu
65                  70                  75                  80

Ala Gln Cys Glu Gln Glu Glu Val Tyr Asp Cys Ser His Asp Glu Asp
                85                  90                  95

Ala Gly Ala Ser Cys Glu
            100

<210> SEQ ID NO 3
<211> LENGTH: 102
<212> TYPE: PRT
<213> ORGANISM: Artificial
<220> FEATURE:
<223> OTHER INFORMATION: SRCR2 domain of human AIM

<400> SEQUENCE: 3

Val Arg Leu Ala Asp Gly Pro Gly His Cys Lys Gly Arg Val Glu Val
1               5                   10                  15

Lys His Gln Asn Gln Trp Tyr Thr Val Cys Gln Thr Gly Trp Ser Leu
            20                  25                  30

Arg Ala Ala Lys Val Val Cys Arg Gln Leu Gly Cys Gly Arg Ala Val
        35                  40                  45

Leu Thr Gln Lys Arg Cys Asn Lys His Ala Tyr Gly Arg Lys Pro Ile
    50                  55                  60

Trp Leu Ser Gln Met Ser Cys Ser Gly Arg Glu Ala Thr Leu Gln Asp
65                  70                  75                  80

Cys Pro Ser Gly Pro Trp Gly Lys Asn Thr Cys Asn His Asp Glu Asp
                85                  90                  95

Thr Trp Val Glu Cys Glu
            100

<210> SEQ ID NO 4
<211> LENGTH: 103
<212> TYPE: PRT
```

<213> ORGANISM: Artificial
<220> FEATURE:
<223> OTHER INFORMATION: SRCR3 domain of human AIM

<400> SEQUENCE: 4

```
Leu Arg Leu Val Gly Gly Asp Asn Leu Cys Ser Gly Arg Leu Glu Val
1               5                   10                  15

Leu His Lys Gly Val Trp Gly Ser Val Cys Asp Asp Asn Trp Gly Glu
            20                  25                  30

Lys Glu Asp Gln Val Val Cys Lys Gln Leu Gly Cys Gly Lys Ser Leu
        35                  40                  45

Ser Pro Ser Phe Arg Asp Arg Lys Cys Tyr Gly Pro Gly Val Gly Arg
    50                  55                  60

Ile Trp Leu Asp Asn Val Arg Cys Ser Gly Glu Glu Gln Ser Leu Glu
65                  70                  75                  80

Gln Cys Gln His Arg Phe Trp Gly Phe His Asp Cys Thr His Gln Glu
                85                  90                  95

Asp Val Ala Val Ile Cys Ser
            100
```

<210> SEQ ID NO 5
<211> LENGTH: 352
<212> TYPE: PRT
<213> ORGANISM: mouse

<400> SEQUENCE: 5

```
Met Ala Pro Leu Phe Asn Leu Met Leu Ala Ile Leu Ser Ile Phe Val
1               5                   10                  15

Gly Ser Cys Phe Ser Glu Ser Pro Thr Lys Val Gln Leu Val Gly Gly
            20                  25                  30

Ala His Arg Cys Glu Gly Arg Val Glu Val Glu His Asn Gly Gln Trp
        35                  40                  45

Gly Thr Val Cys Asp Asp Gly Trp Asp Arg Arg Asp Val Ala Val Val
    50                  55                  60

Cys Arg Glu Leu Asn Cys Gly Ala Val Ile Gln Thr Pro Arg Gly Ala
65                  70                  75                  80

Ser Tyr Gln Pro Pro Ala Ser Glu Gln Arg Val Leu Ile Gln Gly Val
                85                  90                  95

Asp Cys Asn Gly Thr Glu Asp Thr Leu Ala Gln Cys Glu Leu Asn Tyr
            100                 105                 110

Tyr Val Phe Asp Cys Ser His Glu Glu Asp Ala Gly Ala Gln Cys Glu
        115                 120                 125

Asn Pro Asp Ser Asp Leu Leu Phe Ile Pro Glu Asp Val Arg Leu Val
    130                 135                 140

Asp Gly Pro Gly His Cys Gln Gly Arg Val Glu Val Leu His Gln Ser
145                 150                 155                 160

Gln Trp Ser Thr Val Cys Lys Ala Gly Trp Asn Leu Gln Val Ser Lys
                165                 170                 175

Val Val Cys Arg Gln Leu Gly Cys Gly Arg Ala Leu Leu Thr Tyr Gly
            180                 185                 190

Ser Cys Asn Lys Asn Thr Gln Gly Lys Gly Pro Ile Trp Met Gly Lys
        195                 200                 205

Met Ser Cys Ser Gly Gln Glu Ala Asn Leu Arg Ser Cys Leu Leu Ser
    210                 215                 220

Arg Leu Glu Asn Asn Cys Thr His Gly Glu Asp Thr Trp Met Glu Cys
225                 230                 235                 240
```

```
Glu Asp Pro Phe Glu Leu Lys Leu Val Gly Asp Thr Pro Cys Ser
                245                 250                 255

Gly Arg Leu Glu Val Leu His Lys Gly Ser Trp Gly Ser Val Cys Asp
                260                 265                 270

Asp Asn Trp Gly Glu Lys Glu Asp Gln Val Val Cys Lys Gln Leu Gly
            275                 280                 285

Cys Gly Lys Ser Leu His Pro Ser Pro Lys Thr Arg Lys Ile Tyr Gly
            290                 295                 300

Pro Gly Ala Gly Arg Ile Trp Leu Asp Asp Val Asn Cys Ser Gly Lys
305                 310                 315                 320

Glu Gln Ser Leu Glu Phe Cys Arg His Arg Leu Trp Gly Tyr His Asp
                325                 330                 335

Cys Thr His Lys Glu Asp Val Glu Val Ile Cys Thr Asp Phe Asp Val
                340                 345                 350

<210> SEQ ID NO 6
<211> LENGTH: 102
<212> TYPE: PRT
<213> ORGANISM: Artificial
<220> FEATURE:
<223> OTHER INFORMATION: SRCR1 domain of mouse AIM

<400> SEQUENCE: 6

Val Gln Leu Val Gly Gly Ala His Arg Cys Glu Gly Arg Val Glu Val
1               5                   10                  15

Glu His Asn Gly Gln Trp Gly Thr Val Cys Asp Asp Gly Trp Asp Arg
            20                  25                  30

Arg Asp Val Ala Val Val Cys Arg Glu Leu Asn Cys Gly Ala Val Ile
        35                  40                  45

Gln Thr Pro Arg Gly Ala Ser Tyr Gln Pro Pro Ala Ser Glu Gln Arg
    50                  55                  60

Val Leu Ile Gln Gly Val Asp Cys Asn Gly Thr Glu Asp Thr Leu Ala
65                  70                  75                  80

Gln Cys Glu Leu Asn Tyr Tyr Val Phe Asp Cys Ser His Glu Glu Asp
                85                  90                  95

Ala Gly Ala Gln Cys Glu
            100

<210> SEQ ID NO 7
<211> LENGTH: 101
<212> TYPE: PRT
<213> ORGANISM: Artificial
<220> FEATURE:
<223> OTHER INFORMATION: SRCR2 domain of mouse AIM

<400> SEQUENCE: 7

Val Arg Leu Val Asp Gly Pro Gly His Cys Gln Gly Arg Val Glu Val
1               5                   10                  15

Leu His Gln Ser Gln Trp Ser Thr Val Cys Lys Ala Gly Trp Asn Leu
            20                  25                  30

Gln Val Ser Lys Val Val Cys Arg Gln Leu Gly Cys Gly Arg Ala Leu
        35                  40                  45

Leu Thr Tyr Gly Ser Cys Asn Lys Asn Thr Gln Gly Lys Gly Pro Ile
    50                  55                  60

Trp Met Gly Lys Met Ser Cys Ser Gly Gln Glu Ala Asn Leu Arg Ser
65                  70                  75                  80

Cys Leu Leu Ser Arg Leu Glu Asn Asn Cys Thr His Gly Glu Asp Thr
                85                  90                  95
```

Trp Met Glu Cys Glu
        100

<210> SEQ ID NO 8
<211> LENGTH: 103
<212> TYPE: PRT
<213> ORGANISM: Artificial
<220> FEATURE:
<223> OTHER INFORMATION: SRCR3 domain of mouse AIM

<400> SEQUENCE: 8

Leu Lys Leu Val Gly Gly Asp Thr Pro Cys Ser Gly Arg Leu Glu Val
1               5                   10                  15

Leu His Lys Gly Ser Trp Gly Ser Val Cys Asp Asp Asn Trp Gly Glu
            20                  25                  30

Lys Glu Asp Gln Val Val Cys Lys Gln Leu Gly Cys Gly Lys Ser Leu
        35                  40                  45

His Pro Ser Pro Lys Thr Arg Lys Ile Tyr Gly Pro Gly Ala Gly Arg
    50                  55                  60

Ile Trp Leu Asp Asp Val Asn Cys Ser Gly Lys Glu Gln Ser Leu Glu
65                  70                  75                  80

Phe Cys Arg His Arg Leu Trp Gly Tyr His Asp Cys Thr His Lys Glu
                85                  90                  95

Asp Val Glu Val Ile Cys Thr
            100

<210> SEQ ID NO 9
<211> LENGTH: 1044
<212> TYPE: DNA
<213> ORGANISM: human

<400> SEQUENCE: 9
atggctctgc tattctcctt gatccttgcc atttgcacca gacctggatt cctagcgtct      60
ccatctggag tgcggctggt ggggggcctc caccgctgtg aagggcgggt ggaggtggaa     120
cagaaaggcc agtggggcac cgtgtgtgat gacggctggg acattaagga cgtggctgtg     180
ttgtgccggg agctgggctg tggagctgcc agcggaaccc ctagtggtat tttgtatgag     240
ccaccagcag aaaaagagca aaaggtcctc atccaatcag tcagttgcac aggaacagaa     300
gatacattgg ctcagtgtga gcaagaagaa gtttatgatt gttcacatga tgaagatgct     360
ggggcatcgt gtgagaaccc agagagctct ttctccccag tcccagaggg tgtcaggctg     420
gctgacggcc ctgggcattg caaggacgc gtggaagtga agcaccagaa ccagtggtat     480
accgtgtgcc agacaggctg gagcctccgg ccgcaaaggg tggtgtgccg gcagctggga     540
tgtgggaggc tgtactgac tcaaaaacgc tgcaacaagc atgcctatgg ccgaaaaccc     600
atctggctga gccagatgtc atgctcagga cgagaagcaa cccttcagga ttgcccttct     660
gggccttggg ggaagaacac ctgcaaccat gatgaagaca cgtgggtcga atgtgaagat     720 cccttttgact tgagactagt aggaggagac aacctctgct ctgggcgact ggaggtgctg     780
cacaagggcg tatgggggctc tgtctgtgat gacaactggg gagaaaagga ggaccaggtg     840
gtatgcaagc aactgggctg tgggaagtcc ctctctccct ccttcagaga ccggaaatgc     900 tatgccctg ggttggccg catctggctg gataatgttc gttgctcagg ggaggagcag     960
tccctggagc agtgccagca cagattttgg gggtttcacg actgcaccca ccaggaagat    1020
gtggctgtca tctgctcagg atag                                            1044

<210> SEQ ID NO 10

```
<211> LENGTH: 1059
<212> TYPE: DNA
<213> ORGANISM: mouse

<400> SEQUENCE: 10
atggctccat tgttcaactt gatgctggcc atcttgagca ttttgttgg atcgtgtttt        60 tcagagtctc caaccaaagt gcagctagtg ggaggtgccc accgctgtga agggcgagtg      120
gaggtggaac acaatggcca gtggggact gtgtgtgatg atggctggga ccggcgtgat      180
gtggctgtgg tgtgccgaga gctcaattgt ggagcagtca tccaaacccc gcgtggcgca      240
tcatatcagc caccagcatc agagcaaaga gttcttattc aaggggttga ctgcaacgga      300
acggaagaca cgttggctca atgtgagcta aattactatg tttttgactg ctcacatgaa      360
gaagatgctg gggcacagtg tgagaaccca gacagtgacc tcctcttcat tccagaggat      420
gtgcgtctag tagatggccc ggggcactgc cagggtcgag tggaggtgct ccaccagtcc      480
cagtggagca ctgtgtgtaa agcaggctgg aacttacagg tctcaaaggt ggtgtgcagg      540
cagctcgggt gtgggcgggc attactgacc tacggaagct gcaacaagaa tactcagggc      600
aaaggaccca tctggatggg caagatgtcg tgttctggac aagaagcaaa ccttcggtct      660
tgccttttga gtcgtttgga gaacaactgt acccatggcg aggacacatg gatggaatgt      720
gaagatccct tgagctgaa gctggtggga ggagacaccc cctgctctgg gaggttggag      780
gtgctacaca agggttcctg gggctctgtc tgtgatgaca ctggggaga aaaggaggac      840 caagtggtct gcaagcaact gggttgtggg aagtccctcc atccatcccc caaacccgg      900 aaaatctatg ggcctggggc aggccgcatc tggctggatg acgtcaactg ctcagggaag      960
gaacagtctc tggagttctg ccggcacagg ttgtgggggt accacgactg tacccacaag     1020
gaagatgtgg aggtgatctg cacagacttt gatgtgtga                           1059

<210> SEQ ID NO 11
<211> LENGTH: 340
<212> TYPE: PRT
<213> ORGANISM: dog

<400> SEQUENCE: 11

Met Ala Leu Leu Phe Ser Leu Ile Leu Ala Ile Cys Thr Gly Pro Gly
1               5                   10                  15

Phe Leu Glu Ser Ser Arg Val Arg Leu Val Gly Gly Asp His Arg
            20                  25                  30

Cys Glu Gly Arg Val Glu Val Gln Arg Tyr Gly Glu Trp Gly Thr Ile
        35                  40                  45

Cys Asp Asp Gly Trp Asp Ile Lys Asp Val Ala Val Cys Arg Glu
    50                  55                  60

Leu Asp Cys Gly Val Ala Lys Arg Ala Leu Ser Gly Thr Leu Phe Gly
65                  70                  75                  80

Pro Pro Thr Gln Gln Gln Lys Ile Phe Ile Gln Gln Val Lys Cys
            85                  90                  95

His Gly Met Glu Glu Asn Leu Ser Gln Cys Glu Glu Glu Asp Ala Phe
            100                 105                 110

Asp Cys Thr His Asp Glu Asp Ala Gly Val Val Cys Gly Phe Pro Glu
        115                 120                 125

Asn Val Arg Leu Val Asp Gly His Lys Arg Cys Gln Gly Arg Val Glu
    130                 135                 140

Val Lys Gln Gln Gly Gln Trp Gly Thr Val Cys Lys Gly Ser Trp Asn
145                 150                 155                 160
```

```
Phe Ala Ala Ala Lys Val Val Cys Gln Gln Val Gly Cys Gly Arg Ala
            165                 170                 175

Ile Leu Thr Arg Lys Cys Cys Asn Lys Ala Thr Gln Gly Gln Gly Pro
        180                 185                 190

Ile Trp Pro Arg Lys Val Ser Cys Ser Gly Lys Glu Ile Ser Leu Gln
            195                 200                 205

Asp Cys Pro Ser Glu Val Trp Glu Lys Asn Asn Cys Thr His Asp Glu
        210                 215                 220

Asp Met Trp Val Glu Cys Glu Asp Pro Phe Asp Leu Lys Leu Val Gly
225                 230                 235                 240

Gly Asp Ser Pro Cys Ala Gly Arg Leu Glu Val Leu His Lys Gly Glu
                245                 250                 255

Trp Gly Thr Val Cys Asp Asp Trp Gly Glu Met Ala Asp Gln Val
            260                 265                 270

Val Cys Arg Gln Leu Gly Cys Gly Ala Ser Leu Ser Pro Ser Val Lys
        275                 280                 285

Phe Arg Arg Arg Phe Gly Pro Gly Val Gly Arg Ile Trp Leu Asp Asp
    290                 295                 300

Val Ala Cys Ser Gly Asn Glu Arg Ser Leu Glu Gln Cys Arg His Arg
305                 310                 315                 320

Phe Trp Gly His His Asn Cys Lys His Thr Glu Asp Val Ala Val Val
                325                 330                 335

Cys Ala Glu Gln
            340

<210> SEQ ID NO 12
<211> LENGTH: 347
<212> TYPE: PRT
<213> ORGANISM: chimpanzee

<400> SEQUENCE: 12

Met Ala Leu Leu Phe Ser Leu Ile Leu Ala Ile Cys Thr Arg Pro Gly
1               5                   10                  15

Phe Leu Ala Ser Pro Ser Gly Val Arg Leu Val Gly Gly Leu His Arg
            20                  25                  30

Cys Glu Gly Arg Val Glu Val Glu Gln Lys Gly Gln Trp Gly Thr Val
        35                  40                  45

Cys Asp Asp Gly Trp Asp Ile Lys Asp Val Ala Val Val Cys Arg Glu
    50                  55                  60

Leu Gly Cys Gly Ala Ala Ser Gly Thr Pro Ser Gly Ile Leu Tyr Glu
65                  70                  75                  80

Pro Pro Ala Glu Lys Glu Gln Lys Val Leu Ile Gln Ser Val Ser Cys
                85                  90                  95

Thr Gly Thr Glu Asp Thr Leu Ala Gln Cys Glu Gln Glu Glu Val Tyr
            100                 105                 110

Asp Cys Ser His Asp Glu Asp Ala Gly Ala Ser Cys Glu Asn Pro Glu
        115                 120                 125

Ser Ser Phe Ser Pro Val Pro Glu Gly Val Arg Leu Ala Asp Gly Pro
    130                 135                 140

Gly His Cys Lys Gly Arg Val Glu Val Lys His Gln Asn Gln Trp Tyr
145                 150                 155                 160

Thr Val Cys Gln Thr Gly Trp Ser Leu Arg Ala Ala Lys Val Val Cys
                165                 170                 175

Arg Gln Leu Gly Cys Gly Arg Ala Val Leu Thr Gln Lys Arg Cys Asn
            180                 185                 190
```

```
Lys His Ala Tyr Gly Arg Lys Pro Ile Trp Leu Ser His Met Ser Cys
        195                 200                 205

Ser Gly Arg Glu Ala Thr Leu Gln Asp Cys Pro Ser Gly Pro Trp Gly
    210                 215                 220

Lys Asn Thr Cys Asn His Asp Glu Asp Thr Trp Val Glu Cys Glu Asp
225                 230                 235                 240

Pro Phe Asp Leu Arg Leu Val Gly Gly Asp Asn Leu Cys Cys Gly Arg
                245                 250                 255

Leu Glu Val Leu His Lys Gly Val Trp Gly Ser Val Cys Asp Asp Asn
            260                 265                 270

Trp Gly Glu Lys Glu Asp Gln Val Val Cys Lys Gln Leu Gly Cys Gly
        275                 280                 285

Lys Ser Leu Ser Pro Ser Phe Arg Asn Arg Lys Cys Tyr Gly Pro Gly
    290                 295                 300

Val Gly Arg Ile Trp Leu Asp Asn Val Arg Cys Ser Gly Glu Glu Gln
305                 310                 315                 320

Ser Leu Glu Gln Cys Gln His Arg Phe Trp Gly Phe His Asp Cys Thr
                325                 330                 335

His Gln Glu Asp Val Ala Val Phe Cys Ser Val
            340                 345
```

<210> SEQ ID NO 13
<211> LENGTH: 346
<212> TYPE: PRT
<213> ORGANISM: rat

<400> SEQUENCE: 13

```
Met Ala Leu Leu Phe Asn Leu Ile Leu Ala Leu Leu Thr Ile Phe Val
1               5                   10                  15

Gly Leu Cys Phe Ser Glu Ser Pro Thr Arg Val Arg Leu Val Gly Gly
            20                  25                  30

Ala His Arg Cys Glu Gly Arg Val Glu Val Lys His Asn Gly Gln Trp
        35                  40                  45

Gly Thr Val Cys Asp Asp Gly Trp Asp Leu Ile Asp Val Ser Val Val
    50                  55                  60

Cys Arg Glu Leu Asn Cys Gly Ala Ala Lys Lys Thr Pro Ser Gly Ala
65                  70                  75                  80

Ser Tyr His Pro Pro Ala Ser Glu Gly Gln Ser Val Leu Ile Gln Gly
                85                  90                  95

Val Glu Cys Ser Gly Ala Glu Asp Met Leu Ala Gln Cys Thr Leu Asn
            100                 105                 110

Tyr Asp Val Phe Asp Cys Ser His Ala Glu Asp Ala Gly Val Gln Cys
        115                 120                 125

Glu Asn Pro Asp Asn Pro Glu Asn Val Arg Leu Val Glu Gly Leu Gly
    130                 135                 140

Arg Cys Gln Gly Arg Leu Glu Val Phe Tyr Gln Gly Gln Trp Ser Thr
145                 150                 155                 160

Val Cys Lys Ala Gly Trp Asn Leu Gln Ala Ser Lys Val Val Cys Arg
                165                 170                 175

Gln Leu Gly Cys Gly Arg Ala Leu Leu Ala His Arg Cys Cys Asn Lys
            180                 185                 190

Asn Thr Gln Gly Lys Gly Pro Ile Trp Met Ser Lys Met Ser Cys Ser
        195                 200                 205

Gly Arg Glu Ala Asn Leu Gln Asp Cys Pro Phe Ser Pro Leu Glu Ser
    210                 215                 220
```

-continued

```
Asn Cys Thr His Gly Glu Asp Thr Trp Met Glu Cys Glu Asp Pro Phe
225                 230                 235                 240

Glu Leu Arg Leu Val Gly Gly Asp Thr Thr Cys Ser Gly Arg Leu Glu
            245                 250                 255

Val Leu His Lys Gly Ser Trp Gly Ser Val Cys Asp Asp Ser Trp Gly
            260                 265                 270

Glu Lys Glu Asp Gln Val Val Cys Lys Gln Leu Gly Cys Gly Lys Ser
        275                 280                 285

Leu Phe Pro Ser Pro Lys Ala Arg Gln Ser Phe Gly Pro Gly Thr Gly
    290                 295                 300

Arg Ile Trp Leu Asp Asp Val Ser Cys Ser Gly Lys Glu Glu Ser Leu
305                 310                 315                 320

Glu Leu Cys Arg His Arg Leu Trp Gly Tyr His Asp Cys Thr His Lys
            325                 330                 335

Glu Asp Val Gly Val Ile Cys Ser Glu Leu
            340                 345
```